(12) United States Patent
Akutagawa et al.

(10) Patent No.: US 11,397,997 B2
(45) Date of Patent: *Jul. 26, 2022

(54) DEVICE FOR IMPLEMENTING BODY FLUID ANALYSIS AND SOCIAL NETWORKING EVENT PLANNING

(71) Applicants: Christine E. Akutagawa, Sunnyvale, CA (US); Lucas J. Myslinski, Sunnyvale, CA (US)

(72) Inventors: Christine E. Akutagawa, Sunnyvale, CA (US); Lucas J. Myslinski, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/018,431

(22) Filed: Sep. 11, 2020

(65) Prior Publication Data

US 2020/0410608 A1    Dec. 31, 2020

Related U.S. Application Data

(63) Continuation of application No. 15/608,637, filed on May 30, 2017, now Pat. No. 10,984,486, which is a
(Continued)

(51) Int. Cl.
*G06Q 50/00* (2012.01)
*G06Q 50/12* (2012.01)
(Continued)

(52) U.S. Cl.
CPC ......... *G06Q 50/01* (2013.01); *A61B 10/0064* (2013.01); *G01K 13/20* (2021.01);
(Continued)

(58) Field of Classification Search
CPC combination set(s) only.
See application file for complete search history.

(56) References Cited

U.S. PATENT DOCUMENTS 6,681,108 B1 * 1/2004 Terry ..................... G06Q 10/10
340/5.1
6,904,408 B1    6/2005 McCarthy
(Continued)

FOREIGN PATENT DOCUMENTS

EP          2587436 A2 *  5/2013   ......... G06K 9/00302

OTHER PUBLICATIONS

W. Z. Khan, Y. Xiang, M. Y. Aalsalem and Q. Arshad, "Mobile Phone Sensing Systems: A Survey," in IEEE Communications Surveys & Tutorials, vol. 15, No. 1, pp. 402-427, First Quarter 2013, doi: 10.1109/SURV.2012.031412.00077. (Year: 2012).*

(Continued)

*Primary Examiner* — Crystol Stewart
(74) *Attorney, Agent, or Firm* — Haverstock & Owens, A Law Corporation

(57) ABSTRACT

Event planning using social networking enables an efficient implementation of planning an event, as well as minimizing network traffic and optimizing other technological aspects of life. Additional information acquired by sensors and other technology is able to improve the quality of the event planning Social network information as well as the additional information is able to be used to select aspects of the event such as time, location, and/or many other aspects of the event.

20 Claims, 10 Drawing Sheets

Related U.S. Application Data continuation of application No. 15/131,210, filed on Apr. 18, 2016, now Pat. No. 9,704,205, which is a continuation-in-part of application No. 14/631,279, filed on Feb. 25, 2015, now abandoned.

(60) Provisional application No. 62/016,720, filed on Jun. 25, 2014, provisional application No. 61/946,306, filed on Feb. 28, 2014.

(51) Int. Cl.

| | | |
|---|---|---|
| *G06Q 10/10* | (2012.01) | |
| *G06Q 30/02* | (2012.01) | |
| *A61B 10/00* | (2006.01) | |
| *G16H 40/63* | (2018.01) | |
| *G06F 16/9032* | (2019.01) | |
| *H04W 4/21* | (2018.01) | |
| *G06F 40/30* | (2020.01) | |
| *H04L 65/403* | (2022.01) | |
| *G06T 7/20* | (2017.01) | |
| *A63B 24/00* | (2006.01) | |
| *H04L 51/222* | (2022.01) | |
| *H04L 51/52* | (2022.01) | |
| *H04L 51/00* | (2022.01) | |
| *G06K 19/07* | (2006.01) | |
| *G01K 13/20* | (2021.01) | |

(52) U.S. Cl.
CPC ........ *G06F 16/90324* (2019.01); *G06F 40/30* (2020.01); *G06K 19/0707* (2013.01); *G06Q 10/1095* (2013.01); *G06Q 30/0201* (2013.01); *G06Q 30/0207* (2013.01); *G06Q 50/12* (2013.01); *G16H 40/63* (2018.01); *H04L 51/14* (2013.01); *H04L 51/20* (2013.01); *H04L 51/32* (2013.01); *H04L 65/403* (2013.01); *H04W 4/21* (2018.02); *A63B 24/00* (2013.01); *G06T 7/20* (2013.01)

(56) References Cited

U.S. PATENT DOCUMENTS

| | | | |
|---|---|---|---|
| 8,447,331 | B2 | 5/2013 | Busch |
| 8,515,459 | B2 | 8/2013 | Busch |
| 8,559,977 | B2 | 10/2013 | Busch |
| 8,626,194 | B2 | 1/2014 | Busch |
| 8,909,674 | B2 | 12/2014 | Kolias |
| 9,241,635 | B2 | 1/2016 | Yuen et al. |
| 9,241,665 | B2 | 1/2016 | deCharms |
| 9,246,866 | B1 | 1/2016 | Sanders |
| 9,247,884 | B2 | 2/2016 | Yuen et al. |
| 9,254,099 | B2 | 2/2016 | Connor |
| 9,363,221 | B1 | 6/2016 | Ozog |
| 9,406,091 | B1 | 8/2016 | Lopez |
| 10,335,636 | B2 | 7/2019 | Holma |
| 2003/0209451 | A1 | 11/2003 | Dineen |
| 2004/0059212 | A1 | 3/2004 | Abreu |
| 2004/0235293 | A1 | 11/2004 | Abreu |
| 2005/0118723 | A1 | 6/2005 | Padmanabhan et al. |
| 2005/0278206 | A1 | 12/2005 | Choper |
| 2007/0031283 | A1 | 2/2007 | Davis |
| 2007/0093786 | A1 | 4/2007 | Goldsmith |
| 2008/0141681 | A1 | 6/2008 | Arnold |
| 2008/0255471 | A1 | 10/2008 | Naghavi |
| 2009/0061534 | A1 | 3/2009 | Sharrock |
| 2009/0164624 | A1 | 3/2009 | Metcalf |
| 2009/0240600 | A1 | 9/2009 | Soulanille |
| 2009/0327013 | A1 | 12/2009 | McGovern et al. |
| 2010/0087717 | A1 | 4/2010 | Onoe et al. |
| 2010/0125475 | A1 | 5/2010 | Twyman |
| 2010/0180211 | A1 | 7/2010 | Boyd |
| 2010/0205541 | A1 | 8/2010 | Rapaport |
| 2011/0033830 | A1* | 2/2011 | Cherian ............ G16H 20/30 434/236 |
| 2011/0040756 | A1 | 2/2011 | Jones |
| 2011/0053270 | A1 | 3/2011 | Chang |
| 2011/0112904 | A1 | 5/2011 | Stupp |
| 2011/0185020 | A1 | 7/2011 | Ramamurthy et al. |
| 2011/0208617 | A1* | 8/2011 | Weiland ............ G06Q 30/0641 705/27.1 |
| 2011/0275940 | A1 | 11/2011 | Nims |
| 2011/0276507 | A1 | 11/2011 | O'Malley |
| 2011/0283218 | A1 | 11/2011 | Schwendimann et al. |
| 2012/0023031 | A1 | 1/2012 | Galya |
| 2012/0095931 | A1 | 4/2012 | Gurion et al. |
| 2012/0109838 | A1 | 5/2012 | Younger et al. |
| 2012/0116684 | A1 | 5/2012 | Ingrassia, Jr. |
| 2012/0136689 | A1 | 5/2012 | Ickman |
| 2012/0166257 | A1 | 6/2012 | Shiragami |
| 2012/0180107 | A1 | 7/2012 | Gammill |
| 2012/0290508 | A1 | 11/2012 | Bist |
| 2012/0290950 | A1 | 11/2012 | Rapaport et al. |
| 2012/0303415 | A1 | 11/2012 | Edelson |
| 2013/0046770 | A1 | 2/2013 | Tseng |
| 2013/0054698 | A1 | 2/2013 | Lee |
| 2013/0171304 | A1 | 2/2013 | Huntley |
| 2013/0097093 | A1 | 4/2013 | Kolber et al. |
| 2013/0103624 | A1* | 4/2013 | Thieberger ........... G06K 9/6256 706/12 |
| 2013/0117109 | A1 | 5/2013 | Busch |
| 2013/0130719 | A1 | 5/2013 | Busch |
| 2013/0137463 | A1 | 5/2013 | Busch |
| 2013/0173531 | A1 | 7/2013 | Rinearson |
| 2013/0198694 | A1 | 8/2013 | Rahman |
| 2013/0210463 | A1 | 8/2013 | Busch |
| 2013/0234826 | A1 | 9/2013 | Sekiguchi |
| 2013/0235042 | A1 | 9/2013 | Wolfe et al. |
| 2013/0254309 | A1 | 9/2013 | Jackson et al. |
| 2013/0268593 | A1 | 10/2013 | Parekh |
| 2013/0282446 | A1 | 10/2013 | Dobell |
| 2013/0282605 | A1 | 10/2013 | Noelting |
| 2013/0289370 | A1 | 10/2013 | Sun et al. |
| 2013/0290207 | A1 | 10/2013 | Bonmassar |
| 2013/0310082 | A1* | 11/2013 | Takaoka ................ H04W 4/023 455/456.3 |
| 2013/0312108 | A1 | 11/2013 | Mourad et al. |
| 2013/0317873 | A1 | 11/2013 | Kozloski |
| 2013/0318180 | A1 | 11/2013 | Amin et al. |
| 2013/0332307 | A1 | 12/2013 | Linden |
| 2013/0332525 | A1 | 12/2013 | Liu et al. |
| 2013/0343618 | A1 | 12/2013 | Zomet et al. |
| 2013/0345957 | A1 | 12/2013 | Yang et al. |
| 2013/0345961 | A1 | 12/2013 | Leader et al. |
| 2013/0345971 | A1 | 12/2013 | Stamm et al. |
| 2013/0346347 | A1 | 12/2013 | Patterson et al. |
| 2013/0346403 | A1 | 12/2013 | Petersen et al. |
| 2014/0006388 | A1 | 1/2014 | Lopyrev et al. |
| 2014/0006497 | A1 | 1/2014 | Lopyrev et al. |
| 2014/0006515 | A1 | 1/2014 | Yeskel et al. |
| 2014/0006525 | A1 | 1/2014 | Freund et al. |
| 2014/0012792 | A1 | 1/2014 | Huang |
| 2014/0013240 | A1 | 1/2014 | Ganesh |
| 2014/0032453 | A1 | 1/2014 | Eustice |
| 2014/0039842 | A1 | 2/2014 | Yuen |
| 2014/0052567 | A1 | 2/2014 | Bhardwaj |
| 2014/0058768 | A1 | 2/2014 | Moxley et al. |
| 2014/0108333 | A1 | 4/2014 | Jain |
| 2014/0120119 | A1 | 5/2014 | Kobayashi et al. |
| 2014/0129242 | A1 | 5/2014 | Utter, II |
| 2014/0135612 | A1* | 5/2014 | Yuen ..................... A61B 5/112 600/407 |
| 2014/0168349 | A1 | 6/2014 | Eom |
| 2014/0172996 | A1 | 6/2014 | Deeter |
| 2014/0195026 | A1 | 7/2014 | Wieder |
| 2014/0227676 | A1* | 8/2014 | Noshadi ................ G09B 5/02 434/365 |
| 2014/0235293 | A1 | 8/2014 | Sheldon |
| 2014/0276244 | A1 | 9/2014 | Kamyar |
| 2014/0288680 | A1 | 9/2014 | Hoffman |
| 2014/0289241 | A1 | 9/2014 | Anderson |

(56) References Cited

U.S. PATENT DOCUMENTS

| | | | |
|---|---|---|---|
| 2014/0323817 A1* | 10/2014 | el Kaliouby | G16H 20/40 600/300 |
| 2015/0019273 A1 | 1/2015 | Grosz | |
| 2015/0039549 A1 | 2/2015 | Aufmann | |
| 2015/0049902 A1 | 2/2015 | Moraleda | |
| 2015/0057515 A1 | 2/2015 | Hagen | |
| 2015/0057945 A1 | 2/2015 | White | |
| 2015/0112164 A1 | 4/2015 | Heikenfeld | |
| 2015/0149230 A1 | 5/2015 | Neiman | |
| 2015/0244539 A1* | 8/2015 | Ickman | H04N 21/4788 709/204 |
| 2016/0226989 A1 | 8/2016 | Ovsiankin | |
| 2016/0270717 A1 | 9/2016 | Luna | |
| 2017/0202484 A1 | 7/2017 | Al-shaery | |
| 2018/0012460 A1 | 1/2018 | Heitz, III | |

OTHER PUBLICATIONS

Office Action from U.S. Appl. No. 15/608,637 (dated Feb. 5, 2020).
Notice of Allowance from U.S. Appl. No. 15/608,637.
Dubay, Lee, Optical sensor-driven device can count white blood cells through the skin, BioOptics World, http://www.bioopticsworld.com/articles/2015/10/optical-sensor-driven-device-can-count-white-blood-cells-through-the-skin.html (Oct. 1, 2015).
Heikenfeld, Jason, Sweat Sensors Will Change How Wearables Track Your Health, http://spectrum.ieee.org/biomedical/diagnostics/sweat-sensors-will-change-how-wearables-track-your-health (Oct. 22, 2014).
Coyle, Shirley et al., Textile Sensors to Measure Sweat pH and Sweat-rate During Exercise, Pervasive Computing Technologies for Healthcare, 2009, 3rd International Conference on Apr. 1-3, 2009.
Non-Final Office Action from U.S. Appl. No. 15/131,210.
Final Office Action from U.S. Appl. No. 15/131,210.
Advisory Action from U.S. Appl. No. 15/131,210.
Notice of Allowance from U.S. Appl. No. 15/131,210.
Final Office Action from U.S. Appl. No. 14/631,279 (dated Oct. 30, 2018).
Jenkins, J., EIC 3600 Search Report dated Oct. 22, 2018, p. 1-4, 8 (Year: 2018).
Office Action from U.S. Appl. No. 14/631,279.

* cited by examiner

400

| Name | Food Like | Food Dislike | Activity Like | Activity Dislike | Schedule |
|------|-----------|--------------|---------------|------------------|----------|
| Bob | Pizza, Burgers | Seafood | Hiking | Tennis | Classes 6-9p, M-F |

402

| Name | Pizza | Burgers | Seafood | German | ... | Hiking | Tennis | ... |
|------|-------|---------|---------|--------|-----|--------|--------|-----|
| Bob | Y | Y | N | N | ... | Y | N | ... |

404

| Pizza Likes |
|-------------|
| Bob |
| Ted |
| ... |

Fig. 4

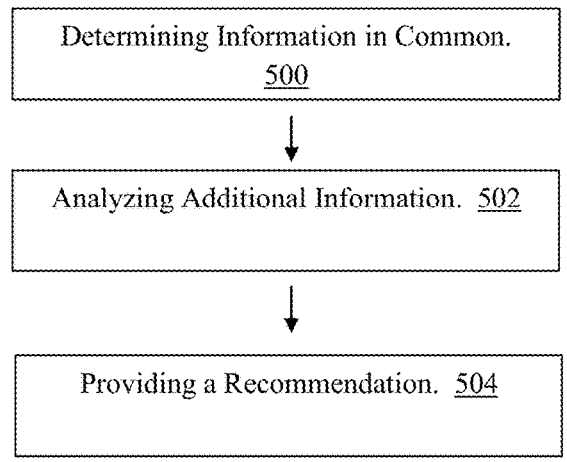

Fig. 5

| Likes | Dislikes | Traffic | Wait Times | Mood |
|---|---|---|---|---|
| Current Location | Future Location | Diet | Adventure Rating | Coupon |
| Type | Weather | Health | Music | Gaming |
| Brain Waves | Microchip | Purchases | Searches | Tracking |
| Patterns | To-Do | TV/Movies | Communications | Images/Videos |
| Internet of Everything | Augmented Reality | Employment Information | Travel | Pets |
| Kids | Share Items | Quests | Real-time | Learning |
| Parallel | Reaction | Comparison | Nanoparticles | Additional Information |

Fig. 6

| Factor | Weight |
|---|---|
| Likes | 10 |
| Dislikes | 10 |
| Traffic | 8 |
| Wait | 8 |
| Distance | 8 |
| Recent Info | 7 |
| Adventure | 5 |
| Searches | 4 |
| Weather | 2 |

| Calculations | Process of Elimination | Multiple Suggestions |
|---|---|---|
| Specific Information | Accept / Reject | Percent Likelihood |
| Images | Video | Scent |
| Options | Random | Wearable Items |
| Caller ID | Short Cut | Other Recommendation Analysis |

| Interests | Personalities | Location |
| --- | --- | --- |
| Employee | Employer | Contacts |
| Search | College | Sequence |
| Life | Salary | Genetics |

DEVICE FOR IMPLEMENTING BODY FLUID ANALYSIS AND SOCIAL NETWORKING EVENT PLANNING

CROSS-REFERENCE TO RELATED APPLICATION(S)

This application is a continuation application of co-pending U.S. patent application Ser. No. 15/608,637, filed on May 30, 2017, and titled "DEVICE FOR IMPLEMENTING BODY FLUID ANALYSIS AND SOCIAL NETWORKING EVENT PLANNING," which is a continuation application of U.S. patent application Ser. No. 15/131,210 (now U.S. Pat. No. 9,704,205), filed on Apr. 18, 2016, and titled "DEVICE FOR IMPLEMENTING BODY FLUID ANALYSIS AND SOCIAL NETWORKING EVENT PLANNING," which is a continuation-in-part application of U.S. patent application Ser. No. 14/631,279, filed on Feb. 25, 2015, and titled "SOCIAL NETWORKING EVENT PLANNING," which claims the benefit of U.S. Provisional Patent Application Ser. No. 61/946,306, filed Feb. 28, 2014, and titled "SOCIAL NETWORKING EVENT PLANNING" and U.S. Provisional Patent Application Ser. No. 62/016,720, filed Jun. 25, 2014, and titled "SOCIAL NETWORKING EVENT PLANNING," which are all hereby incorporated by reference in their entireties for all purposes.

FIELD OF THE INVENTION

The present invention relates to the field of social networking. More specifically, the present invention relates to the field of event planning via social networking.

BACKGROUND OF THE INVENTION

Several ways exist of organizing a social gathering such as using electronic invitations; however, these invitations have many technical or technological deficiencies. Social networking is able to be used to improve upon event planning.

SUMMARY OF THE INVENTION

Event planning using social networking enables an efficient implementation of planning an event, as well as minimizing network traffic and optimizing other technological aspects of life. Additional information acquired by sensors and other technology is able to improve the quality of the event planning Social network information as well as the additional information is able to be used to select aspects of the event such as time, location, and/or many other aspects of the event.

BRIEF DESCRIPTION OF THE DRAWINGS

FIG. 4 illustrates diagrams of exemplary common interest data structures according to some embodiments.

FIG. 5 illustrates a flowchart of a method of utilizing the social networking event planning system for employment searches according to some embodiments.

FIG. 6 illustrates a diagram of exemplary factors utilized in making a recommendation according to some embodiments.

DETAILED DESCRIPTION OF THE PREFERRED EMBODIMENT

A social network event planning system provides a simpler and more efficient way of planning an event such as breakfast, lunch, dinner, coffee, drinks, another get-together, a sporting event (e.g., attending or participating in), a meeting, an activity (e.g., hiking), a show/performance (e.g., live performance/concert), a movie, gambling, a television program, Internet site event, microblog event, social network event, video performance, a party, an interview, a business meeting, a casting call, or any other event. In some embodiments, information is utilized from different sources to automatically suggest an event and/or the location and/or time of the event.

The phrase "social networking system" or "social networking site" as used herein encompasses its plain and ordinary meaning, including, but not limited to, an online site, system or service that focuses on building and enabling social associations and interactions among users. The associations are able to be stored in any manner such as within a social graph. Users are able to generate associations with one another, and associations are able to be computer-generated. The associations are able to include groups of varying sizes.

The term "friend" as used herein encompasses its plain and ordinary meaning, as well as, the meaning used in the social networking context, including, but not limited to, a user of a social networking site with which another user has an association.

In some embodiments, a plurality of users communicate, and the social networking event planning system assists them in planning an event. For example, several users send text messages to each other to plan a get-together, and the social networking event planning system provides a recommendation. In some embodiments, a user plans an event by himself with minimal or no active input from other users. For example, a user wants to get his friends together, selects their names from a list, and the social networking event planning system provides him with a recommendation based on their names and other information previously acquired about them.

Figure 1:
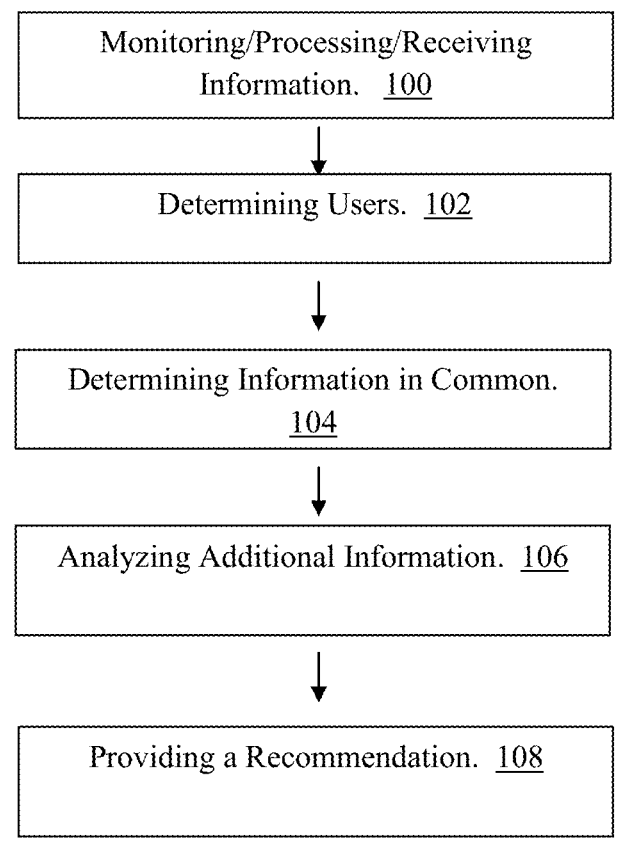
FIG. 1 illustrates a flowchart of a method of implementing event planning using social networking according to some embodiments.

FIG. 1 illustrates a flowchart of a method of implementing event planning using social networking according to some embodiments.

In the step 100, information is monitored, processed and/or received. The information is able to be monitored in real-time or non-real-time. For example, a phone call, microblog message (e.g., tweet), a social network message, an SMS message, and/or any other communication is monitored. Other communications to be monitored include: email, documents, social networking/media content (Facebook® postings), webpages, user review sites (Yelp.com, Google®, Tripadvisor) message boards, web logs, any computing device communication, VoIP calls, chatting, Snapchat content, video chatting, video conferencing, images, videos, live conversations, holographic images, recorded visual messages, and/or any other information. The monitoring/processing/receiving is for acquiring information such as the names/IDs of the users involved in the meeting, time information, location information and/or any other information that may be helpful in planning an event. In some embodiments, the tone/mood of a conversation/communication is analyzed/determined automatically. For example, by comparing the content of a message with templates or previous writings by the person providing the message, the tone/mood of the message is able to be determined. The users communicating are able to be determined in any manner such as by detecting a username, caller identification, voice/facial recognition, device identification, biometric analysis, and/or any other manner.

Depending on the information, the information may be processed. For example, audio is converted to text, and text is parsed for phrases. In some embodiments, specific keywords are searched for when parsing. For example, the phrases, "let's do," "want to get something to eat," or "dinner" are keywords/phrases that are searched for when monitoring/parsing. Then, the content after the specific keywords is parsed/analyzed/processed to acquire information relevant to event planning.

Processing is able to include many aspects including, but not limited to, converting (e.g., audio into text), formatting, parsing, determining context, transmitting, searching, converting an image into text, analyzing and reconfiguring, and/or any other aspect that enables the information to be analyzed. In some embodiments, processing includes converting the information into a searchable format. In some embodiments, processing occurs concurrently with monitoring. In some embodiments, processing includes capturing/receiving and/or transmitting the information (e.g., to/from the cloud).

Parsing is able to be implemented in any manner including, but not limited to, based on sentence structure (e.g., subject/verb determination), based on punctuation including, but not limited to, end punctuation of each sentence (e.g., period, question mark, exclamation point), intermediate punctuation such as commas and semi-colons, based on other grammatical features such as conjunctions, based on capital letters, based on a duration of a pause between words (e.g., two seconds), based on duration of a pause between words by comparison (e.g., typical pauses between words for user are 0.25 seconds and pauses between thoughts are one second)—the user's speech is able to be analyzed to determine speech patterns such as length of pauses between words lasting a fourth of the length for pauses between thoughts or sentences, based on a change of a speaker (e.g., Speaker A is talking, then Speaker B starts talking), based on a word count (e.g., 10 word segments), based on speech analysis, based on a slowed down version (recording the content, slowing down the recorded content to determine timing breaks), based on keywords/key phrases, based on search results, and/or any other manner. In some embodiments, processing includes, but is not limited to, calculating, computing, storing, recognition, speaker recognition, language (word, phrase, sentence, other) recognition, labeling, and/or characterizing.

Information is able to be received directly from one or more users as well. For example, users are able to manually input selections and/or other information. Furthering the example, a user is able to specify that he is available from 7 pm to 10 pm for dinner. In another example, the user is able to ask directly, "find a good place for dinner for a meeting."

In some embodiments, the implementation is able to occur without a communication between parties. For example, if a boyfriend is planning a date, he is able to do so without a communication with his girlfriend being detected. Furthering the example, the user opens up an "app" to assist in planning an event, and the user provides details. In some embodiments, the app automatically recognizes the user by his name, username, phone number, IP address, device ID, voice recognition, and/or any other identifying information, and the additional parties are either manually input (e.g., select the girlfriend by touchscreen) and/or automatically determined/suggested based on social networking information and/or other information. For example, the app is able to store information that the user goes to dinner with his girlfriend on Friday nights, so the app is able to suggest locations. The app is also able to modify selections depending on updated information—for example, traffic problems, long wait times, poor reviews, duration of time since last dining at a particular restaurant, and/or any other information.

In the step 102, users are determined. Determining the users is able to be implemented in any manner such as using caller identification for a phone call, analyzing usernames (e.g., social network), recognizing names, voice/facial recognition, device identification, biometric information, location information, and/or any other identification implementations. In some embodiments, users are manually input. For example, a user selects (by touchscreen, voice command, physical cue or thought control) from a contact list that he wants to meet up with Contact A, Contact B and Contact C. In some embodiments, users are able to generate groups or subgroups of contacts. For example, a user has 550 social network contacts, so the user has generated a dinner buddies group which includes four friends (of the 550 contacts) with which he frequently has dinner.

In the step 104, information in common is determined (e.g., likes or dislikes common to two or more people). For example, user and Contacts A, B and C all like pizza and burgers. In some embodiments, this step is performed separately (e.g., before the step of monitoring), and a data structure stores the results. For example, a database stores contacts, likes, dislikes, allergies, favorites, similarities and/or any other relevant information. In some embodiments, the steps 104 and 106 are combined or used in conjunction. For example, determining the information in common is performed by analyzing the additional information. There are many ways of determining information in common. As described herein, a data structure (e.g., database) is able to store users/contacts and their likes such as food likes/dislikes, activity likes/dislikes, and/or any other preferences. The data is able to be stored in any manner. For example, a database is generated for each contact group, and all of their common likes are included in the database. The database is able to be populated by utilizing a crawler for crawling for information, manually, or any other manner. In another example, a database includes users and all likes/dislikes or preferences of each user. Continuing with the examples, User A wants to meet up with User B and User C. A database stores that User A likes pizza, burgers and Italian food, User B likes pizza, burgers, French food and Indian food, and User C likes pizza, burgers, seafood and Chinese food. So User A, User B and User C have pizza and burgers as foods in common. Other information in common of contacts is able to be determined and used such as age, health issues (e.g., allergies, high cholesterol, low carb diet), schools/colleges attended, location, and/or any other information.

In some embodiments, common interests of groups that meet up often (e.g., above a threshold) are stored, so that re-analysis/recalculations do need to be performed. For example, if Users A, B and C meet up once a week, their common interests are stored.

In some embodiments, instead of or in addition to finding common interests, each cuisine/activity has a number rating for each user. For example, User A gives Italian food a 10 (on a scale of 1 to 10) but French food a 2. In some embodiments, the number is automatically generated by analyzing the user's comments, social networking information, reviews and/or any other information. The number ratings are then able to be used when generating a recommendation. For example, User A gave Italian food a 10, User B gave Italian food an 8 and User C gave Italian food a 7, but User A gave French food a 2, User B gave French food a 7 and User C gave French food a 9. Since the total for Italian food is greater than French food, that type of restaurant is searched for. In some embodiments, ranges or thresholds are implemented using the numbers provided. For example, a value of 9-10 is considered "likes a lot," 7-8 is "likes," 4-6 is "neutral" and 1-3 is "dislikes." When determining common interests, if the value for the users is in the same range, then it is considered to be a common interest. In some embodiments, if the value is above, for example, a "7," then it is considered to be a common interest. The values are able to be used in any manner to compute a recommendation.

In some embodiments, each specific event (e.g., restaurant, hike, golf course) is able to be rated or ranked by users, and the rating or ranking is utilized (e.g., by comparing the ratings) to determine common likes/dislikes and provide a suggestion. For example, a user inputs that his favorite restaurant is Restaurant W, and his second favorite restaurant is Restaurant Z, and so on. In some embodiments, each event has sub-categories. For example, restaurants have sub-categories for each cuisine (e.g., Italian, seafood, Chinese). The users are able to rank restaurants by category such as Restaurant W is the user's favorite Chinese restaurant, Restaurant J is his second favorite restaurant, and Restaurant Z is his favorite Indian restaurant. In some embodiments, specific comparisons/preferences are made and stored. For example, a user specifies that for coffee, he prefers Coffee Shop X over Coffee Shop Z. In some embodiments, events that have higher ratings or rankings are given more weight. In some embodiments, each specific event is automatically given a rating and/or ranking. The automatic rating/ranking is able to be determined or generated based on the number of times the user visits a place, reviews by a user, social networking information, and/or any other information. For example, User A sends a tweet that says, "Restaurant V is my new favorite Indian restaurant." Based on this, the previous #1 ranked Indian restaurant becomes #2, the #2 Indian restaurant becomes #3 and so on, and Restaurant V becomes #1. In another example, User B ate at Restaurant K 20 times, Restaurant M 5 times, Restaurant W 3 times, and so on, as determined by check-ins or analyzed receipts or another implementation. So Restaurant K is ranked #1, Restaurant M is #2, and so on. In some embodiments, restaurants are classified by cuisine automatically for ranking. For example, the system is able to determine that Restaurant K using keyword comparison (e.g., detect "Indian" in the description) or a database lookup or another implementation. In some embodiments, trends are analyzed. For example, if a user has visited Restaurant K 20 times but those 20 visits were four years ago or longer, then the ranking is affected (e.g., lowered). Trending is able to be determined by analyzing date information and/or visit information. In some embodiments, only visits within the last month, last six months, or one year are used. In some embodiments, the weight of visits are affected based on the date of the visit. For example, visits within the past month receive 2× points, visits within six months receive 1× points, visits over six months are ½× points, and visits 2 years or further receive 0 points. If visits locations for periods of time (e.g., User A visits Seattle every other month), then the analysis of lowering effects based on time is able to be modified. For example, User A is only in Seattle for five days out of sixty, so instead of a visit within the past month receiving 2× points, a visit within the past year receives 2× points. In some embodiments, users are able to specify aspects of an event such as Restaurant Z has great food but small portions, and Restaurant L has good food and large portions. The specific aspects are able to be used when performing analysis. For example, if User A is on a diet, Restaurant L is not a good choice, so it will be negatively affected when calculating a recommendation. The specific aspects are able to be stored as sub-classes or substructures in a data structure for each event which are then able to be analyzed when generating a recommendation.

In the step 106, additional information is analyzed. The information is analyzed in any manner, such as by text comparison, natural language comparison, comparing data structure/database information, and/or any other analysis/comparison. Analysis is able to include processing, computing, comparing and/or any other form of analysis.

Examples of additional information include the current location of people that are meeting (or potentially meeting), the distance of those people to the event and/or in relation to other people meeting, the current traffic, hours of operation, wait times for locations (e.g., over one hour wait time at Z Restaurant), reservation information, weather information, user preferences and/or type of restaurant (e.g., noisy, good for kids, romantic, allows dogs, alcohol served). In some embodiments, an auto-reserve implementation is utilized such that if a location and time is acceptable to/accepted by all parties, then a reservation is automatically placed. Similarly, tickets are able to be automatically purchased, and/or any other action is able to be automatically performed. For example, an e-vite is accepted, users text back a response, and/or any other acceptance is provided by the users.

In some embodiments, one or more users or contacts are able to specify a type of event for the event planner to recommend. For example, instead of determining any event out of all possible events, a user specifies that he wants to go on a hike with some of his contacts. The level of specificity is able to vary. For example, the user is able to specify he wants to do an outdoor activity (very broad), or he wants to go on a hike on Saturday, in the North Bay, where there are views of the ocean (very specific), or anywhere in between. In some embodiments, the type of event is automatically generated and/or provided to one or more users or contacts for approval. For example, the event planning system determines that Contacts A, B, C and D all enjoy hiking, surfing and rock climbing based on analysis of social networking content, so a message is sent to Contact A (or all) to select one of the activities, and then the event planning system plans an event specific to that selection.

In some embodiments, information is analyzed in real-time to change an event based on the current analysis/information. For example, Restaurant Z was initially recommended for Contacts A, B and C, but bad traffic is going to mean that Contact C will be 30 minutes late, so the event planner changes the recommended event in real-time (e.g., to a location closer to Contact C), so that Contact C will not be late. In some embodiments, the real-time recommendation change is sent to the contacts for approval including an explanation as to why there is a recommended change (e.g., traffic conditions for Contact C). Any analysis in real-time is able to be performed to affect the recommendation. For example, if a contact cancels at the last minute, a recalculation of the recommendation is able to be performed in real-time. In another example, a hike was recommended to several contacts, but a sudden storm appeared, so a recommendation for an indoor climbing wall is recommended. By real-time, the analysis occurs automatically based on events/information that is occurring at the time of the real-time analysis. For example, the analysis occurs with the speed that a user driving is able to change his course if a new event is recommended. In some embodiments, the real-time analysis is incorporated in a vehicle navigation system. For example, in a car, truck, boat, plane, and/or any other vehicle, the real-time event planning system receives updates and makes changes in real-time. Furthering the example, if a recommendation changes due to traffic or weather, the vehicle is able to automatically change course based on the change. The real-time analysis is able to be performed for job-related scenarios as well. For example, if a user is planning on meeting with Partner X for an interview, and the schedule is changed so that Partner Z is meeting the user, information about Partner Z is able to be provided to the user. In another example, a user is scheduled to meet with Partner X but Partner X becomes ill and will not be able to attend, so Partner Z takes his place. A recalculation is made to recommend a restaurant that is better for the user and Partner Z based on their preferences and/or other factors.

The additional information is able to be information from Internet of Everything devices, social network information (e.g., tweets/Twitter®, Facebook® postings), date/time/calendar information (e.g., near Christmas suggest a place for peppermint milkshake, 6 pm suggest dinner, birthdays/graduations/new job/other milestones/accomplishments), dating site information, review information (e.g., yelp.com reviews), review site selections (e.g., "funny, helpful, cool" selections on yelp.com), preferences (e.g., user likes Italian food), likes/dislikes submitted on web pages (e.g., youtube.com), message board information (e.g., user comments, user thumbs up/down for another user's comment), viewed videos, location information (e.g., GPS information of each user, IP address location or basic user information), comments on web pages, pinned content using Pinterest, shared photos/videos (e.g., using Instagram, Flickr), and/or any other information.

Although likes and dislikes of food (e.g, cuisine, dishes, and/or ingredients) may be determined in the previous step, likes and dislikes of food of the people meeting is also able to be determined by analyzing the additional information. For example, if a user has reviewed restaurants on a review website such as yelp.com, that information is able to be analyzed and used. Furthering the example, a username is searched for/detected, the review is analyzed (e.g., search for keywords and/or number/letter ratings), and a result/information is returned. Other sites such as social networking sites and likes/dislikes on web pages are able to be analyzed to determine food/cuisine preferences and/or favorite restaurants. In some embodiments, the reviews/ratings of restaurants (or other location/activity) are limited to only the people meeting, and in some embodiments, the reviews include other people's reviews. In some embodiments, when a user makes a review, the review is stored in a secondary location (e.g., database), so that the review does not need to be searched for on the Web. For example, User A writes a Yelp review for Restaurant Z. The review is posted on Yelp and is also stored in a database which is accessible by the event planning system. In some embodiments, the database stores all of the user's reviews. Similarly, instead of crawling through social network content or other content to find/analyze the content, in some embodiments, the content is stored/analyzed as the user inputs it. For example, a user's tweet goes on Twitter, but the tweet is also stored in a separate database (or parts of the tweet are stored such as parts parsed out based on analysis).

In some embodiments, the current mood or physical status of the person/people meeting is determined. The mood is able to be determined based on facial analysis using a camera, user input/selections (e.g., selecting "sad"), analyzing user input (e.g., parsing text of a recent social networking post to find keywords), and/or any other way. In some embodiments, mood information and other information is determined using security cameras. The physical status is able to be determined based on recent trip information (e.g., jet lagged from cross-country trip), based on date and occupation (e.g., early April is a busy/stressful time for CPAs due to tax season) and/or based on medical information (e.g., contact has a broken leg).

In some embodiments, the type of person/people is factored in to provide a suggestion. For example, if a person is adventurous, a different kind of cuisine is suggested often; however, if the person likes repetition, varying cuisines are not offered. The type of person analysis is able to include analyzing social network posts, determining the person is not negative often (e.g., does not write many negative reviews or "dislike" items), an input by the user, analyzing the person's food purchase history and/or likes/dislikes, and/or any other implementation.

In some embodiments, recent (e.g., within the past 3 days) meals of the people meeting is analyzed. For example, a log is automatically kept of meals of each user by the event planning system, and then this information is used. Furthering the example, if one user ate pizza the day before, then pizza is not suggested for today (unless a trend is determined (e.g., User X has eaten pizza two days in a row, five times previously based on meal history analysis)).

In some embodiments, personal information is analyzed such as a user's occupation, salary, bank account information, and/or any other relevant personal information. For example, a high-end restaurant is suggested for a wealthy professional, while a more reasonably priced restaurant is recommended for a college student. In another example, the bank account information is tracked and used to help the user budget meals and other items. For example, if the user wants to save money, the user is able to set a food budget of $X, and all restaurants that have average meal prices above that amount are eliminated from the possible recommendations. In another example, the budget information does not eliminate expensive restaurants automatically; rather, it is factored in along with other criteria (e.g., an exception because it is Valentine's Day, or based on who the user is meeting with such as a student meeting with his parents who will likely pay).

In some embodiments, the information is able to be from Internet of Everything devices such as smart toasters, refrigerators/freezers, irons, ovens, microwaves, blenders, thermostats, washing machines/dryers, and/or any other smart device. For example, a user has a centralized food/grocery list (e.g., digitally stored in the "cloud") which includes all of the food items in his house. When a smart device detects that an item is used (e.g., frozen pizza heated in microwave or user informs central storage by saying, "I'm eating ice cream now"), that information is able to be analyzed. Furthering the example, the information that a frozen pizza was heated in the microwave today is utilized to suggest something other than pizza for a meeting tomorrow. In another example, purchase information is analyzed (e.g., purchases from a grocery store).

In some embodiments, Internet of Everything devices include a camera/scanner and are able to determine the food based on an image/scan acquired. For example, the image is compared with food templates to determine what type of food is being prepared. In some embodiments, the Internet of Everything devices include a scale to weigh the food to determine quantity/calories and/or help determine the food item. In some embodiments, the Internet of Everything device include a RFID reader, bar code scanner, QR code scanner, bluetooth connection, and/or any other mechanism to determine the food and/or quantity of the food placed in the device. For example, a smart microwave has an RFID reader, and a food package has an RFID tag indicating the food product and/or nutritional/calorie information, which is read by the RFID reader. The microwave then sends this information to a cloud device, to the user's smart phone, and/or any other device, so that the information can be utilized when providing a recommendation. In another example, the device includes a bar code scanner which scans the bar code of the food product, so that the type of food is able to be used and analyzed when providing a recommendation.

In some embodiments, a smart cup/glass is able to be used to determine what the user is drinking which is then used to provide a recommendation. The smart cup is able to be implemented in any manner such as including a microchip which analyzes the color of the drink, sugar content of the drink, and/or ingredients of the drink to determine the drink. For example, the smart cup determines the user drinks beer on the weekend (the cup is able to record any kind of information such as date, time, content, quantity, number of refills, weight, class of drink, alcoholic/non-alcoholic, and/or any other information), so for a weekend event, a restaurant that serves beer is recommended. A smart bowl/plate/container is also able to be used to analyze food similar to the smart cup. A microchip is included on the bottom of the plate which analyzes the content placed in the plate, and the plate information is sent to a cloud device, smart phone, and/or other device to be analyzed when providing recommendation. In some embodiments, the smart cup and plate information is analyzed together or coupled in a database to provide recommendations. For example, based on analyzing the smart cup and plate information, it is determined the user only drinks beer when he is eating steak but never with pizza or pasta, so if an Italian restaurant is recommended, the beer aspect is given little or no weight.

In some embodiments, website visits/browser information/online search information is analyzed. For example, if a user searches for "seafood recipes," that information is able to be used to suggest a seafood restaurant or inquire if the user recently ate seafood to avoid recommending seafood again.

In some embodiments, successful places/venues/restaurants are tracked to have/conduct business meetings of particular groups. For example, a golf course café is a good place for attorneys to brainstorm personal injury lawsuits.

Additional information such as local offerings are able to be taken into account as well. For example, a group coupon (e.g., by Groupon® or Living Social®), where a discount is provided to a large group of people, but each individual person purchases a coupon, is taken into account. The group coupon is able to be one already purchased by one or more of the users meeting, or the group coupon is one that is currently available for purchase. For example, a data structure stores currently purchased group coupons by each user. Group coupons are able to be searched for. For example, group coupon sites/postings are crawled through, and utilized to make a recommendation. In some embodiments, the group coupons are analyzed during the analysis to make a suggestion, and in some embodiments, the group coupons are analyzed after a preliminary recommendation is made. For example, after it is determined (manually or automatically) to go to an Italian place for dinner, only Italian restaurants' group coupons are searched for. In another example, local deals such as happy hour are utilized. The local deals are able to be determined based on searching through advertisements or a data structure (e.g., database) storing local deals. In some embodiments, a person's use of group coupons is monitored and factored in. If a user does not use group coupons that are offered to him, then that has a weaker/lower weight when determining a recommendation. In some embodiments, restaurants with an available group coupon are placed at the top of a recommendation list and/or users are able to specify if group coupons are weighted and/or how much weight they are given.

In some embodiments, the additional information is analyzed to determine the type of meeting/get-together being planned. For example, is the meeting for the event a social meeting, a business meeting, a date, or another type of meeting? Determining the type of meeting is able to be performed manually (e.g., user selects the type of meeting) or automatically based on analysis of the information. For example, the meeting type is determined based on keywords in the communication (e.g., by searching for keywords such as "offer," "position" or "job" in an email or tweet), relationship of the contacts (e.g., applicant and potential boss, boyfriend and girlfriend), keywords/information on a social networking site, relationship status, date/time (e.g., on Valentine's Day), by detecting a resume by content/keyword/format analysis (e.g., as an attachment to an email), and/or any other way of determining the meeting type. Furthering the example, keywords are able to be compared with a source database, and a relationship status is able to be determined based on social networking information (e.g., by data mining information). By determining the type of meeting, a better recommendation is able to be made. For example, if it is determined that the two users are boyfriend/girlfriend meeting for Valentine's Day, a romantic restaurant is suggested as opposed to a different location for a business meeting. In another example, if it is cold, then patio dining with no heat lamps is not suggested.

In some embodiments, the current/predicted weather is analyzed. For example, if the weather prediction is 100% chance of rain, then golf is not suggested for that day. In some embodiments, user reactions to weather is analyzed. For example, if a user does not like to drive in the rain, then if it is currently raining, the user will likely not venture out or may wait until the rain stops.

In some embodiments, event planning of multiple contacts is compared. For example, a user wants to get together with Contact A, Contact B, and Contact C. Contact B is already planning an event with Contact D and Contact E. The information regarding the event with Contacts B, D and E is able to be utilized when event planning for the user and Contacts A, B and C. For example, if Contacts B, D and E are planning on or are likely meeting at 5 pm, then that time slot is not suggested for a meeting time for the user and Contacts A, B and C. In another example, if Contacts B, D and E are planning on meeting at 5 pm, and A and C want to meet up with B, the social networking information is able to suggest a meeting with all five (A, B, C, D and E). In some embodiments, potential conflicts are determined (e.g., that A and C do not get along with D and E) before suggesting the larger group meeting. In another example, calendar information of contacts is able to be shared to help avoid time/planning conflicts.

In some embodiments, the contacts are automatically determined based on social networking information. For example, User A is looking at dinner options, and User A has a small social networking group of dinner friends. The system automatically assumes the members of that group are the invitees for dinner and utilizes their information to make a recommendation. In another example, a user indicates (or it is automatically determined by keyword detection or other detection) a type of event (e.g., sushi for dinner), and the system determines contacts who have that interest in common (e.g., also like sushi) and automatically contacts those contacts or provides the contact information for the user to select who to invite. In some embodiments, additional information is also utilized to determine who to invite. For example, although Contact J likes sushi, she is 1.5 hours away, so she is not provided as a possible invitee. In some embodiments, the additional information includes health/medical information.

For example, if a user has a heart condition, a strenuous hike is not recommended for that user. In another example, if a user posted on a social networking page that he just sprained his ankle, then soccer is not recommended for that user. The health/medical information is able to be acquired in any manner and from any source such as medical records, social network posts, personal web pages, and/or any other source. In some embodiments, social networking information and/or other third party information is used for source information. For example, Restaurant X may not know or list all of its allergy information, but customers are able to post that information using social networking, and that information is able to be searched, retrieved and used for providing recommendations and alerting a user of allergy concerns. In some embodiments, the health/medical information includes food allergy/intolerance information. For example, if a user is allergic to peanuts, then a restaurant that has peanut shells on the floor or uses peanut oil for cooking is not recommended for the user. In another example, if a user has a gluten intolerance, then when a restaurant is recommended, a list of items on the menu that are gluten-free is also provided to that user.

In some embodiments, allergy and/or other health information is able to be used to alert a user when the user is physically at/near a business/restaurant. For example, if a user is allergic to peanuts, the user is alerted (e.g., on a health band, smart watch, smart phone) that he is about to enter a restaurant with peanuts on the floor. Furthering the example, the smart device communicates with a device (e.g., server, beacon, using NFC) within the restaurant providing allergen information. In some embodiments, sensors are used at and in a restaurant or other building such as on the door, table, and/or menu and the sensors/emitters provide information or to send information to a smart device. For example, a glass door is illuminated in red using LEDs within the door when a user with an allergy contained in the building approaches. Furthering the example, the door determines who the user is (via a camera and facial detection, smart phone communication with the door or another device, biometric analysis of the user's fingerprints as he grips the handle), then the user's allergies are compared (e.g., using database comparison) with allergens contained in the restaurant (e.g., user has peanut allergy and restaurant has peanuts on the floor), and based on the comparison (e.g., a match of allergy/allergen), a warning is provided to the user (e.g., door is illuminated red, audible warning). In another example, the smart device uses gps to determine the user's current location (e.g., address information) and using that information to look up the restaurant and any allergen information. The smart device is also able to provide allergen information/alerts (or other health information) about specific items at the restaurant and/or recommendations for the user at the restaurant. For example, based on the user's current location, a list of items at that restaurant which the user is/may be allergic to is provided to the user on the user's smart device.

In some embodiments, health information is acquired using a monitoring device which records the information and/or sends the information to a cloud computing device. For example, a smart phone implements an app which monitors/measures user information such as heart rate, steps taken, blood pressure, blood sugar, cholesterol, weight, height, and/or respiratory function. Any health monitoring/measuring/analyzing device is able to be used such as a health band, smart phone, smart watch, health watch, any other wearable health/medical technology, and/or any other technology. The health monitoring device is able to be used in conjunction with other information such as eating schedules, caloric intake information, exercise schedules, work schedules, foods to avoid, and/or any other information to be compared with other users' information.

Users are able to specify information to exclude. For example, a user is able to specify that restaurants with two stars or less on yelp.com will never be recommended. Further specificity is able to be implemented for inclusion and/or exclusion of events. For example, a user is able to specify to exclude all restaurants with two stars or less on yelp.com as long as the restaurant has at least five reviews. The reviews on review sites are able to be analyzed further as well. For example, keywords/phrases are able to be searched for such as "slow service," "overpriced" or "small portions" are phrases to search for when analyzing restaurants. In some embodiments, the keywords/phrases are utilized to generate an overall rating. For example, if negative phrases such as "overpriced" are detected, then a rating of the restaurant is reduced further. In some embodiments, users are able to specify further events to include/exclude. For example, a user indicates to exclude all restaurants with two stars or less, based on five reviews or more and if the phrase "dirty" is detected.

In some embodiments, song selections (e.g., using Pandora®) are analyzed and used to suggest concerts, music for purchase, clubs to go to, and/or any other items. For example, if a user provides a "thumbs up" for several rock groups, when a popular rock group is in town for a concert, the user is notified or that information is used to provide a recommendation.

In some embodiments, users specify which sources are used for the analysis. For example, a user indicates that his Facebook® page is usable but not his tweets for obtaining likes/dislikes and/or other relevant information.

In some embodiments, emails are analyzed. For example, a user has emailed several links to cat videos, so a recommendation of visiting a local animal shelter is able to be provided.

In some embodiments, the quality of the source is analyzed. For example, each source is given a quality rating. The quality rating is then able to be used to give different weights to information. Furthering the example, a user's online diary is given a quality rating of 10 on a scale of 1 to 10 as it provides specific, accurate information about the person's likes/dislikes. However, a random tweet may be given a quality rating of 3 because it may be a spontaneous reaction to something and not as well thought out. The quality rating is able to be determined in any manner (e.g., manually, automatically) such as by classifying content and/or any other way. For example, the number of times content is viewed and/or accessed by the user is able to indicate quality. For example, a diary which is accessed once a day has a higher quality rating than a single tweet which is never viewed.

In some embodiments, a timeline of events is used, or events are time stamped. For example, if a user indicates he likes pizza in a tweet, but that tweet is timestamped 10 years ago, that information is given less weight or no weight. For example, if another information source contradicts the old information, the old information is ignored or given less weight. Furthering the example, a user liked hamburgers 10 years ago, but in a blog posting, the user indicates that he has gone vegetarian; based on timestamps, the meat-based burger information is deleted/ignored or suggestions of vegan burgers are provided.

In some embodiments, the analyzed data is stored efficiently. For example, users who utilize the social networking event planning system often have their data stored on a faster device or a local device, while other users have their data stored on a slower device. In some embodiments, data that is more frequently accessed such as cuisine preferences/likes are stored on a faster device and data that is accessed infrequently is stored on a slower device. In some embodiments, information is cached for faster access. Frequently used data is stored on a faster device, and less frequently used data is stored on a slower device. Any information is able to be cached, not just common interest information.

In some embodiments, images (photographs) and videos are analyzed to make recommendations. The analysis of the images/videos is able to be performed in any manner such as detecting shapes, detecting logos, detecting text within the image, facial recognition, detecting a location, audio analysis and/or any other analysis that is able to determine content within an image or video. For example, an image is analyzed to determine who is in the image. For example, facial recognition is used to compare faces with a database. After determining the people in the image, the user's contacts are compared with the people in the image. If a person is not a contact of the user, the user is presented with the possibility of connecting with the person on a social networking site. For example, a picture is taken of User A and Person X, Person Y and Person Z. Person X and Person Y are already contacts of User A on Facebook®. However, Person Z is not a contact of User A. So, User A and Person Z are recommended to connect. In another example, an image shows a user with a beer in his hand, and based on analysis, that type of beer is recommended to the user for purchase and/or a bar/restaurant that serves that beer is recommended. Images/videos are also able to be analyzed to detect activities. For example, an image is analyzed, and it is determined that the user is hiking, so an additional hike is another recommended activity. Or an image is analyzed, and dancing is detected. Determining an activity in an image is able to be performed in any manner such as detecting objects within an image and using a database which contains activities and the objects for those activities. For example, an image with the objects: person, boots, backpack, trees, and dirt corresponds with hiking In some embodiments, captions of the images/videos are utilized in determining the activities. For example, a caption of an image says, "relaxing on the beach in Cabo," which indicates the person enjoys going to the beach.

In some embodiments, games and/or online games such as "Second Life" are analyzed to make recommendations. For example, if a user has a preference on the online game, the preference may equate to a real life preference. Further analysis is able to be performed as well such as determining that players who select to be "Ogres" on Game X typically like pizza and do not like vegetarian dishes. The analysis is able to be performed in any manner such as maintaining a database which includes users, their online gaming information including character types, and their real life personal preferences. Then, any trends that are determined using this analysis are able to be used to make recommendations to other users.

In some embodiments, exercise/diet information is able to be used in making recommendations. For example, information that the user recently ran for 45 minutes on a treadmill, the user is offered to eat a meal that does not provide more calories than were burned off. When a group of contacts is attempting to meet, all of the users and their diets/exercise routines are able to be taken into account to provide locations and/or menu options.

In some embodiments, a secondary search (or additional searches) based on a primary search is implemented when analyzing information. For example, in addition to searching for a type of cuisine, a secondary search for organic options within that cuisine is implemented. In another example, analysis of the owner of a restaurant (or other business), chef, supplier, free range, non-gmo, fair trade, political/personal beliefs of the owner/establishment, and/or any other items is implemented and used in making a recommendation. For example, if a user wants Indian food, but also wants non-gmo food, both aspects are able to be analyzed when providing a recommendation. In some embodiments, the search for Indian food occurs first, and then the non-gmo food search occurs second such that the results of the second search are limited by the first search, and in some embodiments, they occur simultaneously and the searches are independent.

In some embodiments, a user's driving style is analyzed in making a recommendation. The information is able to be received from the user's vehicle automatically. Trends are able to be determined to use for a recommendation. For example, users who drive quickly tend to prefer fast food over sit-down Italian restaurants.

In some embodiments, a brain wave sensor device (e.g., EEG or other sensor device) is utilized to determine cravings of a user. The brain wave sensor device is able to be embedded in the user, worn on the user (e.g., headband, watch or glasses) and/or implemented in any other manner. The brain wave sensor device is able to perform brain wave analysis in real-time or non-real-time. The brain wave sensor device analyzes brain waves or detects other changes in the brain based on cravings and/or moods of the user. For example, patterns are monitored for and detected which are then used to learn and determine which pattern relates to which type of craving or desire. The information is then able to be used to recommend a specific cuisine and/or meal. In some embodiments, content (e.g., images/videos/smells/text/audio) is shown/provided to a user (e.g., on the user's smart phone or another device), and the brain waves are analyzed while the content is shown. For example, an image of a traditional Chinese food dish is displayed, and the user's brain waves indicate a like of the dish, while an image of seafood triggers brain waves which indicate a dislike of the dish. In some embodiments, thoughts are downloaded from a user's memory to a hard drive or other physical memory using a microchip which is able to receive electrical pulses from a user's brain and convert the pulses to information readable/storable by the physical memory, and are then the downloaded information is able to be searched/analyzed.

In some embodiments, a microchip is utilized to analyze a user and provide a recommendation. In some embodiments, the microchip is embedded or not embedded. In some embodiments, the microchip is surgically placed in a user. The microchip is able to perform body (or bodily) fluid analysis in real-time or non-real-time. The microchip detects chemical or other changes which influence food preferences (e.g., blood sugar, proteins, nutrition levels, oxygen saturation, mercury such as related to fish consumption, other chemicals/substances). The microchip is also able to detect the user's body temperature such that a lower body temperature may suggest a warm beverage/food would be preferable to the user. In some embodiments, the microchip analyzes a user's sweat (e.g., salinity in the sweat) to provide a recommendation. For example, a user with a high salinity concentration may prefer a salad over a salty pizza. In another example, the indication of high salinity may indicate the user prefers salty foods, so additional salty foods are recommended. Prior eating history and/or health history are able to be used to determine the correlation between the body fluid analysis information and the recommendations. In some embodiments, the analysis incorporates health/diet information to encourage the user to eat healthier. For example, a low sodium choice is recommended for a user with high salinity sweat. In some embodiments, the microchip analyzes a user's blood to determine recommendations. For example, if high cholesterol is detected, healthy dishes are recommended. In some embodiments, the microchip analyzes the user's fat, intestinal product/output, urine and/or other fluids/anatomy to determine what the user has recently eaten and how the user's body responded to what was eaten. In some embodiments, the microchip analyzes the user's brain waves. In some embodiments, the microchip includes or is part of another device which includes sensors and/or other components. For example, a watch includes a sensor/microchip to analyze sweat which then provides recommendations to the user. Furthering the example, the watch includes a sensor or other device which uses optical detection of sweat (e.g., using LEDs and a photo detector), capacitive humidity sensors, a pH sensitive patch, and/or any other sweat capturing/analyzing features. For example, a strip of sweat analyzing material is coupled to or incorporated with the watch or other device which provides sweat information based on the reaction of the sweat and the sweat analyzing material, and then the information is analyzed by another device such as a mobile phone. In another example, an electrical current (and the appropriate hardware configuration) is used to measure the salinity of the sweat. In some embodiments, the watch, clothing or other device communicates with another device (e.g., the cloud and/or the user's smart phone) to generate and/or provide a recommendation. In some embodiments, clothing is utilized to analyze the user. For example, clothing including one or more sensors/monitoring devices analyzes the user's body temperature, sweat, the temperature outside, the user's brain waves, and/or any other information to provide a recommendation. The clothing is able to communicate with other devices such as servers and smart phones as well. The clothing is able to be any clothing, such as a hat, a headband, a wristband, sneakers, a shirt, a jacket, pants, underwear, and/or anything else. In some embodiments, a removable/attachable garment piece with one or more sensors/monitoring devices is able to be implemented. The garment piece is able to be worn over or under clothing. The garment piece is able to be attached to and removed from the clothing in any manner (e.g., glue, Velcro® (hook and loop), iron-on, stitching, snaps, zipper, button). Similarly, jewelry such as a watch, ring, bracelet, earrings or necklace, is able to include sensors or other devices to analyze the user. Glasses, sunglasses, contact lenses, hearing aids, braces, and/or any other items are able to include sensors or other devices to analyze the user. In some embodiments, another device is used to analyze the user such as a breathalyzer, a sensor/microchip in/on a cup or glass, and/or any other device to analyze the user. In some embodiments, nanoparticles are utilized to analyze a user and provide a recommendation. The nanoparticles are able to perform body fluid analysis in real-time or non-real-time. The nanoparticles detect chemical or other changes which influence food preferences (e.g., blood sugar, proteins, nutrition levels, oxygen saturation, other chemicals/substances). The nanoparticles are also able to detect the user's body temperature such that a lower body temperature may suggest a warm beverage/food would be preferable to the user. The nanoparticles are able to detect other body aspects such as amount of fatty tissue, heart rate, illnesses/allergies, muscle activity, intoxication, and/or any other body/health information. In some embodiments, the nanoparticles are included within a tattoo, in lotion, chapstick and/or any other implementation. The microchip, brain wave analysis device, and/or the nanoparticles are able to be configured to communicate with one or more other devices (e.g., transmit/receive information to/from a user's smart phone and/or the cloud). In some embodiments, a device implements audio/video/ image analysis. For example, a device includes a camera with a microphone to capture a user's reaction to things the device sees and/or hears. Furthering the example, if a user cries when they hear fireworks, this reaction is able to be recorded. For example, a database includes a column for event (e.g., fireworks or loud noise), a second column for reaction (e.g., crying), and a third column for recommendation (e.g., −10 points for loud events such as fireworks show or such events being completely eliminated as a possible recommendation for the user). In another example, the camera is able to recognize different facial expressions (e.g., smile or frown) or other expressions and record information related to the response. In some embodiments, multiple cameras are utilized (e.g., one facing out and one facing the user's face), so that it can be determined what the user is reacting to. For example, the user is smiling while eating ice cream, so the first camera recognizes the ice cream, and the second camera recognizes the smile. In some embodiments, cameras are able to communicate with each other or other devices to minimize the number of cameras on the user. For example, a web cam coupled to a user's computer monitors the user and his reaction, and sends this information to the cloud or the user's smart phone. In some embodiments, additional or other senses are able to be monitored (e.g., touch using a tactile sensor/monitor, smell using an olfactory sensor). Other monitors are able to be included, such as a pulse monitor, pedometer, and/or gps tracker. Movements by a user such as head nods, head shakes, cringing, shrugs, and/or other body reactions/movements are able to be recognized (e.g., using video capture/analysis and/or motion sensors) and utilized. In some embodiments, the reactions and/or other acquired data are used to provide suggestions, recommendations, alternatives, store results as favorites depending on the time of day, month, season, search parameters, and/or any other analysis. In some embodiments, a thin layer of material is able to be worn/placed on a user's lips or teeth which monitors/analyzes fluids, foods, lip-smacking, curvature of the lips and/or any other lip/teeth information and sends the information to another device for further processing. In some embodiments, a device (or devices) includes multiple technologies (e.g., brain wave detector, sweat analyzer and pulse monitor in one item).

In some embodiments, a camera device, a smart device and/or a smart display is able to monitor and analyze specifically what the user is actually watching/viewing. For example, if a user is viewing a web page, but only reads the top portion of the web page, the device is able to detect the portion of the web page that the user actually reads (e.g., recognize only the pixels displayed on the screen), so that the event planning system does not mistakenly interpret the user's viewing/searching habits. In another example, the event planning system determines how long a user is viewing something. For example, if a user views a web page for a long time (e.g., equal to or above a time threshold), it is able to be assumed the user read the web page thoroughly, and if the user views the web page for a short time, then it is assumed that although the user visited the page, the user did not read the web page well. Similarly, the scroll speed of a page is analyzed (e.g., fast scrolling equates to skimming or not reading, and slow scrolling equates to thorough reading).

In some embodiments, a user's dietary restrictions are analyzed when making a recommendation. For example, if analysis of the user's schedule determines that the user has a colonoscopy scheduled in a week, the user is warned to avoid seeds which could interfere with the test, and food/restaurant recommendations are made which comply with the dietary restrictions.

In some embodiments, recommendations are based on brands the user purchases. For example, the type of car, the kind/brand of clothing, and/or other items. Furthering the example, based on research, it has been determined that people who drive Toyota Priuses tend to prefer vegetarian meals over burgers, thus this information is able to be used when recommending a restaurant or deciding an activity (e.g., hike versus going to the rodeo). Determining the user's purchases is able to be performed in any manner such as analyzing a digital wallet, shopping cart, credit card information, any other digital purchase information, social networking sites (e.g., Pinterest, Instagram or Facebook®), and/or any other information. For example, analyzing includes determining the user by face recognition in an image and determining a brand of item in the image using imaging technologies.

In some embodiments, brand connections are utilized in making a recommendation. For example, a user prefers Cola X over Cola Y, and certain restaurants serve Cola X and other restaurants serve Cola Y. Depending on the weighting provided to the cola preference, it is possible to eliminate the restaurants that offer Cola Y, or a smaller preference is given to restaurants that serve Cola X. The preferences of the users are able to be determined based on photo analysis (e.g., detecting a Cola X can in the user's hand in multiple images where the more detections provides a greater weight), based on input by the user (e.g., manually selecting Cola X and giving it a top priority), and/or any other manner.

In some embodiments, the variety of music a user prefers is able to be analyzed and used to make a recommendation. For example, if a user likes pop, rock, alternative, country and jazz, the user has a varying taste in music and likely has a varying taste in food. Similar to the adventure rating described herein, a user is able to have a variety rating. For example, a user who likes 8 different genres of music is given a variety rating of 10 (out of 10), while a user who only likes 1 genre of music is given a 1. Determining the user's likes of music is able to be determined in any manner such as analyzing an online music playlist, analyzing the user's downloaded songs, analyzing concerts attended and/or any other analysis. The variety rating is then able to be used to when providing a recommendation for anything such as restaurants, foods and/or activities. Determining the user's music preferences is able to be performed using automatic content recognition to recognize a song or video. The automatic content recognition implementation is also able to be used to determine the amount/percentage of the song the user listens to. For example, an automatic content recognition implementation listens to the music the user listens to on a computer, on the radio, on the television, and any other device, and recognizes the songs that the user listens to, and determines that the user listens to country music and changes the station when rock music is played. The automatic content recognition is able to be used to determine cuisine preferences as described herein or recommend other activities as well such as a concert or movie.

In some embodiments, cuisine preferences or activities are recommended based on music preferences. For example, if the user prefers country music, then steak and barbecue restaurants are recommended for the user. The analysis to determine music preferences is the same as described herein.

In some embodiments, a recommendation is made based on GPS or other tracking including historical tracking. For example, based on analysis of GPS tracking of the user for the past month, the user drives near Restaurant X at 6 pm often. This information is able to be used to recommend that location at that time in the future. In another example, current and/or previous activities are able to be determined based on GPS information. Furthering the example, GPS coordinates of a user's device match with coordinates for a hiking trail, so it is determined that the user enjoys hiking based on the GPS coordinates.

In some embodiments, patterns such as activity patterns or food patterns that the user is aware of or unaware of are used to generate a recommendation. For example, every month, a week before the user's menstrual cycle, the user craves chocolate, so for an event during this time period, this information is factored in. Furthering the example, it is determined that the user is one week before her period, so a recommendation is made for a restaurant that is near a dessert place that has chocolate cake. The user's cycle is able to be determined in any manner, for example, by the user inputting her cycle, based on social networking information analysis, based on personal medical information, and/or any other manner. In another example, a user exercises every morning at the gym, so the system is able to utilize that information to recommend a breakfast place near (e.g., within 1 mile or 5 miles—could be a user-selected distance) the gym for an event around that timeframe. Patterns are able to be determined in any manner, for example, by storing historical data and locating matches of repetitive behavior. Furthering the example, GPS coordinates of the user are stored with timestamps for each day, and if the coordinates and timestamps match up for several days, a pattern is able to be determined. The habits are able to be seasonal. For example, in winter the user eats more comfort food, and in the spring, the user diets. In another example, the user travels to the mountains/snow only in winter, and recommendations are able to be provided for restaurants in the mountains. In another example, the user enjoys holiday specials such as a peppermint milkshake around Christmas, so that when Christmas is approaching, the user is reminded of the peppermint milkshake, and this information is able to be factored in when recommending an event. The habits are also able to be based on the day of the week. For example, it is determined based on previous purchases, that the user always purchases a coffee from Store X on Friday. Habit information is able to be used in conjunction with the to-do lists described herein. For example, if it is known that the user goes to Store X on Friday for coffee, any to-do list items that are near Store X are able to be reserved until Friday and recommended for then.

In some embodiments, a user's to-do list (or other to-do items) is analyzed and the locations of the to-do list are determined. The locations of the items on the to-do list are utilized in generating a recommendation. For example, the user needs to purchase cat litter which is in San Jose, so a recommendation for lunch is in close proximity (e.g., within 1 mile or 5 miles—could be a user-selected distance) to the cat litter store. In some embodiments, multiple users' to-do lists are analyzed and compared to best enable all of the users to complete their to-do lists as well as meet up. In some embodiments, the to-do items are given a weighting (automatically, manually or a combination of both), such that to-do items that are not as important are not given as much weight when making a recommendation. Users are able to mark items using a color-code scheme (e.g., red items should be done very soon, yellow items should be done next and green items can wait a while) to indicate their importance/urgency. In some embodiments, to-do items below an importance threshold are ignored when making a recommendation. In some embodiments, users rank the to-do items, such that the item at the top of the list has the highest priority, and the event planning system performs analysis to attempt to remove items closer to the top before items closer to the bottom of the list. In some embodiments, the to-do items are generated automatically. For example, a scale (capable of communicating with a network and/or smart device) weighs the stored cat litter bag, and when the weight drops below a threshold, the item is added to a to-do list (e.g., buy cat litter within 1 week). In some embodiments, the event planning is determined first, and to-do items are added on afterwards. For example, an event such as dinner with friends is recommended and scheduled, and then it is determined if any of the to-do items are in close proximity to the event, along the way to the event, and/or any other relevance to the event. Furthering the example, a dinner is scheduled in San Jose based on the recommendations provided by the system, and the user is presented with the option to pick up the cat litter which is near the restaurant. The to-do lists are able to be acquired in any manner, for example, input by a user on a smart phone, imported from another app, downloaded from the cloud, and/or any other implementation. In some embodiments, items the user wants "to do" are not on/in a to-do list but are analyzed and utilized when determining a recommendation. In some embodiments, navigation directions are automatically generated for the to-do items and the recommended event. In some embodiments, a user selects specific to-do items to be analyzed when performing the recommendation analysis. An exemplary implementation of utilizing a to-do list with the event planning system includes: generating/locating a to-do list, analyzing the items on the to-do list including determining importance of the items and/or location of the items, performing the event planning analysis described herein (e.g., determining common interests and analyzing additional information), and generating a recommendation based on the to-do information and the event planning analysis. Generating the recommendation based on the to-do information and the event planning analysis is able to be performed in any manner, for example, Event A receives a base recommendation score of 85 based on proximity to users, cuisine preferences and traffic, Event B receives a base recommendation score of 84 based on the same elements, but Event B receives a bonus recommendation score of +3 because one of the contact's to-do items is near Event B but not near Event A, so the total recommendation score of Event B is 87.

In some embodiments, animal/pet preferences are utilized to generate a recommendation. The pet preferences are able to be determined in any manner such as input by the user's owner (e.g., by selecting choices on a GUI on a smart phone), input by the pet (e.g., using paw, beak, tongue), determined by analyzing images/videos of the pet, analyzing social networking information, and/or any other manner. For example, the user posts a photo of her dog playing in the ocean. Using photo analysis, it is able to be determined that the dog is the user's pet, the dog is in the ocean, and any other information. For recommending an event, locations with beach access are able to be given additional points. Or a dog-friendly restaurant is recommended and preference is given to restaurants near a beach. In another example, social networking information is analyzed. The social networking page of a user and/or the user's pet (e.g., assuming the user generated a social networking page for the pet) are able to be crawled for information such as images/videos/text which indicates food/activity preferences. Furthering the example, keywords are searched for on the pages to detect preferences.

In some embodiments, kids' preferences are utilized to generate a recommendation. For example, a user is planning a vacation, so the user's preferences are analyzed, the user's spouse's preferences are analyzed, and the user's children's preferences are analyzed to make recommendations that are enjoyable for the entire family. In some embodiments, children's preferences are stored in a separate database and/or given less weight than the parents' preferences.

Any language analysis is able to be performed when analyzing social networking pages such as keyword analysis, natural language analysis, and/or any other analysis.

In some embodiments, information is acquired using an e-wallet mechanism; for example, monitoring purchases made electronically. For example, a user uses his smart phone to purchase coffee; that information is able to be stored and/or analyzed. Analysis of the smart phone purchases enables the recommendation system to easily determine what the user is doing and/or purchasing and where/when. Furthering the example, the smart phone purchase analysis will determine where the user travels, what foods the user purchases and when, what activities the user pays for, when/where purchases are made, and/or any other information.

In some embodiments, information acquired using an augmented reality device is analyzed and utilized in making a recommendation. For example, GPS information from the device is acquired. Image data acquired using a camera of the augmented reality device is able to be analyzed to detect items, locations and/or any other information. For example, a user wears a head-worn glasses-type device which detects that the user is eating a bowl of spaghetti on Tuesday at 7 pm. The images are able to be matched with templates and/or any other method. The augmented reality device is also able to listen to conversations and/or other audio for analysis. For example, the augmented reality device detects the user saying, "I don't like Italian food," so it automatically indicates that Italian food is an undesirable cuisine for this user. The augmented reality device is also able to use voice identification to ensure the quotes are attributed to the appropriate people/entities.

In some embodiments, recommendations are based on quests/goals of one or more users. The quests/goals of the user are able to be generated manually or automatically. For example, User A inputs that he wants to visit every bar in San Francisco with a Yelp.com rating of 4 stars or above. When generating a recommendation, this goal/quest is taken into account by giving priority (e.g., extra points) to bars with the appropriate rating that the user has not attended yet. The user is able to indicate how much of a priority the quest is which affects the weight of the quest. For example, if the quest is a high priority, then more weight is given to bars with the appropriate rating. A quest is able to be specifically indicated (e.g., walking 50 miles in a month) or generic (e.g., lose 5 pounds). For example, walking 50 miles is only accomplished by walking 50 miles; however, sub-quests or steps are able to be recommended/utilized to lose 5 pounds. For example, the user is recommended to eat smaller meals, exercise more (or even more specifically, what specific exercises should be done and when), and/or any other recommendations. In some embodiments, multiple quests are taken into account (e.g., quest for User A and quest for User B). The quests are able to be for the same person or different people. The quests are able to be related or unrelated. An example of related quests is walking 50 miles in a month and losing 5 pounds. An example of unrelated quests is walking 50 miles in a month and getting a promotion. An example of an automatically generated quest is: it has been determined that the user has climbed Mount Elbert, Mount Evans, and Pikes Peak, which the event planner determines are all peaks of Colorado above 14,000 ft, so the event planner recommends a quest of climbing all of the peaks. For example, after detecting a trend, future events related to that trend are recommended. For example, the GUI is able to present a question, "I noticed you have conquered 3 peaks above 14,000 ft, would you like a quest involving the rest of the peaks above 14,000 ft in CO?" The user is then able to accept or reject the quest. In some embodiments, when a quest is accepted additional recommendations are provided based on the quest. For example, as part of the quest to climb the peaks, a user is provided recommendations of trail maps, books and/or equipment to purchase for hikes/climbs that are more difficult than the ones the user has already done such as Capitol Peak. In some embodiments, warnings and/or other preparatory information is provided. In some embodiments, users are able to generate quests (or challenges) for other users. For example, User A challenges User B to lose 5 pounds or who can lose more weight. The event planning system is able to track the users' weights and/or integrate with another system which monitors weight information and/or other information. In some embodiments, job-related quests are able to be generated. For example, a user sets a quest of finding a job that offers stock options. Another example is setting a series of goals such as finding a job as a secretary, then a job as a paralegal (including the side quest of getting a paralegal certificate), and a job as an attorney (including the side quests of graduating law school and passing the Bar). Yet another example is becoming a manager within 15 years. The level of detail specified in the quest is able to be broad or specific. For example, although the user broadly selects/specifies becoming a manager, the specific steps of: getting great reviews each year, demonstrating leadership skills, talking with the right people, earning an MBA, and/or any other steps to become a manager are provided/analyzed by the event planning system as steps to succeed in the quest. The event planning system is able to provide recommendations for each step, for example, recommending the user to attend Conference Z where the user's upper-level management is the host, so that the user may introduce himself and discuss his aspirations. Specific information is able to be provided to the user such as what to do, who to talk with, if the user is on the right track, what improvements need to be made, which classes need to be taken or more generic information is able to be provided. The information is able to be gathered/generated in any manner such as using templates of career paths, analyzing the company information, analyzing the social networking information of the company/employees, analyzing specifically-generated tools which indicate how to succeed in a quest such as becoming a manager.

In some embodiments, items to be shared/reused are analyzed to make a recommendation. Users are able to specify items that they want to get rid of and/or are willing to share with others. For example, User A has a tricycle, a stroller, and other baby toys that she no longer wants. Users are also able to specify items they want. For example, User B, who just had a baby, specifies that she is looking for a stroller and baby toys. When recommending User A to connect with another user, this information is factored in, along with the other information as described herein such as common interests and additional information. For example, items to be shared are stored in a database, and items users want are stored in a database, and similar to comparing likes of users, items to be shared are compared with items users want. Furthering the example, if a user is sharing an item, and a contact wants that item, then the recommendation score for those users is increased. In some embodiments, the items are grouped or put into classes for determining if a share matches a want. For example, furniture items are a group, baby items are a group and automotive items are another group, and the groups are able to be compared. The item share information is able to be used in recommending contacts who know each other to get together and bring the items. The item share information is also able to be used in recommending contacts to connect and/or attend an event together either anonymously or not anonymously. The items to be given or received are able to be input in any manner such as selecting the items on a list, automatically determined by crawling/analyzing website (e.g., craigslist) postings, social networking posts, and/or receipt information, and/or automatically generated based on personal events such as determining the user recently had a baby and automatically determining the user likely needs a stroller or will need baby shoes. Similarly, expertise/knowledge is able to be analyzed when making a recommendation. For example, User A has recently developed an interest in Chess, so the information that a contact has expertise in Chess is analyzed when calculating a recommendation. Furthering the example, User A is informed that Contact C has been playing Chess for 15 years online when they attend an event together. In some embodiments, a special icon is indicated on a GUI when an item or expertise is to be shared, so that the user knows an item is going to be exchanged. In some embodiments, the icon or other graphical representation is able to be selected to provide more information such as a picture and/or text description of the item. In some embodiments, the event planning system coordinates value exchanges such that if User A is giving an item valued at $20, User B also gives an item valued at $20.

In some embodiments, comparison shopping is implemented for determining a recommendation. For example, two restaurant recommendations are determined based on likes, traffic and the other analysis. However, the items on the menu are compared, and Restaurant A provides a better price than Restaurant B. So, Restaurant A is recommended ahead of Restaurant B.

In some embodiments, information in the "deep web" is utilized for generating a recommendation. The deep web is world wide web content that is not part of the standard surface web that is indexed/visual to standard search engines. Information in the deep web is able to be gathered in any manner such as utilizing specialized crawling systems or specialized software for locating and/or accessing the deep web information.

Any combination of the additional information analysis is able to be used for generating a recommendation. For example, in a simple implementation, only traffic information is analyzed to generate a recommendation. In a more complex implementation: likes, dislikes, current/predicted traffic conditions, current/predicted wait times, mood, current/future locations of contacts, diet, adventure rating, coupons, type of event/meeting, current/future weather, health, music preferences, gaming, brain wave analysis, microchip analysis, purchases, searches, tracking, patterns, to-do items, augmented reality, employment information, travel plans, pet preferences, kid preferences, items to share/give/receive, quests, real-time analysis, learning, parallel analysis, reactions, comparison shopping analysis, nanoparticle analysis, deep web analysis, and/or any other factors are analyzed to generate a recommendation.

In the step 108, a recommendation is made. The recommendation is made by analyzing the information in common and/or additional information. For example, Contacts A, B and C all like pizza, and a pizza place with high user reviews is 10 minutes away from each of them, so that pizza place is recommended. In another example, Contacts A, B and C all like pizza and burgers. But, the nearest pizza place has a 30 minute wait, and a second nearest pizza place was given one star by Contact B in a yelp.com review. A burger place that has been "liked" by Contact A is five minutes from Contact A and 10 minutes from Contacts B and C because of traffic. In this example, the burger place is recommended.

In some embodiments, computations are performed based on the common interests and additional information to generate a recommendation. For example, the user is trying to find a restaurant to meet at, then only restaurants that provide the cuisine common to the contacts' interests are utilized. Then, of those restaurants, each restaurant receives five points for each star it has received on a review website such as yelp.com (or the average of several review sites). Each restaurant also receives five points for being within five miles of all of the contacts, three points for being within 15 miles of the contacts, and one point for being over 15 miles but less than 30 miles of the contacts. Points are also added or subtracted depending on wait times. Any other computations are able to be performed using the analysis such as added points if a contact has a group coupon, if a contact has previously "liked" a place, negative points if a contact has recently eaten that cuisine or at that restaurant, and/or any other factor/computation. In some embodiments, the computations are narrowed by eliminating possibilities. For example, the possible restaurants for a restaurant are limited to only the restaurants within 20 miles of a user or the user and contacts.

In an example, Restaurant A, Restaurant B and Restaurant C are three restaurants within 20 miles of User W who wants to eat with Contacts X, Y and Z. Additionally Restaurants A, B and C all have food that W, X, Y and Z like and have not eaten too recently. Restaurant A has received an average of 5 stars on 3 review websites, so 5×5 points=25 points. Restaurant A is also within five miles of W, X, Y and Z, so that is an additional 5 points. However, there is very bad traffic from Contact Z's current location to Restaurant A, and there is a long wait at Restaurant A. Since the traffic and the long wait do not compound the delay, that is only −5 points. Restaurant A has an available group coupon for purchase which is +3. Restaurant B received 4.5 stars on 3 review sites, so 4.5×5 points=22.5 points. Restaurant B is 10 miles from W, X, Y and Z, so 3 points, and there is no wait or traffic for Restaurant B, and W has previously purchased a group coupon for Restaurant B, so +10. Restaurant C has 5 stars on 3 review sites, so 5×5 points=25 points. Restaurant C is within five miles of W, X, Y and Z, so that is 5 points, but there is a long wait which is −5 points. In this basic example, Restaurant A=25+5−5+3=28 points; Restaurant B=22.5+3+10=35.5 points, and Restaurant C=25+5−5=25 points. Therefore, Restaurant B is recommended, or if a list is provided, Restaurant B is first, then Restaurant A and then Restaurant C. In some embodiments, the recommendation scores of the possibilities are presented to the user.

In some embodiments, priority is given to certain data. For example, a weighting scheme is utilized such that the quality of a restaurant is given more weight than the proximity of the restaurant. Furthering the example, a 5-star restaurant that is 15 minutes away is selected over a 4-star restaurant that is five minutes away. In some embodiments, the weighting scheme is determined by one or more users (e.g., a single user or a group of users agree on a weighting scheme). In some embodiments, the weighting scheme is learned and automatically generated. For example, if a recommendation is ignored frequently, the system does not provide that recommendation or attempts to use a different weighting scheme to recommend something else. In some embodiments, the weighting scheme is set by another (e.g., app developer). In some embodiments, extra weight is given to a contact. For example, if the event is to celebrate User V's birthday, User V's preferences are given full weight (and other contacts are given no weight), or User V's preferences are given three times as much weight as the other contacts. In some embodiments, extra weight is given randomly to one or more of the contacts. In some embodiments, the contacts are informed of the extra weight or not.

In some embodiments, alternative transportation options are factored in when making a recommendation. For example, a contact does not want to drive, so an event near a train station or within walking distance for that user is determined. In another example, carpooling is factored in when making a recommendation. In some embodiments, the event planning system communicates with a car service (taxi, Uber) and/or hotel service (e.g., hotels.com, airbnb.com) to arrange for transportation/lodging.

In some embodiments, the event planning system communicates with an automatic gift recommendation generator. For example, a gift idea is generated before the event based on the event and/or preferences of the gift-receiver (e.g., pirate puzzle for pirate-themed party) or an appropriate "thank you" for a mentor based on hobbies or interests of the mentor. In some embodiments, multiple implementations of the social networking event planning system operate (e.g., in parallel) to provide recommendations. The implementations are able to be user-generated, computer-generated and/or developer-generated. For example, a user specifies that he wants to give less weight to review site ratings and gives heavy weight to the price of the restaurant, but a computer-generated implementation gives heavy weight to review site ratings and minimal weight to the price, so these implementations may provide different recommendations. In some embodiments, both recommendations are provided for the user to compare. In some embodiments, the selections of the user are used to learn and improve the computer-generated implementation. The event planning system is able to learn in any other manner as well, such as by analyzing approvals of recommendations and/or analyzing other input by users.

In some embodiments, the recommendation is determined by the process of elimination. For example, if a restaurant is the target event, then any restaurants not matching the cuisine in common are eliminated. Then, restaurants with a review below three stars out of five are eliminated. Then, restaurants that are farther than 15 miles are eliminated. The process continues until a manageable number (e.g. below a threshold) of restaurants remain. In some embodiments, a user sets the thresholds for the eliminations, and in some embodiments, the thresholds are automatically determined and modified to reach the desired number to provide a recommendation. In some embodiments, events with a recommendation score (e.g., score determined from tallying likes, dislikes, traffic, and other items) below a threshold are eliminated. In some embodiments, events with a recommendation score below a first threshold are eliminated, then the threshold is increased to a second threshold, and events with a recommendation score below the second threshold are eliminated, and the process repeats by increasing the threshold and eliminating events until a specified/desired number of events remain.

The recommendation is able to be displayed in any format. In some embodiments, the recommendation is sent to all of the contacts meeting (or potentially meeting), and in some embodiments, the recommendation is only sent to a single user (e.g., the user searching for a meeting place). In some embodiments, the recommendation is displayed in a list form. In some embodiments, the users are able to vote using the list (e.g., by tapping the screen on a selection in the list). Furthering the example, a list is provided with five restaurants for seven friends to choose from, and a countdown timer is provided as well. The list is sent to each user's device (e.g., smart phone), and a countdown timer is displayed showing 60 seconds and counting down to zero for a user to select. If each user selects an option, then the results are tallied, and the selection with the highest score is selected. If a user does not make a selection, then his potential selection is either made using a randomizer to randomly select a choice, or his potential selection is ignored. In some embodiments, the selection process includes ranking the options (e.g., 1, 2, 3, 4, 5), and the rankings of each user are used to calculate the final selection. After a final selection is determined, directions to the selection are provided or a GPS destination is set and a route is calculated, a calendar appointment (with reminder) is generated, and/or a reservation is made (or the location is called to make a reservation or a website for the user to make a reservation is displayed). In some embodiments, additional information is provided such as a menu, food recommendations (from the menu), and/or any other information.

In some embodiments, a random recommendation is made. For example, similar analysis is performed as described herein; however, instead of providing a list of choices or only presenting the top choice, the five (or other number) best options are determined, and of those five, one is randomly selected.

In some embodiments, a suggestion is recalculated if one or more contacts decline an invitation or cancel. For example, common interests were found for the initial group of four contacts, but if one of the contacts cancels or rejects the event, then common interests are determined for the group of three remaining (and/or other analysis is performed). Similarly, if the location of the fourth contact was used in selecting a restaurant, that information is no longer needed, and a new restaurant may be determined based on the locations of the three remaining.

In some embodiments, a suggestion includes more than a single event. For example, the event is able to include multiple periodic events or sequential events. For example, based on the analysis, golf is recommended for the morning, followed by a burger place for lunch, then hiking and dinner at a French restaurant. In another example, quarterly meetings for board members are scheduled. In some embodiments, elements of the multiple events are factored in to make a recommendation. For example, to plan dinner and a movie, the location of the theater is utilized, and restaurants near the theater are given priority over restaurants further away. Additional information is able to be utilized as well such as times of the movies and available reservations at the restaurants. For example, if a recommended movie is playing at 8 pm, and the only available reservation at Restaurant Z is 8:15 pm, then the two are not recommended together. The system either searches for a different movie, theater or restaurant to recommend. In some embodiments, different events are able to be approved by the user separately. For example, the movie at 8 pm and the Restaurant Z reservation at 8:15 pm are provided to the user for the user to select only one, and then the event planning system performs additional analysis to find the second event. For example, the user selects the movie at 8 pm, and the event planning system searches for reservations at restaurants near the theater that do not conflict with the 8 pm movie time.

In some embodiments, the social networking event planning is able to be used for future planning. For example, during the day, a user plans an event for the evening, and instead of the contacts' current locations, the locations of where they will be in the evening are taken into account. Furthering the example, Contact B is currently at home, but in the evening, he will be at school (based on his online accessible schedule) which is 15 miles north of his home, so that location is utilized when computing a recommendation for dinner.

In some embodiments, the social networking event planning system is able to be used to recommend for users to go to the movies or stay home and what movie or programming to watch/rent. The analysis is able to include previously/recently watched movies (e.g., do not recommend a movie recently watched), movie preferences (e.g., action versus comedy), actor/director likes/dislikes, movie interests in common (e.g., both users liked Movie X), movie times, current movie locations, current locations of the users, sold out information, screen size of where the movie is playing, reviews/ratings (e.g., using IMDB or other rating sites) of the movies (in some embodiments, only reviews/ratings of users with similar interests as current users are used) and/or any other relevant information. For example, two contacts want to see a movie but are unsure which one to select. The social networking event planning system determines that both contacts like action movies based on previously watched movies, and that there is a movie theater five minutes from Contact A and 15 minutes from Contact B based on traffic with an action movie playing in 30 minutes, so that movie is recommended.

In some embodiments, the analysis includes determining where people are to recommend the user attend that location. For example, a user wants to watch a college football game at a sports bar and wants to be with alumni from the same school. Using location information of the people and/or social networking information, a user is able to determine which sports bar to go to.

In some embodiments, an adventure rating is generated for each user. The adventure rating is based on the number and/or variety of restaurants, cuisines, and/or activities liked or disliked. For example, if a user likes 29 out of 30 different cuisines, that user has a high adventure rating. The adventure rating is able to be used to determine a recommendation. Furthering the example, more varying recommendations are provided for users with high adventure ratings.

In some embodiments, a user is able to provide a recommendation, and the social networking event planning system is able to analyze the recommendation based on the analysis and provide additional information such as approval or disapproval of the recommendation or a better recommendation.

In some embodiments, multiple recommendations are made and displayed in a list form, chart form, tile format, or any other form/format.

In addition to or instead of suggesting an event, other aspects are able to be suggested. For example, food selections at a specific restaurant are able to be suggested (e.g., based on previous user reviews, personal preferences of the user and/or allergies of the user). In another example, clothing recommendations are able to be made by taking into account the location for the event, dress code for the event, type of event (e.g., hiking), what the other party is wearing, what clothing is available (e.g., based on information from the washing machine or iron), and/or any other information. The clothing recommendations are able to be implemented in any manner. For example, a user's wardrobe is stored digitally (e.g., text and image representations of the user's clothing are stored in a database), and based on the event information and the available clothing options, images/text of the clothing is presented to the user. The database is able to store information such as the type of event each item is for, for example, casual, fancy, business, athletic, warm, cold, and other categories. The database is also able to store which items match with other items, for example, by linking items. Furthering the example, a user is going to a fancy dinner, and a recommendation provides matching outfits for the user to select which are appropriate for the fancy dinner. In some embodiments, the system provides the actual outfit once the user selects it or informs the user where it is located. In some embodiments, the system also stores when items were worn to provide the user with new/fresh items that have not been worn recently.

In some embodiments, a recommendation is provided without a user requesting a recommendation. For example, based on time, location (of the user and/or contacts) and/or any other relevant information, the social networking event planning system automatically determines an event and proposes it to one or more users. Furthering the example, the social networking event planning system displays a message such as, "It's Friday night, how about Club Z with Contacts A, M, W and Y." In some embodiments, an auto-invitation is generated as well. The user is then able to select the auto-invitation or modify it (e.g., add or remove contacts or modify an aspect of the event such as when or where to meet). The event planning system is able to determine the current time/day, analyze past events and current possible events, analyze patterns and trends, analyze common interests and analyze any other information to make a recommendation without a user requesting one. The current possible events are able to be determined in any manner such as downloading a list of events and/or crawling/searching for events. In some embodiments, the events are specific events (e.g., only those with group coupons) and in some embodiments, the events are generally events within a geographic location. In some embodiments, other automated comments/responses are generated. Types of automatically generated content includes invitations, acceptances, rejections, responses, questions, and/or any other content. In some embodiments, the auto-generated content is the same for each contact, and in some embodiments, the auto-generated content is tailored to the recipient of the content. For example, if a birthday party invitation is going to a grandparent and a teenage girl, the auto-generated content for the grandparent is different than the content for the teenage girl. The differences in the content is able to be appearance (e.g., big black letters for the grandparent which are easy to see versus bright pink for the teenage girl, word usage (e.g., casual, business/formal, "street lingo"), transmission method (e.g., email, SMS message, Tweet) and/or any other characteristic of the content. The content is able to be automatically generated in any manner such as using a template (e.g., different templates assigned to each contact based on age, gender, and/or other preferences/characteristics) and incorporating specific details based on social networking information or input information.

In some embodiments, when users respond (e.g., on Twitter, message boards), these responses are analyzed and utilized when generating recommendations. Other characteristics are able to be analyzed as well (e.g., age, gender, location, occupation), and users are able to be recommended to connect and/or events are recommended.

In some embodiments, contacts are provided with generic information about an event, and the contacts are able to accept or reject a possible invitation. For example, User A is planning on inviting Contacts B, C and D to dinner on Friday night. Before the actual invitation is sent, Contacts B, C and D are informed of the dinner. The information provided to Contacts B, C and D is able to be very generic, such as "event Friday night coming" or very specific, "User A is planning on inviting you to dinner this Friday night with Contacts C and D" or somewhere in between. The contacts are then able to respond such as "accept" or "reject" to receive the invitation, and then they are able to accept or reject the actual invitation. The preliminary approval/rejection enables a user to reject something before they are fully aware of it to possibly lessen hurt feelings. For example, if Contact B performs a preliminary rejection because he already has plans for Friday, then he is not actually rejecting Contact A's invitation. The preliminary approval/rejection also allows the person providing the invitation to change the plan and/or invite others. For example, if User A selects Event X because he knows Contact B enjoys Event X, but if Contact B preliminarily declines, then User A is able to change it to Event Y and/or invite Contact D. In some embodiments, the communication is not between contacts but rather people who might know each other or might want to know each other (e.g., co-workers, neighbors, classmates). In some embodiments, users are able to set automatic responses such as to preliminarily accept all invitations so that the user is able to see the full invitation and determine whether to accept or reject it. In some embodiments, after the preliminary invitation is accepted or rejected by the contacts, the event planning system generates recommendations based only on those who accepted the preliminary invitation.

In some embodiments, when recommendations are provided, a "none" or "reject all" option or similar implementation is provided for the users to reject the recommendations. In some embodiments, if one or more contact rejects the recommendations, then a new set of recommendations are provided. In some embodiments, half or more than half of the participating contacts have to reject the recommendations for a new set of recommendations to be provided. In some embodiments, all of the participating contacts have to reject the recommendations for a new set of recommendations to be provided. In some embodiments, if a user rejects the recommendations, the user is prompted to provide a reason, so that the event planning system is able to learn why the recommendation was rejected. For example, a pop up is displayed with selectable options (e.g., too far, too expensive, not fun). The selectable options are able to be generic for all of the recommendations or users are able to specify which option goes to which recommendation.

An example of event planning using social networking information is: User A texts User B and asks about getting dinner with User C. User A and B are identified by caller identification, and User C is identified by name recognition. After the users are identified, their common interests are determined by cross-referencing a database which stores their interests. Based on the common interests either Chinese or seafood will likely be acceptable to all of the users. A search is automatically performed to locate a highly-rated restaurant equidistant to all of the users. Several restaurants are found and provided in a list form for the users to vote on, and whichever restaurant receives the most votes is selected, and GPS navigation to the selected restaurant is provided to all of the users.

Another example of event planning using social networking information is: User A wants to meet up with Users B, C and D, so using a social networking meeting app on his smart phone, he selects B, C and D from his contacts list. The system already knows from previous analysis that Users A, B, C and D all like Italian food, German food and Chinese food. The previous analysis included: information from a smart stove indicating User A made pasta five times in the past month suggesting he likes Italian food, that User B gave a German restaurant five stars on Yelp, and a Tweet where he said, "I love Chinese food," User B provided information on a dating site that lists Italian, German and Chinese foods as well as others, User C specified Italian, German and Chinese foods as foods he likes on his Facebook® page, and User D selected Italian, German and Chinese foods using the social networking event planning app. Additional analysis includes: determining the current location of each user based on GPS in their phones; determining restaurants matching the common likes using mapping information; determining traffic and arrival times based on traffic mapping information, the current locations of the users and determining wait times at the possible restaurants using online accessible wait time data. The app locates the possible restaurants based on the common interests, calculates expected arrival times for each of the users and incorporates the wait times for each restaurant. A recommendation is then made based on the calculations so that a restaurant with good food, relatively close to the users and with a relatively short wait time is recommended.

In some embodiments, messages are automatically composed based on social network information. For example, when a user accepts a meeting, the user is able to select from auto-composed messages to reply where the messages are developed based on social network information. Furthering the example, instead of a basic "I accept your invitation" message, the message is modified based on the contact's social networking page to say, "See you there bro, Go 49ers!"

In some embodiments, after a meeting or event, a communication is automatically generated. For example, after a business meeting, an email is automatically composed for the potential employee to send to the potential employer with content such as thanking the potential employer for lunch, including any additional information such as common interests, and/or links to the potential employee's web page and/or resume. In another example, a tweet is automatically generated after a date to suggest another date including time, location, and relevant information determined by analysis of the user and the contact. The user is able to then review the communication, modify it if desired and send it. In some embodiments, the communication is automatically sent without review.

In some embodiments, instead of or in addition to sending a communication after a meeting, products are suggested for purchase based on the meeting and/or other information. For example, after a first date, the user inputs that the date went well, or the social network information is analyzed (e.g., girlfriend tweets to her contacts "great night"), and the user is provided with links/advertisements/coupons to flower companies that will deliver in the area. Furthering the example, specific recommendations are able to be made based on social network information and/or other information. For example, flowers are recommended because the girlfriend does not eat chocolate, and more specifically, pink flowers are recommended because that is her favorite color, and even more specifically, a deal for pink flowers for $20 is provided because the user is a college student without significant funds. The information from each user's social network site, personal website, microblog posts, dating website information and/or any other information is able to be acquired, compared and/or utilized in any manner (e.g., by data mining and storing the data in a database). In some embodiments, a second meeting or event is recommended based on the information from or related to the first meeting and/or other information.

In some embodiments, the recommendations are synchronized with an augmented reality device to assist in locating someone. In some embodiments, the augmented reality device is able to be used to connect with people.

In some embodiments, travel plans are suggested based on social networking information and/or other information. For example, interests and hobbies are utilized to suggest destinations or side-trips while at a location. Furthering the example, banking/financial information is also analyzed to recommend travel plans. For example, the system notes that User A saved $2,000 over the past three months, and recommends a vacation that fits User A's budget. In another example, if a contact of a user is traveling at the same time to the same location, the user and the contact are notified of such an occurrence so that they are able to meet up. In another example, if a user is traveling to a location where a contact lives (and perhaps neither is aware), the user and the contact are provided this information. In some embodiments, the user is notified if a potential contact lives there or is going to be in the same location as the user. For example, based on high school information, a user is notified that Person X, whom you may have gone to high school with, lives in the same city that you are traveling to next month. The social network event planning system is able to be used to recommend an event as described herein.

In some embodiments, when a user goes on a business trip, the social networking event planning system is able to be used to help find restaurants, hotels, friends in the area, and/or any other item as described herein. In another example, a registration list at a business convention is able to be used in conjunction with the social networking event planner to throw a get-together/mixer afterwards. Furthering the example, the social networking event planner analyzes the people on the registration list and determines who to invite, what to invite them to (e.g., club versus restaurant), and/or any other information. The social networking event planner analyzes the likes/dislikes, common interests, and/or any other information to make a recommendation.

In some embodiments, after a location is determined for an event meeting, the information is provided to a self-driving vehicle which drives the user to the meeting place.

In some embodiments, vehicle features are automatically operated based on the event planning. For example, if a 7 pm dinner is recommended and accepted, and it is determined that it is 29 degrees outside, at 6:55 pm, the user's vehicle is started automatically, and the heater is turned on. Additionally, navigation information is generated, music preferences are set, and/or any other automatic operations are performed.

In some embodiments, security is implemented to prevent others from seeing information that is intended to be private.

In some embodiments, users are suggested to connect based on similarities, and then those events are able to be recommended to those connected users. Recommending users to connect is able to be based on any items such as music, cuisine, restaurants, movies, television programming, commercials, political affiliations, advertisements, images, videos, hobbies, activities, occupation, status, patterns, habits, lifestyle, preferences, ethnicity, religion, previous employment, home town/previous residence, school/college attended, major/minor in school, and/or any other information. For example, if a user has given the same or similar ratings as another user using the same social networking site, then the users are recommended to connect based on their similar music tastes. In some embodiments, an event is suggested that they attend. In another example, common interests of users who are unconnected are determined as described herein, and a connection score is generated based on the common interests. If the connection score is above a threshold, then the users are recommended to connect (e.g., a notice is sent to both users of a social networking site). For example, by analyzing the social networking sites, reviews and personal webpages of User A and User B, it is determined that they both enjoy Indian food, Chinese food, comedy movies and hiking, so a message is sent to User A and User B asking if they want to connect. In some embodiments, details are provided (e.g., User A is informed that another user also likes Indian food, Chinese food, comedy movies and hiking) In some embodiments, additional information is utilized in determining if users should be recommended to connect. For example, the users' current proximity to each other, future proximity, travel plans and/or other information is able to be used in conjunction with the common interests to compute the connection score. In some embodiments, disinterests are factored in as well as negatives. For example, if User A likes Chinese food and User B does not like Chinese food, then a negative value is added to the connection score. In an example of computing a connection score using the example above, 10 points are added for the users liking Indian food, 10 points are added for the users liking Chinese food, 20 points are added for the users liking comedy movies, and 20 points are added for the users liking hiking, giving a total of 60 points. If the threshold is 50 points, then the users would be recommended to connect. In some embodiments, users are recommended to connect only if they have at least one contact in common. For example, User A is connected to User M, and User M is connected to User Z, and User A and User Z have similar interests as described herein, so User A and User Z are recommended to connect. In some embodiments, the users are connected in the same social networking system, and in some embodiments, the users are connected in different social networking systems. For example, User A is connected to User M using Facebook®, and User M is connected to User Z using Google+®. In some embodiments, the contact of the users must be a direct or first level contact (e.g., User A is connected to User M), and in some embodiments, additional levels of contact are permitted (e.g., User A is connected to User B who is connected to User M, and User Z is connected to User J who is connected to User M, so User A and User Z are recommended to connect based on similar interests). In some embodiments, users are recommended to connect or an event is planned for users with opposing/opposite interests (e.g., opposites attract). For example, the users have many (e.g., above a threshold) interests where User A likes items that User B dislikes. In another example, a specific item is liked by both but other items are liked by one but not the other. For example, the users enjoy the same types of cuisines but have opposing political views and/or activity preferences.

In some embodiments, events are recommended to users where the users remain anonymous to each other (initially). For example, the event planning system determines that User A and User M have similar interests, and Event X would be an enjoyable event for them to attend together, as described herein. The users are provided the event recommendation but not specific user identification information. For example, the users are provided with the username of the other user, or a system is implemented where the users' devices are able to detect each other, so that the user's are able to find each other without having any identification information. For example, an app on the smart phone or other device of each user informs the user if they are getting "warmer" or "colder" with respect to the anonymous contact, or provides temporary tracking information of the anonymous contact, provides distance information of how close the anonymous contact is, automatically recognizes the anonymous contact (e.g., using facial recognition) and provides an alert when the anonymous contact is detected, provides an alert when the smart phone of the anonymous contact is within range (e.g., 10 feet) of the user, and/or any other implementation. In another example, the users are only provided images of each other and information about Event X. In some embodiments, the anonymity feature is optional. For example, a user is able to switch from being anonymous to known. In some embodiments, both users have to agree to switch before either identity is revealed. In some embodiments, the anonymous users are able to connect and communicate through the social networking system and remain connected temporarily until the event occurs. After the event, the users are able to select if they want to remain connected. In some embodiments, events are recommended to users, and the users remain anonymous to each other, but only users with at least one similar contact are recommended. For example, it is determined that User A and User Z have a contact in common, and it is also determined they have many interests in common, so an event is recommended for them, but they remain anonymous. In some embodiments, the common contact is disclosed to the users. As described herein, the contacts are able to be any level of contact or limited to a specified level of contact, and the contacts are able to be in the same social networking system or another social networking system. In some embodiments, events are planned for groups of anonymous users. For example, to avoid an uncomfortable situation of a one-on-one meeting of anonymous people, an event is planned (as described herein) for a group of anonymous users. In some embodiments, the users are able to monitor/determine how many other anonymous users are planning on attending. In some embodiments, limited information is provided about the other users of the group. For example, the users are able to see the gender of the other users. Furthering the example, a female user may not be comfortable if she is the only female meeting in this anonymous group.

In some embodiments, when events are planned for users who do not know each other, a background check is automatically performed. The background check is able to include searching public databases (e.g., criminal records), private databases, personal information (e.g., social networking sites) for anything that could be determined as dangerous or suspicious. For example, if a user has posted on his social networking page that he just robbed a bank, that user would either not be recommended to connect with someone else, or the user would be alerted of the information. The information is able to be detected/determined in any manner, such as via searching for keywords or any other information crawl/search.

In some embodiments, safety issues/concerns are a factor used for event planning. For example, places are giving a safety rating, and the safety rating is taken into account when planning an event. Furthering the example, for a meeting with two anonymous people, a public park at 9 pm may be given a low safety rating but a crowded restaurant is given a high safety rating.

In some embodiments, health information in common is utilized with the anonymous event planning or connection recommendation. For example, if users have similar weight issues and are determined not to go to the gym or are members of the same gym but do not go because they do not want to go alone, the anonymous event planning system is able to plan a meeting at the gym, so that the users will have a companion. In another example, users who share a common illness, such as breast cancer are informed of other users who want to attend an awareness walk but are hesitant to go alone. Users with similar health issues are able to be determined and events are able to be planned which are suitable based on taking the health issues into account as well as other information. In another example, mothers/fathers with young children are able to be matched up for play dates by incorporating common interests/information as well as age appropriate activities. In some embodiments, images/videos are utilized in determining health issues for anonymous event planning or connection recommendation. For example, images are analyzed to determine users are overweight and would benefit from exercising. Furthering the example, a photo of User A is analyzed, and a photo of User B is analyzed, and both are overweight. Additional information indicates that User A and User B live near each other and have other information in common. The two users are recommended to become contacts or meet at a gym. The images are able to be analyzed in any manner such as by comparing an image with a template (e.g., healthy body template versus overweight in photo).

In some embodiments, when performing anonymous event planning, user information is analyzed such as the number of contacts and/or calendar events. The number of contacts of a user is able to be analyzed to determine if they have a large number of friends. The calendar information and/or social networking information is able to be analyzed to determine if they have many events planned. If the number of friends and/or events planned are low (e.g., below a threshold), it may be assumed that the user is not very outgoing. Similar or opposite users are able to be matched. For example, two or several shy users are recommended to connect and/or an event is planned for them (the additional analysis described herein is also implemented for recommending connections/events). For example, User A has 5 contacts, and User B has 3 contacts, and neither has any calendar events planned, and analysis of their social networking pages does not indicate any plans. Further analysis is performed and User A and User B have some common interests and based on additional analysis are a good match, so User A and User B are recommended to connect and/or an event is recommended.

In some embodiments, the event planning system is able to be used for car pooling suggestions. For example, employees at the same company are located as well as their proximity to each other or similar routes to work. In another example, routes, daily schedules, work schedules, music preferences, activities, and/or any other information are analyzed, and car pooling recommendations are made. Furthering the example, although User A and User B do not work together, they work within 2 minutes of each other, live within 3 minutes of each other, have similar work schedules, and both enjoy hiking and surfing, so they are recommended to connect for car pooling. In some embodiments, a recommendation is sent to both. The recommendation is able to have limited information (e.g., simply that another user may be a good match for car pooling), or the recommendation provides details (e.g., name, address, work location). The users are then able to accept/reject the recommendation. In some embodiments, the users are able to accept a connection (e.g., through a social networking site) before agreeing to car pool.

In some embodiments, advertisements are generated/presented based on common interests. For example, a coupon is provided requiring two or more users to use the coupon. Furthering the example, User A and User B have similar interests, so they are provided with a coupon to one of their interests, but it is only usable if they both go.

In some embodiments, Near Field Communication (NFC) and/or other detection technologies are utilized to locate/detect other devices. For example, NFC is able to be utilized to determine when a user's device goes to a location (e.g., restaurant). In another example, NFC is able to be used to determine when a user's device comes within X feet (e.g., 3 or 5 feet) of another user's device. The location/proximity data is able to be stored and/or analyzed to perform recommendations. The data stored is able to include time, date, location, device information, user information, and/or any other information determined using NFC. For example, User A and User B do not know each other, but using NFC, it is determined they come within 5 feet of each other 10 times within one week. After determining they come near each other so often (e.g., above a threshold), their interests in common are analyzed as well as other information, and they are recommended to connect and/or an event is planned for them. In some embodiments, a score is computed based on the NFC information and/or the common interests and/or additional information, and if the score is above a threshold, then an (anonymous) event is recommended or connecting and/or event are recommended.

In some embodiments, places where people visit/check in using social networking sites are analyzed. For example, if User A and User B check in at the same place more than X times, then they are recommended to become contacts and/or meet at that location. In another example, if User A and User B check in at five of the same places, then they are recommended to become contacts and/or meet at one of those locations or a similar location they have not been to yet.

In some embodiments, users' web page favorites are analyzed in making a recommendation. For example, if User A and User B visit web page X most frequently or if their top 5 most frequent web sites are the same, this is able to be factored in when recommending the users to connect/meet.

In some embodiments, contests/awards/points/coupons/prizes and/or any other rewards are provided for users utilizing the event planning system. For example, to encourage users to go to an event, if the users go to the event they earn points which are later redeemable for prizes. In another example, a contest (e.g., an "Easter egg" hunt) is provided for users to search for items. Different rewards are able to be given depending on different actions taken. For example, utilizing the event planning system to plan a day's worth of events (lunch, activity, dinner, activity) earns a larger/better reward than a single event.

In some embodiments, the social network includes a one or more individuals and several companies.

In some embodiments, a user selects a location and contacts to meet at the location, and based on analysis, a determination is made regarding the likelihood of all of the contacts meeting at that location. As described herein, different information and different sources of information are able to be used in performing the analysis. For example, the current location of the contacts, their preferences, and/or any other information is able to be utilized. Furthering the example, a user selects to meet at a pizza place in San Jose, and the user invites four contacts to meet in 30 minutes. It is determined via GPS that one contact is currently in Napa, a second contact does not eat pizza, a third contact is 20 minutes away from the pizza place, loves pizza and is available, and a fourth contact is 15 minutes away, likes pizza but is currently, temporarily unavailable. Therefore, the chance of all four meeting at that location at that time is 0% since two of the contacts will not make it there in time or will not eat there. In some embodiments, a percentage is able to be provided for subsets smaller than the full invited contact list. For example, an output shows 0% for 4 of 4 contacts, 0% for 3 of 4 contacts, 20% for 2 of 4 contacts, and 99% for 1 of 4 contacts. In some embodiments, alternatives or recommendations are provided with a higher likelihood of success based on analysis as described herein. For example, an alternative meeting time is suggested for the following day at a different location when all five users are available. In some embodiments, many alternatives are provided in a list, so that the user is able to select. For example, 0% is provided for the original plan, but 20% is provided if the location is changed to a different pizza place that also has salads at a later time, and 50% is provided if the location is changed and the meeting time is postponed to the next day. In some embodiments, the alternatives are provided in descending order with the highest percentage first or on top. In some embodiments, the analysis is performed and the result is provided before the user contacts (e.g., sends the invitation to) the contacts. This allows the user to determine the best option without bothering the contacts first. In some embodiments, the results are color-coded in addition to or instead of providing a percentage. For example, when a meeting has 0-10% chance of happening, the result is red, 11% to 30%, the result is orange, 31% to 50%, the result is yellow, 51% to 70%, the result is blue, 71% to 90%, is purple, and 91% to 100% is green. In some embodiments, percentages are provided for each individual contact. For example, Contact 1 is 0%, Contact 2 is 0%, Contact 3 is 99% and Contact 4 is 30%. In some embodiments, the results are provided to the contacts. In some embodiments, the contacts are able to modify their percentages. For example, although Contact 3 loves pizza and is only 20 minutes away, he is not sure if he wants to go out tonight, so he reduces his percent to 90%.

In some embodiments, a user selects contacts, and an event is recommended, and in some embodiments, a user selects an event and contacts are recommended. For example, the user specifies going to a 49ers football game. Based on schedules, preferences and/or any other information, the social networking event planning system provides a list of contacts who may potentially want to join the user. In some embodiments, percentages of likelihood of attending the event are included with each contact. For example, a friend is available at the time of the game and really likes the 49ers, so his likelihood is 90% and at the top of the list, while another friend completely dislikes football, so her likelihood is 1% and is at the bottom of the list. In some embodiments, color coding or an icon is used to indicate likelihood as described herein. The user is then able to select whom to invite and will have a pretty good idea of whom will join him. In some embodiments, an advertisement is provided while performing the analysis, while providing the list of potential invitees, while invitees accept an invitation, and/or any other time. For example, after all of the contacts have either accepted or declined or after a deadline expires, an advertisement (e.g., link to a website) is presented to purchase the tickets. In some embodiments, information such as likes/dislikes of contacts are analyzed when recommending invitees. For example, if Contact C and Contact V do not get along, either one is recommended or both are recommended but a warning is provided that they do not like each other. For example, only the one with the higher likelihood of attending is recommended. In another example, both are recommended, but their names are flashing to indicate a conflict. In yet another example, only one is invited initially, but if that one declines, then the other is recommended or invited automatically. Conflicting contacts are able to be determined in any manner such as a user inputting that the two contacts conflict or based on data mined social networking information. In some embodiments, who likes whom and who conflicts with whom is able to be determined based on past events. For example, Contacts A, B and C have been to the past five dinners, so it is able to be indicated that they like each other. Other conflicts are able to be determined such as prior employers, competitors, ex-girlfriend/boyfriend/spouse, relatives of exes, and/or any other conflicts or potential conflicts. The conflicts are able to be incorporated in the analysis when recommending an event or the attendees of the event. For example, a job may not be recommended for a user if the employer conflicts with the user's current or previous employment. Conflicts are able to be determined by analysis of contracts/agreements and/or any other analysis. For example, Tech Company X has its employees sign non-compete agreements preventing the employees from working for Tech Company Y for a period of time. This information is able to be searched for and analyzed, and used to determine conflicts. For example, a job posting by a Tech Company Y is not displayed or is grayed out for the employee at Tech Company X. In some embodiments, users are able to provide input regarding conflicts such as what types of relationships are considered conflicts (e.g., one user is still friends with his ex-girlfriend, so there is no conflict, but another user views his ex-girlfriend as a conflict as well as any of her friends and any of their friends).

In some embodiments, when a user purchases a ticket to an event, the user is prompted with a query of: who do you want to invite? Then, a list of social network contacts is provided in order of likelihood of going based on social network information analysis, or contacts are automatically contacted via social media. In some embodiments, if additional users purchase tickets, the first user gets a discount or reward and/or other users get a discount/reward (group reward). In some embodiments, as each user purchases a ticket, their contacts are automatically contacted or a list is provided of contacts likely to attend with an automatically generated invitation that a user is able to send out.

In some embodiments, a recommendation utilizes images and/or video to encourage the user. For example, an image of the user provided on a social network is acquired. The image is modified to include a specific item on the user. Furthering the example, an image of a user hiking is modified to show the user in a new hiking vest. In some embodiments, the images are classified (e.g., hiking, beach, professional), so the appropriate image is used with the appropriate item (which is also able to be classified). In another example, an image of the user's house is modified to show new furniture in the house. In some embodiments, an image (or images or video) of a location (e.g., office, restaurant, club) is acquired, and a hologram or virtual reality is utilized to enable the user to feel like he is there. This will enable the user to be more accustomed to the location before actually going there.

In some embodiments, the recommendation description is tailored to each user, in other words, the recommendation description is user-specific. For example, instead of simply providing a list of names of restaurants to users for the users to select from, an image/video/description is provided to the users. Furthering the example, instead of providing a list of Restaurant A, B, C, D to a set of contacts as a recommendation, an image of Restaurant A tailored to each contact is provided, and an image of Restaurant B tailored to each contact is provided, and so on. Similarly, text or audio could be tailored to each contact too. For example, for User J, Restaurant C is described as having the best pizza in town, but for User K, Restaurant C is described as having great pasta. In some embodiments, a generic image of the restaurant or a signature dish is provided. In some embodiments, the image is tailored to the user. For example, a user who really enjoys pizza receives an image of Restaurant Z's famous pizza, but a different user who loves pasta receives and image of Restaurant Z's best pasta dish (or the specific dish that the user likes the most such as Fettuccini Alfredo as prepared by Restaurant Z). In another example, for a hike, User A's favorite aspect of hiking is the different kinds of flowers, User B really loves animals, and User C has many pictures of waterfalls. The users' favorites/likes are able to be determined in any manner as described herein such as analyzing their social networking pages (e.g., Pinterest, Facebook®) and/or stored content in the cloud (e.g., using DropBox, Box). Based on this information, when a hike recommendation (e.g., Yosemite hike recommendation 1) is presented to User A, a variety of flowers are shown in an image/slideshow or described in text. The same hike recommendation (e.g., Yosemite hike recommendation 1) is presented to User B but instead of showing flowers, animals that may be seen on the hike are shown/described. For User C, the waterfall that can be seen on the hike is shown/described. The tailored information is able to be stored/presented in any manner. For example, a data structure is utilized to store different aspects of Restaurant Z. Furthering the example, a generic photo of Restaurant Z is stored, a pizza dish from Restaurant Z is stored, a pasta dish from Restaurant Z is stored, and a salad dish from Restaurant Z is stored. The users' preferences (e.g., User A likes pizza, User B likes pasta) are compared using the data structure, and the appropriate content is then presented to the users based on their preferences. For example, the event planning system determines User A's preference is pizza, and Restaurant Z has a pizza-specific content, so the pizza-specific content is presented to User A when Restaurant Z is recommended. In some embodiments, the tailored content is varied or randomized. For example, if a user likes pizza and pasta, the first time Restaurant Z is recommended, pizza content is shown, and the second time, pasta content is shown. In some embodiments, both (or more) are shown/provided.

In some embodiments, reactions to recommendations are monitored/captured/analyzed/utilized for further analysis and/or recommendations. For example, a recommendation of Restaurant Z is presented to a user. A camera device on the user's smart phone monitors the user's reaction to the recommendation. For example, the camera device detects smiles, laughing, frowns, furrowed brows, lip-reactions, mouthed words, and/or any other reaction (facial or otherwise) by comparing the monitored information with a template (or any other manner). Based on the reactions, the event planning system is able to give the recommendation a rating for the user (e.g., if the user frowns when seeing a recommendation, the recommendation is given a 1 on a scale of 1 to 10). Then, for future recommendations, the rating is factored in when providing recommendations.

In some embodiments, wearable items such as clothing, watches, exercise bands, and/or jewelry are able to be utilized to indicate event planning information. For example, an event planning bracelet is red when an event is two or more days away. The bracelet turns yellow when the event is one day away. The bracelet turns green on the day of the event. The bracelet is able to store event planning information (e.g., time/date information) and also current time/date information and compare the information to determine which color to produce. In some embodiments, the wearable item includes an alarm that rings, vibrates or flashes when the event is coming soon (e.g., in 5 minutes or in 1 hour). The wearable item is able to be manufactured in any manner such as containing a power source, circuitry and a light or other output mechanism. In some embodiments, the wearable item is able to communicate with a cloud device to send and/or receive information (e.g., a signal to change color).

In some embodiments, caller identification on a smart phone indicates if a user is part of a planned event. For example, when User A calls User B, User B's smart phone includes an icon indicating that User A is going to be attending an upcoming event with User B. In some embodiments, the icon is selectable for more information. In some embodiments, the icon is related to the event. For example, if the event is dinner at a pizza place, then a pizza slice is indicated, and if the event is a hike, a tree is indicated. Displaying the icon is able to be implemented in any manner such as comparing the caller's phone number with a database including events, phone numbers of contacts planning on attending the events, types of events and icons representing the events and displaying the icon or graphical representation or text if a match is found.

In some embodiments, before/during/after a recommendation is made, a scent sample is provided to a user. For example, an odor-generating attachment is provided for a smart phone which generates a generic (e.g., Italian) or specific odor (fettuccini alfredo), and then the user is able to accept/reject (e.g., by touchscreen or face sensor recognizing reaction of user) based on the odor. Furthering the example, the user is deciding between Italian and Indian, and the user smells a generic smell of both, and then selects to accept Indian. The selections are then able to be used in providing a recommendation. In some embodiments, each contact is provided with the scent, and in some embodiments, only the user planning the event is provided with the scent.

In some embodiments, a graphic is provided to users indicating where the users have been or not been, which ones have been recommended and accepted/rejected, and/or any other information. For example, a map is provided with restaurants visited highlighted in green, and restaurants not visited highlighted in red. In some embodiments, the brightness of the highlighting indicates how recently visited (e.g., bright green is more recently visited).

In some embodiments, a set of events are presented for users to select, and recommendations are provided. The users are able to de-select events they are not interested in. The users are able to rank events they are interested in. The users are able to select different levels of interest (e.g., likely going, maybe going, not going). The events for selection are able to be based on daily, weekly, monthly, or other schedules.

For example, for Contacts A, B, C and D, the event planning system sends out options for Friday night where the options are Movie X, Club Y and Dinner Z. Contacts A and B select Movie X and Club Y as likely. Contact C selects Club Y as likely, and Contact D selects all as unlikely. A communication is sent to Contacts A, B and C that they all selected Club Y as likely and/or prompts them to invite each other. A communication is also sent to Contacts A and B that they selected Movie X as likely and/or prompts them to invite each other. In some embodiments, steps are automated. For example, the step of selecting interests is automatically performed based on any of the analysis described herein. Furthering the example, a trend has been determined that Contact A has gone to Club Y five weeks in a row, so that is automatically placed as a likely event. In another example, it is determined based on a digital receipt that Contact B has already purchased a ticket for Movie X, so that is a definite event for Contact B. Additionally, the communication between the contacts is able to be automatic. For example, if Contacts A and B have selected likely to attend Movie X, then a text message is sent from one to the other asking to meet up/go together. In some embodiments, users are able to place a percentage of likelihood, and if the percentage is above a threshold, then an automatic communication is sent. For example, Contacts A and B both have attending Movie X as 95% likely, and the threshold for automatically sending a communication is 90%, then the communication is automatically sent.

In some embodiments, the event planning system is used in conjunction with a search engine or other search mechanism. The input to the search engine is analyzed, and if it is determined the input is an event or related to an event, then event planning information is provided. For example, User A inputs the search term "hike" into a search engine (e.g., Google®). Instead of merely providing links to hikes, contact information of contacts who enjoy hiking is provided (e.g., in the same web browser or in a pop-up window). Furthering the example, hikes near the user's current location or future location are provided or hikes near the user and contact are provided. Any other helpful information is able to be provided/analyzed to organize the event such as weather conditions. In another example, User A inputs "restaurant in Mountain View Friday night." Tabs (or any other input mechanism) are displayed for User A to select Contacts B, C and D. Contacts B, C and D are displayed because they have previously gone to dinner with User A, they do not currently have plans for Friday night, and there is no indication they will be out of town. The search engine utilizes the interests in common such as cuisine preferences, recently eaten meals and/or any other information described herein. Based on the common interests and other information, the search engine provides two Indian restaurants and a Thai restaurant as search results. In another example, User A selects Contacts B, C and D before performing the search. In another example, the initial search results are displayed, but the search remains pending and changes as new information is determined. For example, if Contact B cancels, a new search is performed, or if one of the restaurants becomes full, the result is eliminated or grayed out.

In some embodiments, the user receives a list of recommendations, ranks the recommendations, selects a subset of recommendations (e.g., 5 of 20), and only the selected recommendations are sent to contacts who rank the recommendations. For example, User A wants to have dinner with Contacts B, C and D. The event planning system provides User A with 20 possible restaurants based on the analysis described herein. User A then selects and/or ranks five of those 20 restaurants to be sent to Contacts B, C and D (e.g., via text message or through an event planning app). Contacts B, C and D then make selections from and/or rank the five restaurants. Based on the selections/rankings of A, B, C and D, a restaurant is chosen. For example, A, B, C and D all rank Restaurant Z as their #1 pick, so that one is chosen.

In some embodiments, a Graphical User Interface (GUI) is utilized for interacting with the event planning system. The GUI includes images/icons/avatars of contacts such that the images are selectable (e.g., touchable) to include as invitees. The GUI includes images/icons/graphical representations of events for selection. In some embodiments, the contacts and/or events are displayed based on rank; for example, highest ranked events first/top and/or contacts most likely to attend first/top. In some embodiments, contacts/events are displayed in a circle or spiral with smaller items further down the spiral as lower ranked/less likely items. In some embodiments, contacts/events are displayed in a chart with higher ranked/more likely items as larger parts of the chart. In some embodiments, contacts/events are displayed in 3-D. In some embodiments, contacts/events are displayed in tiles. The GUI displays the information at any/all stages of the event planning process such as during user selection of contacts/events, during analysis of the contacts/events/other information, during presentation of recommendations, and/or any other stage. In some embodiments, the GUI displays current locations and/or future locations of contacts for the user/contacts to view. For example, based on the GUI, the user sees that Contact C is going to be out of town, so the user does not include Contact C as a possible invitee. The GUI is able to indicate how many times an event is recommended, the position the event is recommended (e.g., first, second, third), how many times the event has been accepted/rejected, and/or other information about previous recommendations. In some embodiments, if an event is recommended X times (e.g., 5 times) with the top Z recommendations (e.g., top 3 or first), and has not been accepted, then negative points are provided for that event. For example, Restaurant E has been recommended in the top three, five different times, and has never been accepted as the event to attend, so for future recommendations, the chances of it being recommended in the top 3 are lower. In some embodiments, as time passes, the effect of the previous rejections decreases. For example, if a restaurant was rejected three times, seven years ago, no negative points are applied. In some embodiments, in addition to or instead of using the GUI, a device informs a user of information by vibrating, by causing lights (on or separate from the display) on the phone to flash, and/or utilizing any other notification mechanism. In some embodiments, a device sends a signal and/or any information to another device to cause that device to inform/alert the user.

In some embodiments, a recommendation is provided based on a sample representative of the group. For example, it is determined which user or users are most representative of the group based on common interests and/or additional information, and the recommendation analysis is performed using only the sample instead of the entire group. Furthering the example, if a group of 5 contacts are planning on meeting for an event, two of the contacts are selected as the representative sample, and any of the computations/analysis described herein utilizes the representative sample. In some embodiments, only a sample of the group is presented with the recommendations, and whatever the sample selects is the selected event. In some embodiments, an analysis sample is used (e.g., only 2 contacts of 5 contacts for performing recommendation analysis), and a selection sample is used (e.g., only 2 of 5 contacts for selecting an event from a list of recommended events). The analysis sample and the selection sample are able to be the same users/contacts or different users/contacts. For example, Contacts A, B, C, D and E are planning an event. Information for Contacts A and B is used in the recommendation analysis, and then Contacts D and E are provided the recommended events from which to select. Using samples may reduce the amount of analysis performed and/or the number of users who would select/respond to a recommendation which increases efficiency.

In some embodiments, the event is a job interview or job-related. For example, the implementation described herein is able to be used for job matching, job finding, and/or job recommending. By analyzing social networking information or other information, it is able to be determined if a potential boss and a potential employee have the same or similar interests and/or if other information indicates a good match. For example, by matching two people who have an interest in the same hobby (e.g., golf), the future work relationship may be furthered by their personal similarities. Additionally, information is able to be analyzed/compared as well, such as ethnicity, religion, previous employment (e.g., potential employee previously worked with current employees at potential employer), home town/previous residence, school/college attended, major/minor in school, and/or any other information. In some embodiments, the information in common is provided to the potential boss, potential employee, or both. For example, before an interview, the applicant is made aware that the potential boss likes golf, so that the applicant is able to discuss that topic in the interview. Similarly, the interests or other personal information of people in the same office/group/company is able to be compared with potential employees. For example, if 10 out of 10 of the people in the office play golf, this information is able to be utilized to match a potential employee who plays golf (or increase a recommendation score). In some embodiments, the potential employee is "connected" via social networking to at least one person in the office/group/company. In some embodiments, the potential employee is not connected.

In some embodiments, personalities are analyzed. The personalities are able to be determined based on analyzing images, videos, social networking information, and/or any other information. After analyzing the information, matching is able to be performed. For example, a more laid back boss is matched with a laid back potential employee. In another example, a prospective employee is able to find out favorable or unfavorable qualities of a potential employer based on history of employment, professional and social contacts, searching news about the employer and/or any other information. The information is able to be gathered and provided to the user so that he does not need to do a search on his own.

Additionally, the social networking information is able to be used to suggest a time/place for an interview based on likes/dislikes and other information as described herein. The schedule of the potential boss and/or potential employee is also able to be analyzed and used for suggesting the time/place of the interview. In some embodiments, the schedule is utilized to coordinate a meeting based on determining two or more users are in a similar or the same location at the same time. For example, if a potential employer and a potential employee both attend a convention in Las Vegas, a dinner meeting while there is able to be recommended.

In some embodiments, the location of the company and the location of the potential employee's home (e.g., commuting distance between the two) is analyzed in recommending a potential employee. For example, a user who lives close to the company may be more inclined to stay with the company longer. Similarly, the status of the potential employee (e.g., renter or homeowner) is also able to be factored in. For example, a renter typically has more mobility, and may not be as inclined to stay at a position as long as a homeowner. In some embodiments, other information is analyzed as well such as marital status or family status (if allowed by law). In some embodiments, work history (e.g., how long at the same company), age of children (parents with children in school prefer not to move), dedication to work and/or nature of hobbies (which may hint at work ethic, professionalism) and/or other information is analyzed.

In some embodiments, the location of a job recommendation is based on comments (e.g., on a social networking page or microblogging site). For example, although a user lives in Texas, he tweets while visiting San Francisco, "SF is so beautiful," so job recommendations in San Francisco are presented to the user. In some embodiments, the user is asked if they would like recommendations for a location before or after providing the recommendations. Parsing comments is able to be performed in any manner; for example, locations are detected (e.g., matched with location information in a database), and adjectives are also detected. Furthering the example, the adjectives are classified such as positive and negative, such that "beautiful" is considered positive which would suggest this location to be added as a possible recommendation. If the adjective were "horrible," then the location would be added to a "do not recommend" database or similar structure. In some embodiments, other information is utilized when parsing information such as GPS information. For example, if a user tweets, "it's so beautiful here," the "it's" is able to be determined as San Francisco based on the GPS information.

In some embodiments, the recommendation of a potential employee or employer is presented in a competitive format. For example, five people are recommended as potential employees, and their qualifications/statistics are compared in a table/chart format.

In some embodiments, the user is able to take notes and/or a history is maintained for the user regarding contacts. For example, after a user meets with the CEO at Company X, the user notes in an app that the CEO is a great guy who really cares about his employees. This note is able to be stored so that in social networking apps that include the CEO as a contact, the note is available/displayed to the user. In some embodiments, the history of purchases are stored and are accessible as well. For example, the user purchased flowers for his girlfriend two months ago, candy last month, and does not know what to buy this month. Since the purchases are automatically available and linked to the contact, the user is able to easily review his history of purchases for that contact. In some embodiments, the information is taken/extracted from the site used for purchasing, acquired using a scanner (e.g. barcode or QR code), and/or the purchase information is manually input. In some embodiments, the notes are able to be kept private or made public. In some embodiments, the notes are regarding a contact, and in some embodiments, the notes are regarding someone who is not a contact. For example, a user reads a story about a member of a social networking group who is very rude. The user is able to make a note about that other user (e.g., using the other user's username), so that the user does not attempt to connect with the other user or if the other user attempts to connect with the user, the user is able to decline the connection. In some embodiments, if the user receives an invitation to connect from the other user, a username comparison determines that the other user is on a list of people not to connect with, and the invitation is automatically declined or an alert is provided to warn the user not to connect. In some embodiments, usernames are highlighted (e.g., different colors) based on the number of people who have accepted/declined their invitation or have negative indications/notes about the user.

In some embodiments, analysis of a potential employer or employee includes analyzing any relevant information about the employer/employee, for example, reviews by the user or of the user on review sites or other sites/articles (e.g., "best companies to work for" by Magazine F). Furthering the example, if an employer has been negatively rated on a review site, that information is analyzed and utilized to not recommend the employer to an employee. In another example, if a user has written many thorough and eloquent reviews on a review site, they may be a good employee. Web pages, blogs, and/or any other information is able to be crawled for an employee/employer name and then analyzed to provide a recommendation. In some embodiments, the additional information is not analyzed or partially analyzed, but the information is retrieved and provided to the user. For example, three web pages, two review pages, and a biography page of a potential employer are provided to a potential employee, so that the potential employee is able to read about the potential employer. In some embodiments, the information is summarized and provided to the user.

In some embodiments, a user posts/selects a "job wanted." For example, the user selects employment status as "searching." The social networking event planning system analyzes the user's information (e.g., resume, personal information and/or any other information), and searches through contacts (including contacts of contacts to nth level contacts depending on the implementation) and information related to the contacts, and based on comparisons, a recommendation is made such as "a match has been found in your job search." In some embodiments, keyword comparisons are implemented to match a potential employee with a potential employer. In some embodiments, additional information is analyzed as described herein such as personality information, personal preferences, hobbies and/or any other information.

In some embodiments, contacts of a user that are employed at a potential employer is another factor to analyze. For example, if a user already is connected to five people at the potential employer, that is able to be used to recommend the user for an interview. Additionally, the five people's names are able to be provided to the potential employer, so that he is able to discuss the user with them.

In some embodiments, instead of a user performing a job search, the system provides suggested searches for the user based on recent activity (for example, some people have a hard time actually sending out resumes even though they are unhappy with their jobs; based on email to a friend, the system searches and suggests contacts or meetings that might be helpful). In some embodiments, the system monitors for contacts changing jobs—for example, a contact of a user just left Firm A, both are attorneys in the same field, so the user is given the contact information of Firm A. In a similar example, a manager from a firm that employs a contact has received a promotion (so the manager position will need to be filled), and the user is given information and/or the user is automatically recommended as a replacement to the firm.

In some embodiments, the system is able to assist college students or other students in finding internships and/or employment. For example, a student specifies that he wants to stay local or wants to move to a specific location, that information is able to be analyzed in addition to the other analysis described herein to provide recommendations of whom to interview with or meet with. For example, there may be faculty that the student should talk with or connect with because certain faculty members are contacts with potential employers. Other recommendations (e.g., connection recommendations) are able to be given or other information to assist the user is obtained. For example, events to meet current employees of a company are able to be provided. Furthering the example, the CEO of Company X is giving a speech at the user's school in a week, so this information is provided, so that the user may introduce himself afterwards. Transcript information is able to be provided to potential employers which are able to use filters and/or the transcript information is analyzed to provide recommendations. For example, a student with a GPA of 3.9 is given additional points towards their recommendation over a student with a GPA of 2.8.

In some embodiments, additional information such as healthcare costs, moving expenses, and/or any other information is analyzed to generate a recommendation. For example, if a user leaves a current job which provides healthcare for a higher paying job that does not provide healthcare, the cost of healthcare could actually cause the user to effectively make less at the new job. Information about employers, healthcare information and any other information is able to be acquired from online sources and/or stored in a data structure (e.g., database) which is able to be compared.

In some embodiments, classes are able to be recommended. For example, a user is considering switching jobs, but the user needs to become more proficient in one aspect, so classes are able to be recommended to the user.

In some embodiments, a sequence/group of events are able to be recommended. For example, a user wants to switch from his current position to become a software developer. However, to do this, the user needs to take some classes in software development, move to a location with more developer jobs, and find a place to live. Using the analysis described herein, the set of events are able to be planned and recommended such as suggesting a move to the Bay Area where there are many jobs, providing apartment rental options based on the user's current financial situation, and suggest classes that are offered near the rental options. The system is able to perform further actions as well such as enabling the user to sign up for the classes, download a rental agreement form, book a flight, find a moving company, and/or any other action/service.

In some embodiments, a full life planner is implemented to provide recommendations. For example, if a user has a baby, the system is able to factor in daycare information, preschool information, elementary school information, additional schooling information, house information (e.g., prices), job information, environmental information, crime information, and/or any other information to provide a recommendation to the user. Furthering the example, the user lives in a part of the country where the schools are not very good and job opportunities are scarce. The system is able to recommend a location that the user is not very familiar with but has good schools, many jobs, reasonable housing, and any other factors to help the user make a decision.

In some embodiments, the system compares credentials of a user with current employees of a company and determines if the user may be a better fit for the company. For example, Employee X has 1 year of experience and is making $70,000, while User G has 3 years of experience and is willing to work for $60,000, so User G's resume is automatically provided with a hiring person at the company and/or User G is connected (or recommended to connect) with the hiring person.

In some embodiments, the system analyzes a company's finances and provides a recommendation for hiring. For example, the company had a large profit, and the goal of the company is to grow, so potential candidates are provided.

In some embodiments, the system helps users find temporary positions by matching the user's schedule with the potential employer's schedule and any other information.

In some embodiments, salary analysis is performed when providing a recommendation for a job. The user's past or current salary is able to be analyzed as well as the employer's typical salary for a position. Both are able to be determined in any manner. For example, the user's current salary may be available on his social networking site. In another example, an employee with the same or similar position at the employer posts on his social networking page that his salary is $X and that he has Y years of experience; this information is able to be used to determine the salary of the position.

In some embodiments, genetic information is analyzed and utilized for selecting a person for employment or as an employer. The genetic information is able to be gathered and analyzed in any manner, for example, specific genes that indicate positive or negative traits about a person that are relevant to the person's employment capabilities are located. Furthering the example, a gene which indicates a person's work ethic is detected, if the user has this specific gene or the correct characteristics of the gene, this information is able to be factored in when offering a person a position or an interview.

In some embodiments, the jobs, positions, standing, qualifications, and/or any other information of the user's contacts are analyzed when analyzing the user. For example, User A and User B happen to have the exact same qualifications. However, User A has five contacts which have all graduated from Ivy League schools and are currently employed at impressive companies. User B has five contacts, three of which are unemployed, one is employed with an unimpressive company, and the other is employed at a good company but in an unimpressive position. Based on the associations of User A, User A is given a higher recommendation by the system. The analysis of contacts is able to be performed in any manner. For example, contacts are located through social networking sites, and their schooling, occupation and/or other information is acquired through the sites or through other sources (e.g., company websites, professional websites, school websites). The information is able to be scored in any manner (e.g., top 10 schools per reliable magazine ratings are given +100 points, schools 11-50 are given +50 points, and schools 51-100 are given +25 points). In some embodiments, the level of contact affects the weight of the contact's score. For example, a contact who is a friend is weighted more heavily than a non-friend. Or a direct contact is weighted more than a contact of a contact. The score/effect of the contacts is able to be implemented in any manner. For example, the potential employer is able to specify the effect (e.g., employer specifies to only give value to schools attended but not employment history of contacts). In another example, positions are weighted higher than employer which is weighted higher than schools attended. The information of contacts is able to affect the recommendation in any manner. For example, a base recommendation score is automatically generated based on the user's current position, length at current position/employer, current employer, schools attended, and GPA at the schools. Then, the contact recommendation score is added to the base score but is valued at 20% of user's score. So if the user receives a base score of 90 out of 100 and a contacts score of 18 out of 20, then the user's final score is 108 out of 120. This score would be better than a user whose base score is 90 out of 100 but whose contacts score is 10 out of 20 which is a final score of 100 out of 120.

An example of computing a job-related recommendation is described herein. Based on analysis, it is determined that User A has similar interests to many employees at Company Z which earns User A +8 points. Based on personality analysis User A's personality is a good match for Company Z which earns User A +15 points. User A's skills are a match for Company Z which is another +50 points. Location and other personal analysis gives User A +5 points. Contact information of User A also provides another +10 points for a job recommendation score total of 88 points. The job recommendation score is able to be compared with a threshold (e.g., user-generated or automatically generated), and an additional step is taken when a user with a job recommendation score above the threshold is determined. For example, an interview is automatically set up, a notification is automatically sent to the potential employer and/or employee, and/or any other step. The job recommendation score is able to be compared with other job recommendation scores. For example, User A's score is compared with User B's score, and additional steps are able to be taken based on the comparison. For example, an interview is automatically set up with the user with the higher score, a notification is automatically sent to the potential employer and/or user with the higher score, and/or any other step.

In some embodiments, the order of the steps in FIG. 1 is modified. For example, the users are determined before monitoring the information. In some embodiments, additional or fewer steps are implemented.

In some embodiments, the steps described herein are able to be implemented on any device or any combination of devices. For example, a user's smart phone performs all of the steps. In another example, a user's smart phone receives input, and sends the input received to other devices (e.g., a server or cloud devices) and receives information back. In another example, cloud devices perform all of the steps. The steps are able to be implemented automatically, manually and/or a combination thereof.

Figure 2:
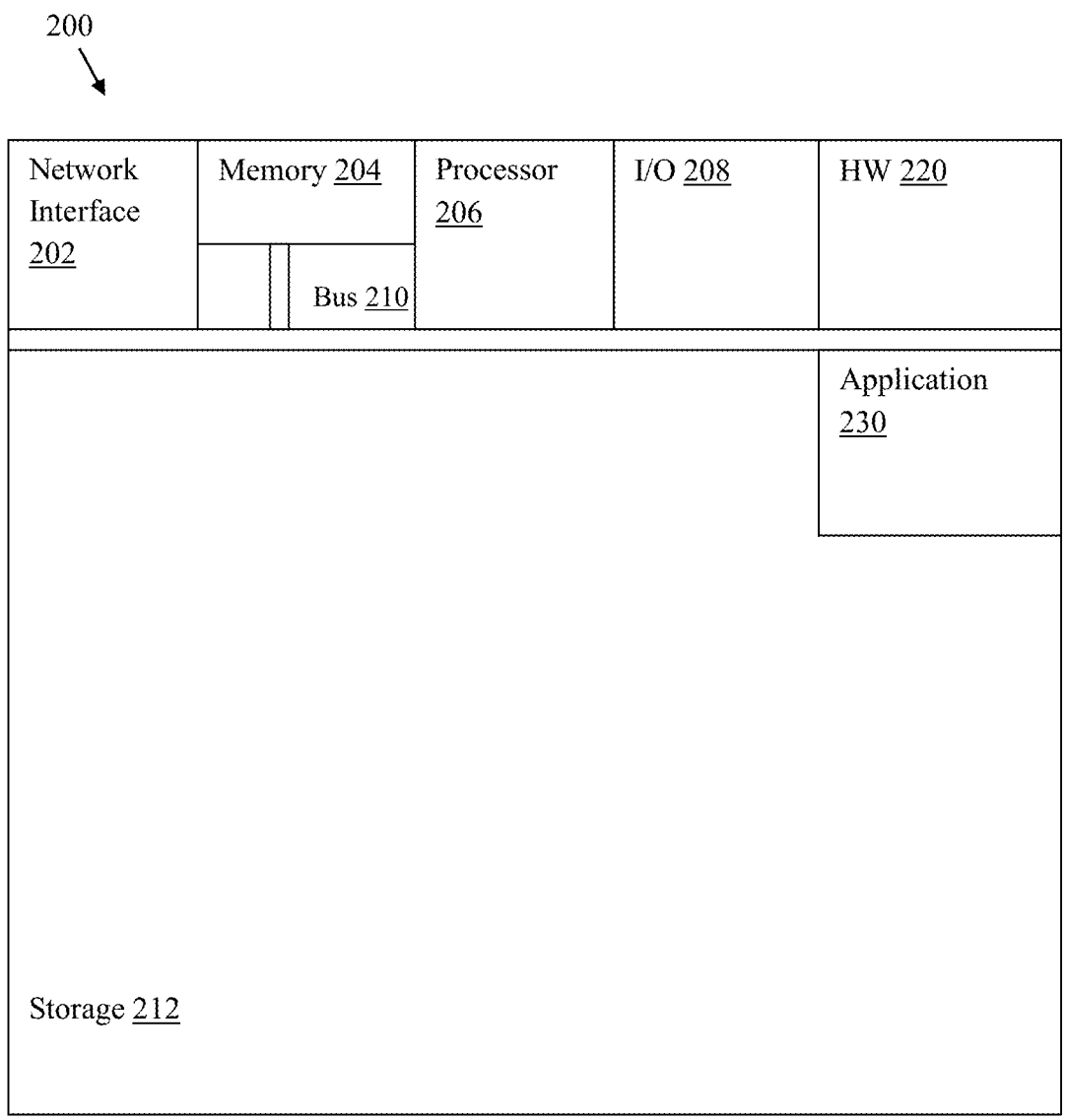
FIG. 2 illustrates a block diagram of an exemplary computing device configured to implement the event planning using social networking method according to some embodiments.

FIG. 2 illustrates a block diagram of an exemplary computing device 200 configured to implement the social networking event planning system according to some embodiments. The computing device 200 is able to be used to acquire, store, compute, process, communicate and/or display information including, but not limited to, text, images, videos and audio. In some examples, the computing device 200 is able to be used to monitor information, process the information, perform analysis and/or provide a recommendation. In general, a hardware structure suitable for implementing the computing device 200 includes a network interface 202, a memory 204, a processor 206, I/O device(s) 208, a bus 210 and a storage device 212. The choice of processor is not critical as long as a suitable processor with sufficient speed is chosen. The memory 204 is able to be any conventional computer memory known in the art. The storage device 212 is able to include a hard drive, CDROM, CDRW, DVD, DVDRW, flash memory card, solid state drive or any other storage device. The computing device 200 is able to include one or more network interfaces 202. An example of a network interface includes a network card connected to an Ethernet or other type of LAN. The I/O device(s) 208 are able to include one or more of the following: keyboard, mouse, monitor, display, printer, modem, touchscreen, touchpad, speaker/microphone, voice input device, eye detection, infrared detection, hologram detection, button interface, hand-waving, body-motion capture, touchless 3D input, joystick, remote control, brain-computer interface/direct neural interface/brain-machine interface, camera, and other devices. In some embodiments, the hardware structure includes multiple processors and other hardware to perform parallel processing. Social networking event planning application(s) 230 used to perform the monitoring, processing, analyzing and providing are likely to be stored in the storage device 212 and memory 204 and processed as applications are typically processed. More or fewer components shown in FIG. 2 are able to be included in the computing device 200. In some embodiments, social networking event planning hardware 220 is included. Although the computing device 200 in FIG. 2 includes applications 230 and hardware 220 for implementing the social networking event planning, the social networking event planning method is able to be implemented on a computing device in hardware, firmware, software or any combination thereof. For example, in some embodiments, the social networking event planning applications 230 are programmed in a memory and executed using a processor. In another example, in some embodiments, the social networking event planning hardware 220 is programmed hardware logic including gates specifically designed to implement the method.

In some embodiments, the social networking event planning application(s) 230 include several applications and/or modules. Modules include a monitoring module for monitoring information, a processing module for processing (e.g., converting) information, an analysis module for analyzing information and a providing module for providing a recommendation. In some embodiments, modules include one or more sub-modules as well. In some embodiments, fewer or additional modules are able to be included. In some embodiments, the applications and/or the modules are located on different devices. For example, a device performs monitoring, processing, and analyzing, but the providing is performed on a different device, or in another example, the monitoring and processing occurs on a first device, the analysis occurs on a second device and the providing occurs on a third device. Any configuration of where the applications/modules are located is able to be implemented such that the social networking event planning system is executed.

In some embodiments, a specialized computing device is utilized to implement the social networking event planning system. In some embodiments, the specialized computing device utilizes a dedicated processor and/or dedicated memory for processing event planning information. In some embodiments, instructions are stored on the specialized computing device to enable the computing device to efficiently analyze information to provide event planning recommendations.

Examples of suitable computing devices include, but are not limited to a personal computer, a laptop computer, a computer workstation, a server, a mainframe computer, a handheld computer, a personal digital assistant, a pager, a telephone, a fax machine, a cellular/mobile telephone, a smart appliance, a gaming console, a digital camera, a digital camcorder, a camera phone, a smart phone/device (e.g., a Droid® or an iPhone®), a portable music player (e.g., an iPod®), a tablet (e.g., an iPad®), a video player, an e-reader (e.g., Kindle™), a DVD writer/player, an HD (e.g., Blu-ray®) or ultra high density writer/player, a television, a copy machine, a scanner, a car stereo, a stereo, a satellite, a DVR (e.g., TiVo®), a smart watch/jewelry, smart devices, a home entertainment system or any other suitable computing device.

In some embodiments, a dedicated event planning button is provided on a device (e.g., smart phone). The button is able to be utilized in any manner. For example, if the user presses the button, a display is presented for the user to select an event based on his current location and contacts to invite to the event. In another example, by pressing the button, a list of all pending events is displayed in chronological order.

Figure 3:
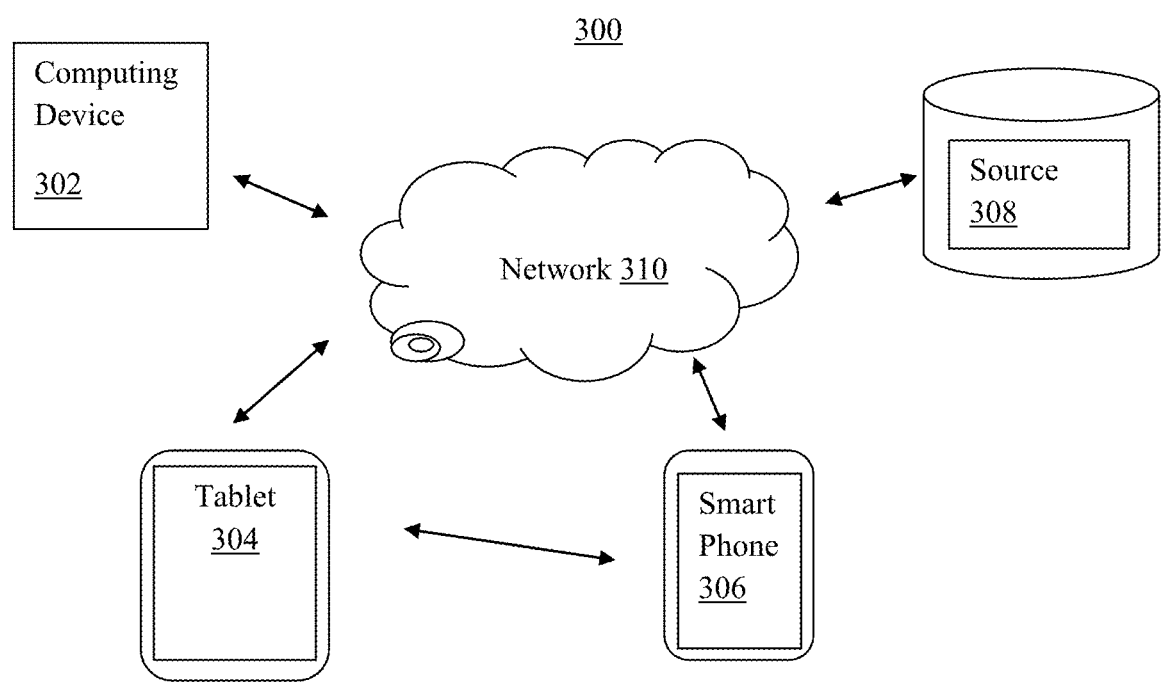
FIG. 3 illustrates a network of devices configured to implement event planning using social networking according to some embodiments.

FIG. 3 illustrates a network of devices configured to implement social networking event planning according to some embodiments. The network of devices 300 is able to include any number of devices and any various devices including, but not limited to, a computing device (e.g., a PC) 302, a tablet 304, a smart device 306 (e.g., a smart phone) and a source 308 (e.g., a database) coupled through a network 310 (e.g., the Internet). The source device 308 is able to be any device containing source information including, but not limited to, a searchable database, web pages, social networking information, statistics, historical information, or any other information or device that provides information. The network 310 is able to be any network or networks including, but not limited to, the Internet, an intranet, a LAN/WAN/MAN, wireless, wired, Ethernet, satellite, a combination of networks, or any other implementation of communicating. The devices are able to communicate with each other through the network 310 or directly to each other. One or more of the devices is able to be an end user device, a server, a cloud device, a company device and/or another entity device.

FIG. 4 illustrates diagrams of exemplary common interest data structures according to some embodiments. In Table 400, information such as a user's name and his likes/dislikes are stored. In Table 402, similar information is stored, except a yes or no value is stored for each item. In Table 404, user likes are grouped by topic, such that if a user is not included in a topic, then they do not like that topic. Although a user's name is shown, any identifier is able to be used. The tables in FIG. 4 are not meant to limit the invention in any way, as they are merely examples. Any storage structure and scheme is able to be utilized/implemented.

FIG. 5 illustrates a flowchart of a method of utilizing the social networking event planning system for employment searches according to some embodiments. In the step 500, information in common is determined. For example, a user's likes/dislikes are compared/matched with contacts' likes/dislikes. In the step 502, additional information is analyzed. For example, it is determined which contacts are potential employers. For example, contacts are classified as employee level (e.g., engineer), employer level (e.g., manager) and/or any other level. Additional information is also able to include any of the other information described herein such as personality information, hobbies and/or any other relevant information. Skills and job requirements are also able to be matched. For example, if a potential employer works at a company that programs using Java, and a potential employee has 5 years experience programming in Java, that is considered a match. In the step 504, a recommendation is provided. As described herein, the information in common and additional information are analyzed used to compute a recommendation. For example, the recommendation provides contact information between the contacts. In another example, the recommendation provides a resume of the potential employee to the potential employer. In another example, a meeting is automatically set up or suggested. In some embodiments, the meeting takes into account the additional information such as cuisine preferences, locations, traffic and/or any other information. In some embodiments, where the users are not direct contacts, the recommendation includes an invitation for the two to connect directly. In some embodiments, the order of the steps is modified. In some embodiments, additional or fewer steps are implemented.

In an example of a user using the social networking event planning system to find a job, the user indicates on his social networking site that he is looking for a new job. The system then analyzes his information (e.g., resume, social networking page, personal web site, personal reviews, other social networking pages, tweets, emails and/or any other information) and compares it with information regarding contacts including contacts of contacts and contacts of contacts of contacts. The comparison determines which contacts are employer level (e.g. manager or higher). Of those contacts, analysis is performed to determine if the user has skills that the employer could use. The employer may or may not have a specific job opening, but if the employer sees a contact who is a perfect fit, the employer may hire him anyway. If the system determines matching information including personal matches, skill set matches and/or any other matches, the user's contact information is provided to the potential employer and/or vice versa. In some embodiments, a match score is provided to one or both to indicate how good a match is. For example, the user is proficient in the same programming language used by the potential employer, the user's personality and hobbies match the potential employer and several of the employees already there, so the user is given a 95 out of 100, whereas a user who does not have a matching skill set and very different hobbies is given a 50 out of 100. The system is able to work similarly for an employer. The employer is able to indicate he is looking to fill a position, including providing qualities/skill preferences/requirements for the position. The system then analyzes the information about the employer including company information and the skill requirements, and compares the information with contacts to determine if any contacts have matching information. Even if the employer is not looking to fill a position, potential candidates are able to be recommended. In some embodiments, the job-matching is applied to non-contacts or non-contacts with one contact in common.

In some embodiments, the social networking event planning system is used to guide/plan for a user to change jobs every X years (e.g., every 3 years). The event planning system factors in items such as the economy, the user's qualifications, new skills learned on the current job, current positions available or future positions, available housing, and/or any other factors used to determine when and where the user's next job should be.

FIG. 6 illustrates a diagram of exemplary factors utilized in making a recommendation according to some embodiments. For example, likes, dislikes, current/predicted traffic conditions, current/predicted wait times, mood, current/future locations of contacts, diet, adventure rating, coupons, type of event/meeting, current/future weather, health, music preferences, gaming, brain wave analysis, microchip analysis, purchases, searches, tracking, patterns, to-do items, augmented reality, employment information, travel plans, pet preferences, kid preferences, items to share/give/receive, quests, real-time analysis, learning, parallel analysis, reactions, comparison shopping analysis, nanoparticle analysis, and/or any other information are able to be used to make a recommendation. Any combination of the factors is able to be utilized, and any weighting scheme is able to be applied to the factors. Although many factors are shown, the figure is not meant to be limiting in any way.

Figures 7, 8, 9:
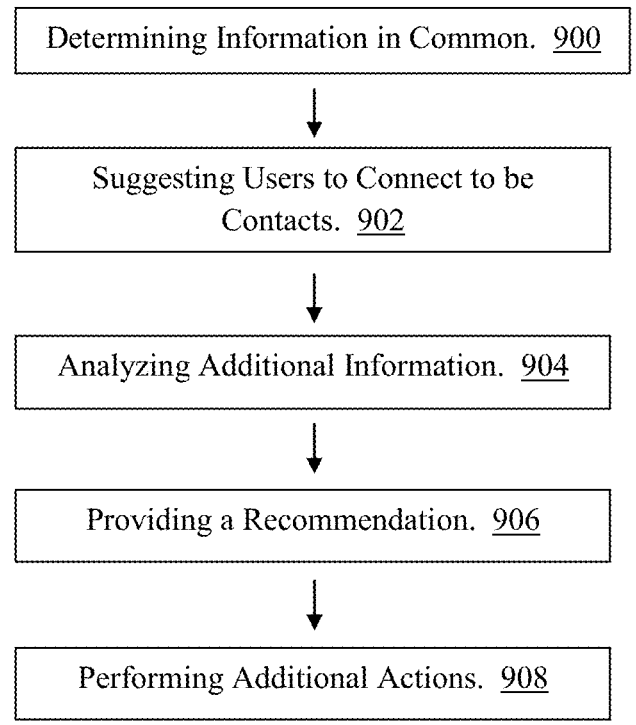
FIG. 7 illustrates a diagram of exemplary factors and weights utilized in making a recommendation according to some embodiments.
FIG. 8 illustrates a diagram of exemplary recommendation analysis according to some embodiments.
FIG. 9 illustrates a flowchart of a method of implementing event planning using social networking according to some embodiments.

FIG. 7 illustrates a diagram of exemplary factors and weights utilized in making a recommendation according to some embodiments. Although many factors are shown, the figure is not meant to be limiting in any way, and the weights are merely an example. Any weighting scheme is able to be applied.

FIG. 8 illustrates a diagram of exemplary recommendation analysis according to some embodiments. For example, calculations are performed, process of elimination is utilized, random selections are made, multiple suggestions are provided, specific details are provided, users/contacts are able to accept/reject recommendations, percentage of likelihood is utilized, images, videos and scents are provided, options are generated, wearable items indicate events, caller identification presents information, shortcut analysis is used, and/or any other recommendation analysis/presentation is performed. Although many analyses/implementations are shown, the figure is not meant to be limiting in any way.

FIG. 9 illustrates a flowchart of a method of implementing event planning using social networking according to some embodiments. In the step 900, information in common is determined. For example, a user's likes/dislikes are compared/matched with others' likes/dislikes. In the step 902, users are suggested to connect to be contacts using a social networking system. For example, if the user and other contacts have similar interests in common (e.g., score above a threshold), then they are recommended to connect. In the step 904, additional information is analyzed. In the step 906, a recommendation is provided. As described herein, the information in common and additional information are analyzed used to compute a recommendation. In the step 908, additional actions are performed. For example, a reservation at a restaurant is automatically placed, tickets are automatically purchased, a virtual reality representation is generated/presented, and/or directions to the event are generated/presented. In some embodiments, fewer or additional steps are implemented. In some embodiments, the order of the steps is modified.

Figures 10, 11:
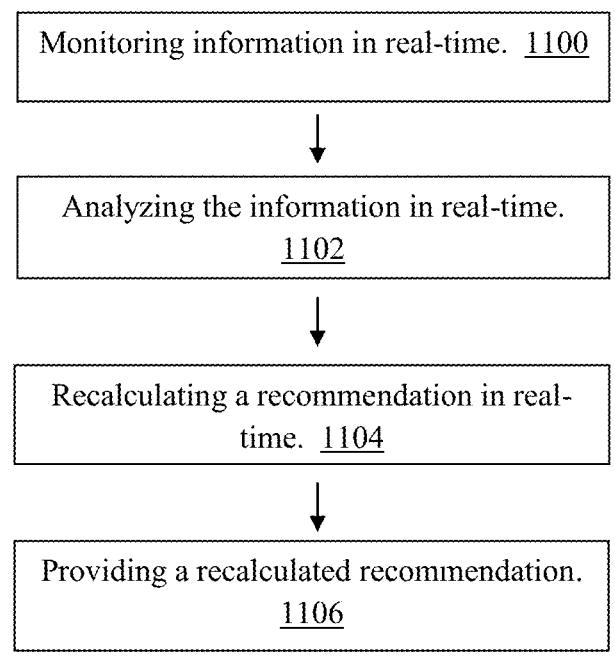
FIG. 10 illustrates a diagram of exemplary job-related recommendation analysis according to some embodiments.
FIG. 11 illustrates a flowchart of a method of implementing event planning in real-time according to some embodiments.

FIG. 10 illustrates a diagram of exemplary job-related recommendation analysis according to some embodiments. For example, common interests, personalities, locations, preferences, specific aspects, contacts, searches, salaries, and/or genetics of the potential employee/employer are analyzed, college aspects are analyzed, life planning and sequences are analyzed, and/or any other job-related recommendation analysis is performed. Although many analyses/implementations are shown, the figure is not meant to be limiting in any way.

FIG. 11 illustrates a flowchart of a method of implementing event planning in real-time according to some embodiments. In the step 1100, information related to event planning is monitored in real-time. The information monitored in real-time is any information such as weather information, traffic information, messages/social networking information between contacts (e.g., SMS messages, Tweets), restaurant wait times, and/or any other information that is able to be monitored in real-time. The information is able to be monitored in any manner such as crawling for data, retrieving and storing data, and/or any other method. The information is able to be monitored and/or analyzed using cloud computing. In the step 1102, the information is analyzed in real-time. Analyzing is able to be any analyzing/processing of the information. For example, the traffic/time of arrival for each contact of an event is continuously monitored, stored, and/or checked for any changes. For example, based on crowd-sourced traffic information, an arrival time for a contact has increased from 20 minutes to 50 minutes. In the step 1104, depending on the analysis of the information in real-time, a recommendation is recalculated in real-time. In some embodiments, information from the previous calculation is maintained and utilized except for the changed/new information. For example, if the same contacts are attending an event, then their common interests are not recalculated, but if the weather has changed, prompting a need for an indoor venue, information regarding the venue site including specifying the venue site must be indoors is utilized for a recalculation. In some embodiments, a complete recalculation is performed. In the step 1106, a recalculated recommendation is provided. For example, a new list of recommendations is provided to the contacts. Any method of providing the new/updated recommendation is able to be implemented, such as automatically selecting a new event, providing a single new recommendation, a list of recommendations for the contacts to select from, and/or any other implementation of providing the recommendation. Additionally, any of the added steps such as automatic purchasing of tickets, making a reservation, and/or generating GPS directions are able to be implemented. In some embodiments, further steps are able to be implemented such as automatically canceling the previous reservation, requesting a refund for tickets, deleting the previous GPS directions, and/or any other additional steps. In some embodiments, additional or fewer steps are implemented. For example, before the information is monitored in real-time, a previous event planning recommendation was made and accepted by the contacts. In some embodiments, the real-time event planning is only implemented at specified times. For example, the real-time event planning begins one hour before the event is planned to take place. In another example, the real-time event planning begins when at least one of the contacts begins traveling to the event (e.g., as determined by GPS tracking or a user acknowledgment when the user is leaving). In yet another example, the real-time event planning begins when one or more of the users manually trigger the real-time event planning system (e.g., by selecting real-time event planning using the GUI or a voice-activation command) In some embodiments, the real-time event planning system is utilized after an incomplete event plan has been generated and/or accepted. For example, several contacts have agreed to go to a restaurant for dinner at 6 pm on Friday, but the exact restaurant has not been generated/agreed upon. Then, at a time closer to the event (e.g., 5 pm), the real-time event planner is implemented to utilize the current information (e.g., location information of the contacts, traffic information, wait times, and/or any other current information).

In some embodiments, the event planning system generates a partial or incomplete event plan. For example, based on the common interests and additional information, a type of event (e.g., dinner, movie, hike) is recommended as well as other information such as date, time, and/or general proximity, but specific details are not generated/recommended. Users are able to specify the amount of detail to accept. For example, a user selects to receive a recommendation only for a type of event and day of the event. In another example, a user selects to receive a recommendation for a type of event, day, time, and type of cuisine. In some embodiments, the event planning system provides recommendations in steps, and if the contacts are unable to agree at that time, the event planning system leaves that information incomplete until a later time (e.g., when the real-time event planning system is implemented). For example, a message is sent to four contacts to have dinner; all accept. Then, the event planning system sends a message to the four contacts with a date for the dinner; all accept. Next, the event planning system sends a message specifying a time; but one or more of the contacts does not accept since his schedule is in flux. In some embodiments, a time/date question is asked first or questions are given priorities, and the questions are asked based on priority. The priority is able to be based on anything such as most likely to cause potential conflicts (e.g., date/time). In some embodiments, questions are able to be automatically answered/populated. For example, the system is able to check users' calendars to determine if there is a conflict. In addition to analyzing the calender/schedule, additional analysis is able to be performed such as analyzing where a schedule item is taking place and calculating travel time and other information. Users are able to input personal information/routines that may not be on their calendar (e.g., typically go to the gym at 6 p M-F), and that information is able to be stored by the system for future user. In some embodiments, users are able to designate special contacts (or the special contacts are automatically selected based on prior event planning), where the special contacts are given priority over lower priority calendar items or personal routines. In some embodiments, the event planning system stops once a decision is incomplete. In some embodiments, the event planning system continues to the next question, until the questions are exhausted. In some embodiments, the questions are all asked at the same time or are selectable options at the same time, and if there is any disagreement/conflict, then the information is incomplete until a later time.

In some embodiments, a shortcut event planning system is implemented. The shortcut event planning system is able to be implemented in any manner that lessens the workload compared with the event planning system. For example, a shortcut event planning system utilizes previously performed analysis so that analysis is not repeated. For example, if Contacts A, B and C (e.g., their common interests) have been analyzed for an event recently, then the analysis of them may not have to be repeated. In some embodiments, the shortcut event planning system is implemented if the event planning system has been used recently (e.g., within 1 day or within 1 week) for the same contacts. In some embodiments, the shortcut event planning system uses the exact same recommendation results as the previous event planning system. In some embodiments, the same results are used minus the previously accepted result. In some embodiments, an analysis is performed before determining whether to use the shortcut event planning system or the event planning system. The analysis is able to include when the last event planning system analysis was performed, if the same contacts are involved, if other conditions are similar (e.g., time of event, weather, traffic conditions), and/or any other analysis. If the analysis determines that too many variables are different, then a standard event planning analysis is performed. If the analysis determines that there are not many different variables or that they are minor, then shortcut event planning is implemented. In some embodiments, the shortcut event planning system is not implemented twice in a row. For example, after using the shortcut event planning system, then a standard event planning system is utilized.

In some embodiments, an event planning notification system is implemented. For example, for users who are not aware of the event planning system, a notification is sent to the user. In some embodiments, the notification is sent by detecting that the user utilizes a device to plan events but does not have the event planning system installed on the device. For example, User A utilizes a calendar scheduler, but a scan of the user's system indicates that an event planning system is not installed, so a message and/or advertisement is sent to the device.

In some embodiments, the event planning system is utilized in assisting in payments for items and/or services. The event planning system is able to provide pooling of money for payment. The event planning system is able to collect payments from contacts to make a payment group payment. The event planning system is able to incorporate coupons/group coupons/promotional offers from one or more of the contacts attending the event when making a payment. The event planning system is able to split payments based on each contact's purchase/order. For example, Contacts A, B and C have dinner and order different items. The event planning system is able to receive/acquire the pricing information, calculate tips and taxes based on the location and/or any other factors and provide the contacts with a recommended payment. The shared payments or group payments are able to be implemented in any manner such as having an online banking account or credit card of each user linked to the event planning system which is able to be automatically charged.

In some embodiments, the event planning system is able to be used to share events. For example, if Contacts A, B and C went to a show that they liked, the event is shared with other contacts. By sharing the event as a group, the shared information carries more weight since instead of a single review, multiple reviews are shared at once. The sharing is able to be implemented in any manner such as via a social networking site and/or messaging service. Sharing the event is able to include any amount of detail such as a simple, A, B, C enjoyed Restaurant Z, or specific details including photos, videos and/or any other content. In some embodiments, the shared events are also automatically published to review sites, or event reviews are generated where the review is by some or all of the contacts attending the event. In some embodiments, the event sharing is able to be used to generate viral marketing, for example, a shared event goes to all contacts of each of the contacts attending the event which will generate buzz for the event.

In some embodiments, a recommendation (or advertisement) is displayed only for a brief amount of time (e.g., 5 seconds or less) and then is permanently deleted/disabled from the user's device. In some embodiments, the amount of time is different, such as 30 seconds or less, one day or less, or some other time amount. In some embodiments, the amount of time begins from when the user first receives and/or opens/views the recommendation. For example, the user opens a recommendation for a restaurant, and a timer begins ticking until the time limit is up, and the recommendation is deleted. By presenting users with a timed recommendation, they are required to make a quick decision without dithering. In some embodiments, the amount of time begins when a last member of a group receives and/or opens/views a recommendation. For example, a recommendation is sent to 5 social networking contacts, and the first 4 contacts view the recommendation at 4 pm, but the fifth contact does not view the recommendation until 4:30 pm, so the timer does not start counting until 4:30 pm. In some embodiments, the recommendation includes "accept" and/or "reject" input (e.g., buttons). For example, if a user selects "accept" for a recommendation, although the recommendation disappears, the information regarding the recommendation is stored/shared (e.g., the name, address and phone number of a restaurant is saved in the user's address book or a gps waypoint is automatically set or the restaurant information is shared via social networking with other contacts). In some embodiments, only a "reject" button is displayed with the recommendation, and if the user selects "reject," then another recommendation, but if the user does not select "reject" within the designated time period, then the recommendation is automatically saved/stored/shared. In some embodiments, multiple brief recommendations are presented sequentially or randomly to a user. For example, a first recommendation is displayed for 5 seconds, and if the user selects "accept," no further recommendations are displayed. If the user does not select "accept," then after the first recommendation is displayed for the 5 seconds, a second recommendation is displayed for 5 seconds, and so on, until an endpoint is reached (e.g., a maximum number of recommendations are displayed, such as 10). In some embodiments, multiple recommendations are displayed at the same time for a time period, such as 5 recommendations are displayed for 1 minute for the user to select one of the 5 recommendations. In some embodiments, multiple recommendations are displayed at the same time for a time period, and after the time period expires, if a user has not accepted any of the recommendations or rejected the recommendations, another set of multiple recommendations is displayed and so on.

Figure 12:
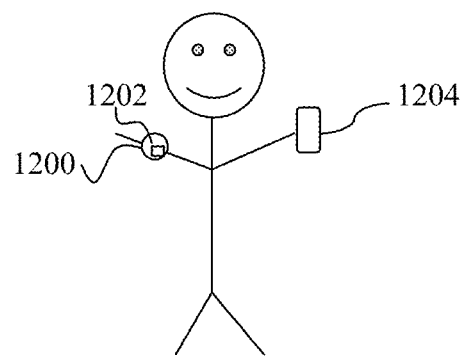
FIG. 12 illustrates a diagram of a system of devices implementing even planning in real-time according to some embodiments.

FIG. 12 illustrates a diagram of a system of devices implementing event planning in real-time according to some embodiments. The system includes a smart watch 1200 with a sensor 1202 and a smart phone 1204. The sensor 1202 is able to be any type of sensor or a combination of sensors such as a heart rate monitor, a sweat sensor, a blood sugar sensor, and/or any others. The sensor 1202 typically is on the back of the smart watch 1200 such that the sensor rests up against a user's skin so that the sensor 1202 is able to acquire health information from the user. The smart watch 1200 and smart phone 1204 are able to communicate with each other. For example, the smart watch 1200 is able to send data received from the sensor 1202 to the smart phone 1204 for further analysis. Although the smart watch and smart phone are shown in FIG. 12, any combination of devices are able to be used, such as smart clothing with a smart phone, a smart watch which communicates with the cloud, a smart watch which communicates with a personal computer, or a smart phone with a sensor which communicates with the cloud.

Figure 13:
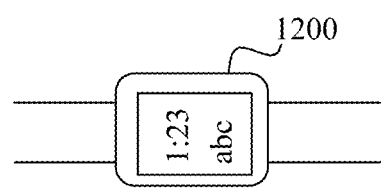
FIG. 13 illustrates a front view of a smart watch implementing the social networking event planning system according to some embodiments.

FIG. 13 illustrates a front view of a smart watch implementing the social networking event planning system according to some embodiments. The smart watch 1200 includes a face with a display for displaying any information such as time, text messages, videos, phone call information, social networking information, social networking event planning information, health information, and/or any other kind of information.

Figure 14:
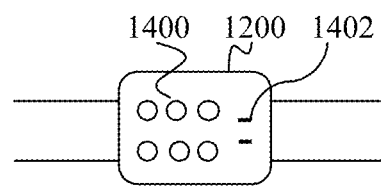
FIG. 14 illustrates a rear view of a smart watch implementing the social networking event planning system according to some embodiments.

FIG. 14 illustrates a rear view of a smart watch implementing the social networking event planning system according to some embodiments. The smart watch 1200 includes one or more sensors/devices (e.g., optical device)/accelerometers 1400 and/or contacts 1402. The sensors 1400 are able to be any kind of sensor such as a pressure sensor, laser sensor, moisture/liquid sensor, air pressure sensor, substance sensor, temperature sensor, heat sensor, body fluid sensor, gas/liquid/fluid sensor, electricity/electrical conductivity sensor, audio/sound/sound wave sensor, oxygen sensor (e.g., a pulse oximeter used to measure oxygen levels in the blood), and/or any other sensors. In some embodiments, the device includes one or more accelerometers. In some embodiments, the device includes a camera for analysis. In some embodiments, the device includes an ultrasound component for detecting objects/material using sound waves.

The pressure sensor is able to measure muscle tightness, blood pressure, heart rate/pulse and/or other pressure-related events. The laser/light sensor is able to be used to count blood cells (white and/or red) and/or detect other particles within the body. The moisture sensor is able to be used to measure an amount of moisture on skin (e.g., sweating) or in the air (e.g., humidity). The substance sensor and/or body fluid sensor is able to be used to detect salinity levels in sweat, or vitamins, alcohol, drugs, or other substances in the sweat, skin or other body part/discharge. The temperature sensor is able to be used to determine a body temperature and/or an external temperature. The heat sensor is able to be used to sense heat.

In some embodiments, a pressure sensor is able to detect increases in pressure from a user's heartbeat/pulse. Additionally, arrhythmias are able to be detected by monitoring the user's pulse. For example, the sensor and/or application count the beats and the time between to determine any differences in the time between the beats. In some embodiments, an application compares normal beats versus irregular beats. For example, the application detects a pattern (e.g., fast beats followed by slow beats followed by fast beats could indicate aFib, or fast beats over 100 beats per minute indicates tachycardia, and beats over 200 beats per minute indicates something else). Additional information is able to be acquired as well to determine if the change in pulse is normal or abnormal. For example, a sweat sensor determines that the user is sweating which could be based on exercise. In another example, an accelerometer detects that the user is swinging her arms, which again indicates that the user is exercising, and thus the increased pulse is likely normal. In yet another example, a microphone of the device detects that the user is just screamed, indicating fright, so that could be the cause for the increase in pulse. In another example, the user's schedule is cross-checked (e.g., exercise is at 5:00p, so accelerated heart rate at 5:03p is likely based on the exercise.

In some embodiments, a moisture/humidity sensor is used to detect moisture of the skin to determine dehydration. Dehydration is also able to be detected based on salinity levels in the skin or sweat. Dehydration is also able to be detected using light/laser to analyze water in cells or other cellular features. For example, if the cells have less liquid in or near them than is standard or versus a baseline of the user, then dehydration is detected, and an alert is able to be triggered (e.g., changing the backlight of the device to a blue color or sending a text message).

In some embodiments, the light/laser sensor detects low sugar levels.

In some embodiments, an audio detector, a vibration detector, and/or a pressure detector are used separately or together to detect anxiety and/or other mental health issues.

In some embodiments, the laser sensor and/or ultrasound sensor are used to measure the size of a blood vessel/vein/artery and/or delta of the size of the blood vessel/vein/artery.

The sensors are able to be used individually or together to detect immune response/activity, panic attacks, mood, inflammation, sun burn, an injury, and/or other aspects.

In some embodiments, the device is able to change colors based on events/aspects (mood, injury, and/or other information). For example, the display changes color, or the band changes color (e.g., one or more lights in the band illuminate the band). Furthering the example, if a health condition is detected, the watch is illuminated red.

Figure 15:
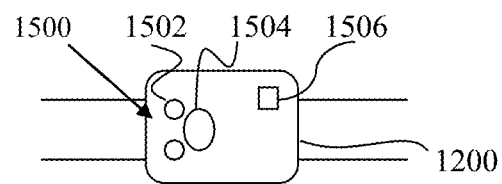
FIG. 15 illustrates a rear view of an optical device on a device according to some embodiments.

FIG. 15 illustrates a rear view of an optical device on a device according to some embodiments. In some embodiments, the device 1200 includes an optical device 1500 to provide oblique illumination with a light source 1502 (e.g., one or more LEDs, lasers and/or any other light source). The optical device 1500 utilizes image/video capturing elements 1504 (e.g., a lens and sensor) to capture one or more images or videos of capillaries/veins/arteries under the skin with cellular resolution. The images/videos are then analyzed to detect white blood cells and calculate the concentration of white blood cells. The optical device 1500 includes a small lens which captures images blood flowing. When illuminating at certain frequencies, the light is absorbed by the hemoglobin in the red blood cells, which does not happen with the white blood cells. Thus, the white blood cells appear as transparent (or semi-transparent) particles moving inside the capillary. The particles (white blood cells) are able to be analyzed/counted, and based on blood flow rate and/or other variables, a concentration of white blood cells is able to be determined. In some embodiments, the light affects the white blood cells so that they stand out and are more easily detected/counted. The optical device 1500 is able to be used to detect illnesses that affect white blood cell count including, sepsis, infection and/or cancer.

In some embodiments, the optical device 1500 is used to detect hormones such as human chorionic gondotropin (hCG) which indicates pregnancy. As time passes after conception, the amount of hCG in the bloodstream or sweat increases. In some embodiments, the optical device 1500 detects changes in the amount of hCG in the user's blood, and if the change is above a threshold or the overall amount of hCG detected is above a threshold, then a pregnancy alert is triggered.

The optical device 1500 functions by providing a light on the user's skin which penetrates the user's skin and into the hemoglobin in red blood cells but not white blood cells. Since the white blood cells are not affected, the camera of the optical device is able to capture the white cells in images or video. The video is then processed using an image processing system 1506 which could be on the optical device 1500, the device 1200 and/or a remote device (e.g., a processing server). The image processing system 1506 is able to be implemented in any manner. For example, the image processing system 1506 determines the blood flow rate and the number of white blood cells counted for a certain amount of time. Then, based on the rate and count, a concentration is able to be generated. The concentration is able to be compared to a baseline or average white blood cell concentration particular to the person and/or a general white blood cell concentration. For example, each day for a month, the optical device 1500 is implemented for a specified time period (e.g., several seconds to several minutes) to determine a white blood cell concentration of a user using the device. The white blood cell concentration is averaged or another mathematical operation is implemented to determine a baseline. Then, the optical device 1500 periodically (e.g., 1 time per day, 3 times per day, 1 time per week, 1 time per month) checks the user's white blood cell concentration and compares the present value with the baseline. Based on the comparison, an alert or notification is able to be provided to the user via the device (e.g., an icon is displayed indicating a medical issue or the backlight color changes from green to red).

In some embodiments, the device 1200 is able to be used to detect coughing. Coughing is able to be detected by detecting a coughing sound and/or a muscle contraction. Similarly, sneezing is able to be detected based on the sound and/or body movement such as the head moving forward quickly (e.g., with a motion sensor in earrings, eyeglasses or hat). In some embodiments, additional symptoms are monitored and/or checked such as sweating on and off, body temperature going up and down, and/or other symptoms. The coughing and/or other symptoms are able to be detected and/or tracked to make a diagnosis. For example, most people do not remember when symptoms start, but the device 1200 is able to track any and all symptoms. In some embodiments, the device auto-communicates (or manually) with a medical facility for treatment (e.g., call 911, find emergency wait times, set up an appointment with a doctor).

In some embodiments, a belt/belt buckle and/or pant waistline includes one or more sensors for detecting abdominal issues/symptoms (e.g., gurgling noises, distended belly).

Figure 16:
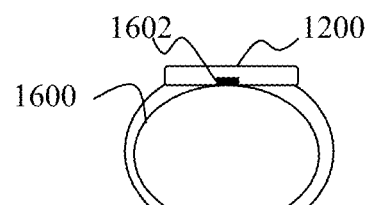
FIG. 16 illustrates a view of a device with a cuff/sensor system according to some embodiments.

FIG. 16 illustrates a view of a device with a cuff/sensor system according to some embodiments. In some embodiments, the device 1200 (e.g., watch) includes an embedded, separate and/or detachable (inflatable) cuff 1600 and sensor 1602 system. For example, the cuff 1600 inflates and deflates similar to a blood pressure device and the sensor 1602 is able to determine the blood pressure based on how the cuff affects the user's body. In some embodiments, a device includes a laser/light/sound sensor which is able to measure flow rate and/or size of artery/vein/blood vessel (changes). For example, a light sensor is able to send light pulses to determine how much blood is flowing, or take a sequence of images to determine changes in the size of an artery.

Figure 17:
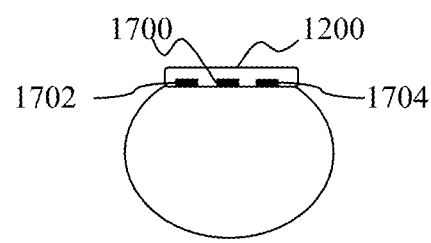
FIG. 17 illustrates a view of a device with a heating and/or cooling element according to some embodiments.

FIG. 17 illustrates a view of a device with a heating and/or cooling element according to some embodiments. In some embodiments, the device includes a sensor for body temperature and/or air temperature as well as a heating and/or cooling element to heat or cool the person. For example, the device 1200 is a watch which includes a body temperature sensor 1700. The watch also includes a cooling element 1702 (e.g., one or more tubes in which coolant is able to pass through) and/or a heating element 1704. In another example, the watch includes one or more metal wires which are able to be heated and/or cooled (e.g., using electrical pulses). Furthering the example, when the person's body temperature rises above a threshold (e.g., 99 deg. F.), then the cooling element 1702 is triggered which helps lower the user's body temperature, and when the person's body temperature drops below a threshold (e.g., 97 deg. F., then the heating element 1704 is triggered which helps raise the user's body temperature. In some embodiments, the device includes additional sensors as described herein such as an external temperature sensor. In another example, when the outside temperature is above a threshold (e.g., 90 deg. F.), then the cooling element 1702 is triggered, and when the outside temperature is below a threshold (e.g., 32 deg. F.), then the heating element 1704 is triggered. In some embodiments, the heating element 1704 and the cooling element 1702 are the same device (e.g. a single wire or multiple wires which are able to be heated or cooled), and in some embodiments, the heating element 1704, cooling element 1702 and the sensor 1700 are all implemented as a single unit. In some embodiments, the heating element 1704 and/or cooling element 1702 are positioned anywhere on the device 1200; for example, on a watch's back/backplate and/or a watch's band. The heating 1704 and cooling element 1702 are able to receive signals either wirelessly or via wires of the device (e.g., wires embedded in the watch band).

Figure 18:
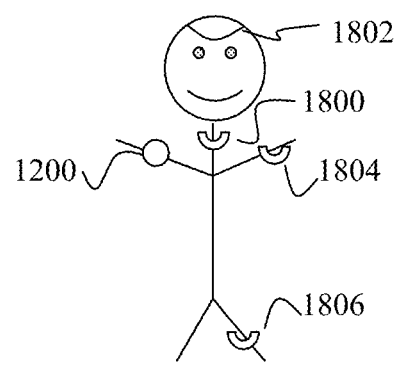
FIG. 18 illustrates a view of multiple devices implemented to operate together/in sync to heat and/or cool the user according to some embodiments.

FIG. 18 illustrates a view of multiple devices implemented to operate together/in sync to heat and/or cool the user according to some embodiments. For example, the user wears a device 1200 (e.g., watch), a necklace 1800, a headband 1802, a bracelet 1804 and an anklet 1806, all of which have heating and/or cooling capabilities and/or wireless communication capabilities (e.g., Bluetooth®). When the user's body temperature and/or outside temperature is above a threshold (or another trigger occurs), the devices work in conjunction to cool the user's body, and when the user's body temperature and/or outside temperature is below a threshold, the devices work together to heat the user's body. The watch or other device is able to communicate to the other devices (e.g., necklace, bracelet, anklet) via any wireless implementation (e.g., Bluetooth®, wifi, NFC).

In some embodiments, multiple devices operate together for other tasks. For example, a watch sends a signal to a necklace or headband to provide an electrical pulse to the user's neck/head (e.g., to wake up).

The information acquired from the sensors is able to be analyzed at the watch and/or in another device (e.g., in the cloud) and used to provide additional input for the social networking event planning. For example, by determining that a user's body temperature is above normal, soup is recommended for the next meal, and it is recommended for the user to skip exercise that day.

In some embodiments, multiple sensors are used in conjunction for analysis.

In some embodiments, the body information (e.g., sweating, heart rate) is tracked in addition to what the user is doing (e.g., audio/video detection or based on schedule or other analysis) to make a recommendation (e.g., job, meal, activity). For example, a user's heart rate or blood pressure goes up dramatically every day at the user's job, so a less stressful job is recommended to the user or exercise is suggested to deal with the stress.

In some embodiments, a combination of devices is used (e.g., watch+necklace, watch+bracelet/band, watch+earring, internal device+external device).

In some embodiments, other devices such as clothes, a band, a patch, a belt, jewelry, and/or headphones are equipped with one or more sensors and/or other instrumentation.

In some embodiments, the device is able to be used to perform group activities such as health activities (e.g., exercise competitions, training together). In some embodiments, social networking is utilized for the group activities. For example, users are able to share and compare the amount of miles they have run in a time period (e.g., week) and their times.

In some embodiments, the device is able to be used to calculate repetitions (e.g., based on detecting movement using the accelerometer).

In some embodiments, multiple power sources are utilized to power the device including but not limited to a battery, a kinetic energy generator, and/or a solar cell.

In some embodiments, the device implements a 3D press implementation such that the harder a user presses on the screen of the device, a different effect/action occurs. For example, as a user presses lightly on the screen of the device, a first effect/action occurs, but if a user presses harder, then a second effect/action occurs. In some embodiments, there is only a soft/quick press and a longer/harder press, and in some embodiments, there are more than two levels of presses. The different presses are able to be determined based on the amount of pressure detected and/or the duration of the press, and then that information is able to be compared with a database which associates pressure/duration with an effect/action.

Figure 19:
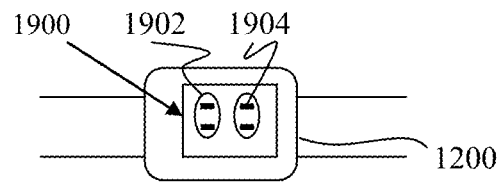
FIG. 19 illustrates a rear view of a sweat sensor on a device according to some embodiments.

FIG. 19 illustrates a rear view of a sweat sensor on a device according to some embodiments. In some embodiments, a sweat collection implementation 1900 is part of the device 1200 and/or is a detachable component of the device 1200. The sweat collection implementation 1900 is able to include components such as zones of a sweat-porous product 1902 and electrodes 1904. In some embodiments, the sweat collection implementation 1900 includes separate circuitry such as wires, microchips and an antenna from the device 1200, and in some embodiments, the components of the device 1200 are used. In some embodiments, the device 1200 is able to stimulate sweat and/or measure sweat. In some embodiments, the device 1200 detects sweat (e.g., during exercise) and then uses the sweat for analysis (without having to stimulate sweat). In some embodiments, the device 1200 stimulates sweat using iontophoresis by placing an electrically charged medication on the skin and using an electrode and low current to draw the medication into the skin. In some embodiments, a user puts the medication on the skin. The device 1200 is able to process the sweat analysis data and/or the device 1200 sends the data to another device (e.g., a smart phone, a computer, a cloud server) for processing and/or other analysis. In some embodiments, the device 1200 includes a circuit (flexible or non-flexible), one or more microchips, and an antenna. In some embodiments, the device 1200 also includes a sweat-porous product which is permanent or replaceable. In some embodiments, the sweat-porous product is designed to acquire a specific ion (e.g., chlorine). In some embodiments, the sweat-porous product is designed to acquire multiple ions (e.g., the product has multiple zones and each zone is configured to receive a specific ion (e.g., a first zone for sodium, a second zone for chlorine and a third zone for potassium). In some embodiments, onboard circuitry (e.g., in the device 1200 or on the device 1200) is used to calculate the ion concentration.

In some embodiments, the circuitry includes an electrode coated with an ion-selective membrane and a reference electrode. The coating is able to be a standard polymer along with a special ionophore molecule that allows passage of only one type of ion. Then, voltages are able to be measured using the device 1200 including calculating the voltage induced by the ion-selective membrane and calculating the ion concentration from that. In some embodiments, the electrode is coated with an enzyme specific to a particular metabolite such as glucose oxidase or lactate oxidase.

In some embodiments, a hydrogel is included with the device 1200 or the sweat collection implementation 1900 to absorb the sweat.

In addition to detecting/monitoring sodium, chlorine, potassium, other nutrients, vitamins, electrolytes, hormones, chemicals are able to be detected such as metabolites (e.g., lactate, creatinine, glucose) and other biomarkers (e.g., cytokines such as interleukin 6) which indicate stress, disease, poor nutrition, injury, infection, cancer, and other conditions. In some embodiments, alcohol and/or other drugs are detected using the sweat sensor or another sensor. By detecting and/or monitoring these substances, food/drink suggestions are able to be made as well as other health recommendations such as getting more exercise or less sun.

In some embodiments, an electrode is coated with a biorecognition element which matches up and holds a biomarker trying to be sensed. Then, based on an electrical signal and current, measurements are able to be taken. Additionally, a redox couple is able to be added to the biorecognition element.

In some embodiments, the device 1200 includes nanowires, nanotubes and/or graphene electrodes which are coated with biorecognition elements.

As described above, pregnancy is able to be detected using the device 1200. In some embodiments, pregnancy is detected by analyzing the amount (or changes in the amount) of hCG and/or other hormones in the user's sweat, and the user is alerted if she is pregnant. The information of being pregnant is also able to be coupled with other aspects of the social networking event planning system such as drafting a birth announcement for the user to send, finding and/or displaying advertisements (e.g., display baby product advertisements after pregnancy is detected), and providing alerts when the user is doing activities such as to avoid alcohol and smoking.

In some embodiments, detecting pregnancy is performed by other analysis such as monitoring other symptoms such as morning sickness (e.g., detecting specific motion or sound) using the device 1200 (e.g., using the microphone and accelerometer), detecting other physical changes of the body (e.g., gaining weight) using the device 1200, and/or any other analysis. In some embodiments, the device 1200 is worn near a female's waist (e.g., on a belt buckle), and the device 1200 includes ultrasound capabilities (or similar technology), and using the ultrasound technology, it is able to be determined if the user is pregnant.

In some embodiments, the device 1200 is able to be used to detect intoxication (e.g., alcohol, marijuana, and/or other drugs). The device 1200 is able to use a combination of devices (or single device) to determine intoxication. For example, the microphone of the device 1200 is able to be used to acquire the user's speech, and the processor or an external processor is used to compare the user's current voice with his/her previously recorded voice and determine if there is a difference such as slurring. The accelerometer of the device 1200 is able to be used to determine if the user is walking different (e.g., swaying, tripping often). Again, the movements are able to be compared with previously recorded movements or a history of movements. The accelerometer is also able to be used to track arm movements to indicate how many time a user places a glass to his/her mouth. The camera of the device 1200 is able to acquire video. In some embodiments, the user holds the camera towards his eye and the camera analyzes the movement of the user's pupil to determine if the user is intoxicated. The device 1200 is also able to communicate with other devices (e.g., signal to the user's car to prohibit the car from starting if the user is behind the wheel or to trigger autopilot driving or to call for a car or friend to pick up the user to drive the user home). The device 1200 is also able to geotag the location of the user's car if the user takes an alternative mode of transportation so that the user is able to easily find his car later (e.g., the next day).

In some embodiments, one or more sensors of the device 1200 are used to detect allergen information in the air. For example, a sensor takes air samples which are analyzed to determine which particles are in the air. In some embodiments, the device 1200 communicates with an external device which is configured to analyze air samples to determine air quality including allergens in the air, and then the external device sends the information or a result back to the device 1200 which is able to present the information such as provide an allergen alert or detailed information. In another example, the device 1200 uses social networking analysis to determine allergy information. For example, the device 1200 or a cloud device crawls social networking information, and if, based on the crawling, it is determined that many people within an area tweet about pollen, then an alert is triggered to warn the user about pollen. In another example, the device 1200 searches one or more databases for allergen information to trigger an alert.

In some embodiments, the device 1200 is able to measure an amount of weight of the user by measuring fat cells (e.g., quantity and/or size) and or characteristics of the fat cells such as the amount of water in the fat cells or using the water amount in the fat cells or changes in water amount in the cells.

In some embodiments, a medication storage holder is included in the device and/or is able to be attached/detached to the device. In some embodiments, the medication is able to be injected into the user directly from the device.

In some embodiments, the device 1200 is able to provide treatment to the user. For example, the device 1200 includes electric/electronic components to generate magnetic waves which are able to assist with joint pain. Similarly, the heating and cooling mechanisms described herein are able to be used for treatment of injuries. Additionally, light is able to be projected into the body for treatment.

In some embodiments, hairs are used to measure body information. For example, an electric pulse is sent through a hair, and the response of the electric pulse/hair/skin is detected and analyzed.

In some embodiments, a sensor is able to be embedded in a tattoo-like fashion to detect substances and relay the information to another device.

Figure 20:
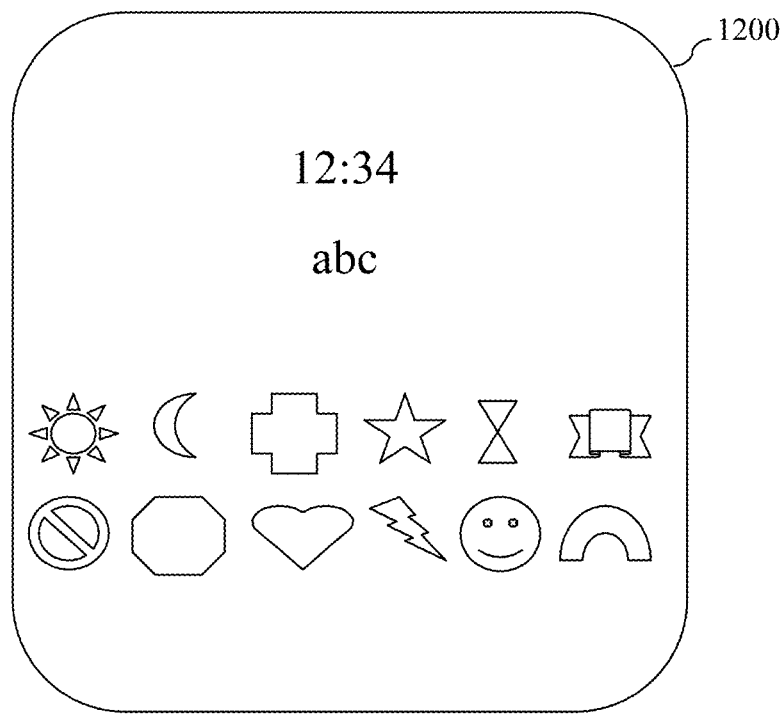
FIG. 20 illustrates a front view of a smart watch implementing the social networking event planning system according to some embodiments.

FIG. 20 illustrates a front view of a smart watch implementing the social networking event planning system according to some embodiments. The smart watch is able to display any alphanumeric information such as the time, messages, alerts. The smart watch is also able to display images, videos, and/or any other content. The smart watch is also able to display icons to alert/inform the user. For example, the icons are able to inform the user regarding the weather, medical information, a medical emergency, an appointment/deadline, an award, a restriction (e.g., dietary restriction or food to avoid), and/or any other information.

In some embodiments, a virtual reality headset is used in conjunction with the watch or other device.

In some embodiments, the device is used for exercise. For example, an accelerometer in the device 1200 is used to figure out which exercise is being performed. For example, the accelerometer determines the motions of the device and compares the motions with a database or other data structure to determine which exercise is being performed. For example, if the device is a watch, and the watch moves in a straight up and down motion, then based on a database which correlates up and down motion of the arms as a shoulder press, the exercise is determined. In some embodiments, other information is used to determine the exercise such as a camera in the device, communicating with other wearable devices (e.g., wirelessly coupled anklet, necklace, clothing) or exercise equipment (e.g., smart dumbbells, treadmill), and/or any other mechanism to determine which exercise is being performed. Additionally, the device is able to be used to track exercise aspects such as the amount of weight used, repetitions performed, duration of exercise, and/or any other information. For example, the weight is able to be determined based on the camera of the device acquiring an image of the weight number, the repetitions are able to be determined based on how often a certain movement is performed or how often the device goes to X position/orientation, and the device is able to track the passage of time while the user is active (e.g., the accelerometer in the device continues to move a certain way). In some embodiments, the exercising is synchronized with a video/game (e.g., youtube.com) to determine if the movements match or to enable the user to see the proper form for the exercise.

Caloric information such as the number of calories burned is able to be determined based on the exercise information gathered, and then that information is able to be used in recommending food items, restaurants and/or other activities. Similarly, food items, restaurants and/or other activity information are able to be used to recommend an amount of exercise. For example, if the user eats a high caloric breakfast and does not have anything scheduled for later in the day, then the system is able to recommend an exercise routine to burn a percentage of the calories acquired at breakfast. In some embodiments, the system factors in later meals as well. In some embodiments, the system automatically acquires a workout video corresponding to the desired amount of calories to burn. For example, if it is determined the user should burn 400 calories, then an exercise video which burns 400 calories is found and played for the user. In some embodiments, the user is provided with options (e.g., you could run 3 miles or select from videos 1-5 and do the exercise, or combine any two videos from videos 6-10 and do the exercises). In some embodiments, the other plans such as errands are factored in as well such as recommending running to the grocery store to buy a needed food item, and then walking home with the food item, which will burn X calories.

In some embodiments, the exercise information is utilized in a group setting (e.g., shared using social networking or any other manner). In some embodiments, the exercise information is used for group comparison purposes. For example, a user and her friends have an exercise competition to see who can exercise the most consistently. The exercise data is tracked using the device and compared among the friends. Analysis and other information is able to be provided as well. In some embodiments, rewards are able to be provided in an individual or group setting based on the exercise information. For example, if the group of friends each exercise for 5 days a week for 30 minutes a day, then they will each receive a free gift/coupon/other reward.

Any of the health/exercise/sensor implementations are able to be used in conjunction with the social networking event planning system.

In some embodiments, browser information (e.g., sites visited), search input, GPS information (including places visited as determined by referencing GPS positions of the device and comparing those locations with a database which indicates what is at that location (e.g., which store)) is tracked. Additionally, purchases/rentals are tracked. Once a product is purchased, that product is no longer advertised (at least for a predetermined period of time). For example, if a user searches for a car using a search engine, typically car advertisements are displayed in advertisements when the user visits other web pages. However, if it is determined that the user purchases a car, then car advertisements are specifically excluded for 1 year or until it is determined the user is clearly looking to purchase another car (e.g., determining the user searched at least 3 sites for a car or input "car" in a search engine 3 times). In some embodiments, in addition to or instead of excluding the car advertisements, advertisements for related items such as car insurance and/or car accessories are advertised.

Figure 21:
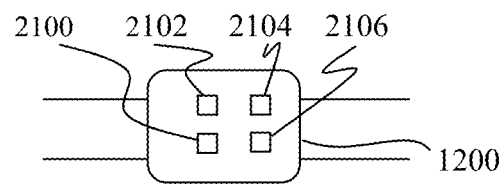
FIG. 21 illustrates internal components of the device according to some embodiments.

FIG. 21 illustrates internal components of the device according to some embodiments. The device 1200 is able to include any computing components. For example, the device 1200 includes one or more processors 2100, one or more memories 2102, one or more communications components 2104, (e.g., wi-fi and Bluetooth-enabling devices), and one or more additional components 2106 (e.g., an accelerometer and a gyroscope). The components are used to implement the methods and systems described herein. Additional or fewer components are able to be implemented.

In some embodiments, the social networking event planning system is a smartphone/smartwatch application including, but not limited to, an Apple Watch®, iPhone®, Apple OS®, Droid® or Blackberry® application.

Any of the steps described herein are able to be implemented automatically, manually, and/or semi-automatically. Any of the steps described herein are able to be implemented in real-time or non-real-time. By real-time, the step is able to be implemented within a second or several seconds. Any of the steps described herein are able to be implemented locally, using cloud computing and/or a combination of both.

Utilizing the social networking event planning system, method and device assists a user in planning an event. In some embodiments, an event and contacts (or contacts of contacts) are recommended without any input from a user. In some embodiments, an event and/or contacts are recommended based on a monitored conversation or information. In some embodiments, a user requests a recommendation.

In operation, the social networking event planning system, method and device monitors, processes, and analyzes information to provide a recommendation. The analysis includes items such as determining common interests of users, locations of users, traffic information, wait times (to be seated and/or for preparing food), pricing information, and/or any other relevant analysis. The recommendation is one that is likely to receive a positive response from the contacts. The social networking event planning system improves implementations of connecting people with people, connecting people with events, connecting events with people by improving the quality of the connections as well as improving the efficiency of determining the connections. The social networking event planning system makes the planning of events more efficient.

Although some implementations and/or embodiments have been described related to specific implementations and/or embodiments, and some aspects/elements/steps of some implementations and/or embodiments have been described related to specific implementations and/or embodiments, any of the aspects/elements/steps, implementations and/or embodiments are applicable to other aspects/elements/steps, implementations and/or embodiments described herein.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A wearable device comprising:
   a device body;
   a body fluid sensor coupled to the device body, the body fluid sensor configured for sensing one or more body fluids used to generate body fluid analysis information, wherein the body fluid sensor comprises a moisture sensor including a sweat collection implementation including: one or more flexible circuits including an electrode coated with an ion-selective membrane and a reference electrode, and a plurality of zones, wherein each zone of the plurality of zones is configured to receive a specific ion; and
   a processor configured for:
      determining information in common between a plurality of contacts of a social networking system;
      analyzing the body fluid analysis information;
      analyzing video game information by performing statistical analysis of a correspondence of video game information and real life information to generate video game analysis information;
      analyzing social media information of a user to determine preferences including cross-referencing a corresponding review of a product or a service related to the social media information;
      determining mood information of the user based on facial analysis using a camera device of the wearable device and analysis of the social media information;
      detecting a second device using near-field communication, and when the second device comes within a distance threshold a greater number of times than a number threshold, analyzing the information in common between the user of the wearable device and a user of the second device; and
      providing an event recommendation by computing recommendation scores based on the information in common, the body fluid analysis information, the social media information, the mood information and the video game analysis information, wherein the event recommendation is provided based on a current time and location of the user of the wearable device and the user of the second device without the user of the wearable device or the user of the second device requesting the event recommendation.

2. The wearable device of claim 1 wherein the processor is further configured for analyzing additional information comprising determining if a group coupon offered to a group of users has been purchased by at least one contact of the plurality of contacts and increasing a recommendation score of an event associated with the purchased group coupon, and the additional information is utilized in computing the recommendation scores.

3. The wearable device of claim 1 wherein the processor is further configured for analyzing additional information comprising determining a type of event based on keywords detected in a communication between the plurality of contacts and determining a relationship of the plurality of contacts, further wherein the event recommendation includes a list of event recommendations wherein a user selects a subset less than all of the list of event recommendations, and only the subset less than all of the list of event recommendations is sent to the plurality of contacts of the social networking system, and the additional information is utilized for providing the event recommendation.

4. The wearable device of claim 1 further comprising a hydrogel configured for absorbing sweat.

5. The wearable device of claim 1 wherein the processor is further configured for analyzing additional information comprising analyzing a to-do list of at least one contact of the plurality of contacts of the social networking system to determine if items on the to-do list are located near an event to recommend, and increasing a recommendation score of the event based on the to-do list, wherein the items on the to-do list that have an importance ranking below an importance threshold are ignored when computing the recommendation score, further wherein a user ranks the items on the to-do list such that an item at a top of the to-do list has a highest priority when computing the recommendation score, further wherein computing the recommendation score includes calculating a base recommendation score and a bonus score, wherein the bonus score is based on the to-do list and is added to the base recommendation score to generate a total recommendation score, and the additional information is utilized for providing the event recommendation.

6. The wearable device of claim 1 further comprising an optical device configured to provide oblique illumination with a light source, wherein the optical device utilizes one or more content capturing elements to capture content of internal structures for analysis.

7. The wearable device of claim 6 wherein the optical device is configured to detect hormones including human chorionic gonadotropin (hCG) including detecting a delta between a first amount of hCG and a second amount of hCG, and when the delta between the first amount of hCG and the second amount of hCG is above a threshold, a pregnancy alert is triggered.

8. The wearable device of claim 1 wherein the sweat collection implementation comprises a biorecognition electrode coated with a biorecognition element for matching a biomarker.

9. The wearable device of claim 1 further comprising at least one of a heating component and a cooling component, the heating component configured for providing heat to a user, and the cooling component configured for providing cold to the user, wherein the wearable device communicates with at least one of the heating component and the cooling component to trigger at least one of the heating component and the cooling component based on the body fluid analysis information.

10. The wearable device of claim 1 further comprising an accelerometer configured for determining motion of a user, wherein the motion of the user is used to determine exercise information by comparing the motion of the user with a database of motions to determine which exercise is performed, further wherein the accelerometer is used to determine caloric information related to the exercise, and the caloric information is utilized for computing the event recommendation.

11. The wearable device of claim 1 wherein the processor is further configured for cross-checking the body fluid analysis information with a schedule to determine health information, wherein the health information is utilized for computing the event recommendation.

12. The wearable device of claim 1 further comprising a communication device configured for communicating with a second device to receive allergy information regarding a food service location by detecting that the wearable device is within a specified proximity of the food service location.

13. The wearable device of claim 1 further comprising an implantable microchip configured for detecting body fluid information by detecting chemical changes within the user and communicating the body fluid information to the wearable device, wherein computing the recommendation scores is based on the body fluid information.

14. The wearable device of claim 1 further comprising the camera device configured for recognizing a reaction to the event recommendation utilizing image or video analysis after providing the event recommendation, and processing the reaction including storing the event recommendation, the reaction and a recommendation score based on the reaction.

15. The wearable device of claim 1 wherein the processor is further configured for analyzing a user's viewing habits by determining what information from a web page is actually read by a user by recognizing only text displayed on a screen of the wearable device and ignoring text of the web page that is not displayed on the screen of the wearable device.

16. The wearable device of claim 1 wherein the processor is further configured for analyzing a musical rating of the at least one contact, wherein the musical rating is determined based on selections of likes and dislikes of by the at least one contact of the plurality of contacts of the social networking system, wherein the musical rating of the at least one contact increases based on a number of genres of music in the at least one contact's song selections, and wherein computing the recommendation scores factors in the musical rating of the at least one contact.

17. The wearable device of claim 1 wherein the wearable device acquires additional information by:
capturing one or more images or videos and utilizing image or video analysis including matching the one or more images or videos to one or more templates to generate image information, and
capturing audio and implementing audio analysis to generate audio information, wherein the image information and the audio information are utilized when providing the event recommendation.

18. A method comprising:
determining, with a wearable device, information in common between a plurality of contacts;
sensing, with a body fluid sensor of the wearable device, one or more body fluids to generate body fluid analysis information, wherein the body fluid sensor comprises one or more flexible circuits including an electrode coated with an ion-selective membrane and a reference electrode, and a plurality of zones, wherein each zone of the plurality of zones is configured to receive a specific ion;
analyzing, with the wearable device, the body fluid analysis information;
analyzing video game information by performing statistical analysis of a correspondence of video game information and real life information to generate video game analysis information;
analyzing social media information of a user to determine preferences including cross-referencing a corresponding review of a product or a service related to the social media information;
determining mood information of the user based on facial analysis using a camera device of the wearable device and analysis of the social media information;
detecting a second device using near-field communication, and when the second device comes within a distance threshold a greater number of times than a number threshold, analyzing the information in common between the user of the wearable device and a user of the second device; and
providing, with the wearable device, an event recommendation by computing recommendation scores based on the information in common, the video game analysis information, the body fluid analysis information, mood information, and the social media information, wherein the event recommendation is provided based on a current time and location of the user of the wearable device and the user of the second device without the user of the wearable device or the user of the second device requesting the event recommendation.

19. A system comprising:
a first wearable device; and
a second wearable device including:
a device body;
a body fluid sensor coupled to the device body, the body fluid sensor configured for sensing one or more body fluids used to generate body fluid analysis information, wherein the body fluid sensor comprises one or more flexible circuits including an electrode coated with an ion-selective membrane and a reference electrode, and a plurality of zones, wherein each zone of the plurality of zones is configured to receive a specific ion;
a processor configured for:
determining information in common between a plurality of contacts of a social networking system;
analyzing the body fluid analysis information;
analyzing social media information of a user to determine preferences including cross-referencing a corresponding review of a product or a service related to the social media information;
determining mood information of the user based on facial analysis using a camera device of the wearable device and analysis of the social media information;
providing an event recommendation by computing recommendation scores based on the information in common, the body fluid analysis information, the mood information and the social media information;
detecting a third device using near-field communication, and when the third device comes within a distance threshold a greater number of times than a number threshold, analyzing the information in common between the user of the second wearable device and a user of the third device; and
an implantable microchip configured for detecting body fluid information by detecting chemical changes within the user and communicating the body fluid information to the second wearable device, wherein computing the recommendation scores is based on the body fluid information.

20. The wearable device of claim 1 wherein the processor is further configured for:
analyzing ratings of restaurants generated by the user of the wearable device and the user of the second device via an online rating service, and wherein providing the event recommendation by computing the recommendation scores based on similarities between the ratings of the restaurants by the user of the wearable device and the user of the second device.

* * * * *